US011732240B2

(12) United States Patent
Kim et al.

(10) Patent No.: US 11,732,240 B2
(45) Date of Patent: Aug. 22, 2023

(54) DIRECT CONVERSION METHOD OF SOMATIC CELL INTO HEPATIC STEM CELL, HEPATIC CELL, OR CHOLANGIOCYTE

(71) Applicant: UNIST(ULSAN NATIONAL INSTITUTE OF SCIENCE AND TECHNOLOGY), Ulsan (KR)

(72) Inventors: Jeong Beom Kim, Ulsan (KR); Myung Rae Park, Ulsan (KR); Man Sze Wong, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 717 days.

(21) Appl. No.: 15/661,191

(22) Filed: Jul. 27, 2017

(65) Prior Publication Data

US 2018/0087028 A1 Mar. 29, 2018

(30) Foreign Application Priority Data

Jul. 28, 2016 (KR) ........................ 10-2016-0096469

(51) Int. Cl.

| | |
|---|---|
| ***C12N 5/00*** | (2006.01) |
| ***C12N 5/071*** | (2010.01) |
| ***C12N 15/85*** | (2006.01) |
| ***A61P 1/16*** | (2006.01) |
| ***A61K 35/407*** | (2015.01) |
| ***C12N 15/86*** | (2006.01) |
| *G01N 33/50* | (2006.01) |

(52) U.S. Cl.

CPC ............ *C12N 5/067* (2013.01); *A61K 35/407* (2013.01); *A61P 1/16* (2018.01); *C12N 5/0672* (2013.01); *C12N 15/85* (2013.01); *C12N 15/86* (2013.01); *C12N 2501/237* (2013.01); *C12N 2501/38* (2013.01); *C12N 2501/60* (2013.01); *C12N 2501/603* (2013.01); *C12N 2503/02* (2013.01); *C12N 2506/1307* (2013.01); *C12N 2506/14* (2013.01); *C12N 2510/00* (2013.01); *C12N 2740/15043* (2013.01); *G01N 33/5067* (2013.01); *G01N 33/5073* (2013.01)

(58) Field of Classification Search

CPC ............................ C12N 5/067; C12N 2501/60

See application file for complete search history.

(56) References Cited

U.S. PATENT DOCUMENTS

| | | | | |
|---|---|---|---|---|
| 2013/0071365 A1* | 3/2013 | Suzuki | C12N 5/067 424/93.21 |
| 2015/0376570 A1* | 12/2015 | Simeonov et al. | C12N 5/067 |

FOREIGN PATENT DOCUMENTS

| | | |
|---|---|---|
| KR | 10-2016-0034176 | 3/2016 |

OTHER PUBLICATIONS

Wong, Man Sze, “Direct lineage conversion of fibroblasts to hepatocyte-like cells”, Thesis at Graduate School of UNIST, Ulsan, Republic of Korea, Jul. 15, 2015, pp. 1-50. (Year: 2015).*

Serrano et al. “Silencing of hepatic fate-conversion factors induce tumorigenesis in reprogrammed hepatic progenitor-like cells”, Stem Cell Research & Therapy 7:96, Jul. 27, 2016, pp. 1-15. (Year: 2016).*

Lim et al. “Small Molecules Facilitate Single Factor-Mediated Hepatic Reprogramming” Cell Reports 15, 814-829, Apr. 2016. (Year: 2016).*

Ma et al. “Progress in the Reprogramming of Somatic Cells” Circulation Research, vol. 112, Issue 3, Jan. 2013, pp. 562-574. (Year: 2013).*

Zhu et al. “Reprogramming fibroblasts toward cardiomyocytes, neural stem cells and hepatocytes by cell activation and signaling-directed lineage conversion”, Nature Protocol, vol. 10 No. 7, pp. 959-973 (published: Jun. 2015). (Year: 2015).*

Pei et al. “NR4A orphan nuclear receptors are transcriptional regulators of hepatic glucose metabolism” Nat Med. 2006, 12(9):1048-55. (Year: 2006).*

Hu et al. “Accelerated Partial Hepatectomye-Induced Liver Cell Proliferation Is Associated with Liver Injury in Nur77 Knockout Mice” The American Journal of Pathology, vol. 184, No. 12, 3272-3283 (2014). (Year: 2014).*

Theka et al. (2013) “Rapid Generation of Functional Dopaminergic Neurons From Human Induced Pluripotent Stem Cells Through a Single-Step Procedure Using Cell Lineage Transcription Factors” Stem Cells Translational Medicine, 2:473-479. (Year: 2013).*

Snykers et al. (2009) “In Vitro Differentiation of Embryonic and Adult Stem Cells into Hepatocytes: State of the Art” Stem Cells, 27:577-605. (Year: 2009).*

Dianat et al. (2014) “Generation of Functional Cholangiocyte-Like Cells from Human Pluripotent Stem Cells and HepaRG Cells” Hepatology, vol. 60, No. 2, p. 700-714. (Year: 2014).*

Man Sze Wong, “Direct lineage conversion of fibroblasts to hepatocyte-like cells”, Thesis at Graduate School of Unist, Ulsan,Republic of Korea, Jul. 15, 2015, pp. 1-50.

(Continued)

*Primary Examiner* — James D Schultz

*Assistant Examiner* — James Joseph Graber

(74) *Attorney, Agent, or Firm* — Lex IP Meister, PLLC

(57) ABSTRACT

The present invention relates to a composition for inducing direct conversion from a somatic cell into one or more kinds selected from the group consisting of an induced Hepatic stem cell (iHSC), a hepatocyte, and a cholangiocyte, and a method of direct conversion of a somatic cell into one or more kinds selected from the group consisting of an induced Hepatic stem cell, a hepatocyte, and a cholangiocyte.

5 Claims, 24 Drawing Sheets

Specification includes a Sequence Listing.

(56) References Cited

OTHER PUBLICATIONS

Felipe Serrano et al., “Silencing of hepatic fate-conversion factors induce tumorigenesis in reprogrammed hepatic progenitor-like cells” Stem Cell Research & Therapy 7:96, Jul. 27, 2016.

Man Sze Wong, “Direct lineage conversion of fibroblasts to hepatocyte-like cells”, Thesis at Graduate School of Unist, Ulsan,Republic of Korea, Aug. 7, 2015, pp. 1-50.

* cited by examiner

SEQUENCE LISTING

```
<160> NUMBER OF SEQ ID NOS: 96

<210> SEQ ID NO 1
<211> LENGTH: 22
<212> TYPE: DNA
<213> ORGANISM: Artificial Sequence
<220> FEATURE:
<223> OTHER INFORMATION: Gata4_F

<400> SEQUENCE: 1

gacaccccaa tctcgatatg tt                                              22


<210> SEQ ID NO 2
```

<211> LENGTH: 19
<212> TYPE: DNA
<213> ORGANISM: Artificial Sequence
<220> FEATURE:
<223> OTHER INFORMATION: Gata4_R

<400> SEQUENCE: 2
ggacctgctg gcgtcttag 19

<210> SEQ ID NO 3
<211> LENGTH: 20
<212> TYPE: DNA
<213> ORGANISM: Artificial Sequence
<220> FEATURE:
<223> OTHER INFORMATION: Foxa2_F

<400> SEQUENCE: 3
cacctgagtc cgagtctgag 20

<210> SEQ ID NO 4
<211> LENGTH: 20
<212> TYPE: DNA
<213> ORGANISM: Artificial Sequence
<220> FEATURE:
<223> OTHER INFORMATION: Foxa2_R

<400> SEQUENCE: 4
aaggagagag agtggcggat 20

<210> SEQ ID NO 5
<211> LENGTH: 19
<212> TYPE: DNA
<213> ORGANISM: Artificial Sequence
<220> FEATURE:
<223> OTHER INFORMATION: Gata6_F

<400> SEQUENCE: 5
gtgaactgcg gctccatcc 19

<210> SEQ ID NO 6
<211> LENGTH: 19
<212> TYPE: DNA
<213> ORGANISM: Artificial Sequence
<220> FEATURE:
<223> OTHER INFORMATION: Gata6_R

<400> SEQUENCE: 6
tgatgcccct acccctgag 19

<210> SEQ ID NO 7
<211> LENGTH: 21
<212> TYPE: DNA
<213> ORGANISM: Artificial Sequence
<220> FEATURE:
<223> OTHER INFORMATION: Hnf4a_F

<400> SEQUENCE: 7
aggcaatgac tacatcgtcc c 21

<210> SEQ ID NO 8
<211> LENGTH: 20
<212> TYPE: DNA
<213> ORGANISM: Artificial Sequence
<220> FEATURE:
<223> OTHER INFORMATION: Hnf4a_R

<400> SEQUENCE: 8

```
cagaccctcc gagaagcatc                                                   20


<210> SEQ ID NO 9
<211> LENGTH: 19
<212> TYPE: DNA
<213> ORGANISM: Artificial Sequence
<220> FEATURE:
<223> OTHER INFORMATION: EpCam_F

<400> SEQUENCE: 9

ggtgaatgcc agtgtactt                                                    19


<210> SEQ ID NO 10
<211> LENGTH: 21
<212> TYPE: DNA
<213> ORGANISM: Artificial Sequence
<220> FEATURE:
<223> OTHER INFORMATION: EpCam_R

<400> SEQUENCE: 10

caatgatgat ccagtaggtc c                                                 21


<210> SEQ ID NO 11
<211> LENGTH: 21
<212> TYPE: DNA
<213> ORGANISM: Artificial Sequence
<220> FEATURE:
<223> OTHER INFORMATION: Ecad_F

<400> SEQUENCE: 11

gcaggtctcc tcatggcttt g                                                 21


<210> SEQ ID NO 12
<211> LENGTH: 21
<212> TYPE: DNA
<213> ORGANISM: Artificial Sequence
<220> FEATURE:
<223> OTHER INFORMATION: Ecad_R

<400> SEQUENCE: 12

ttggattcag aggcagggtc g                                                 21


<210> SEQ ID NO 13
<211> LENGTH: 19
<212> TYPE: DNA
<213> ORGANISM: Artificial Sequence
<220> FEATURE:
<223> OTHER INFORMATION: Dlk1_F

<400> SEQUENCE: 13

gcacctatgg ggctgaatg                                                    19


<210> SEQ ID NO 14
<211> LENGTH: 19
<212> TYPE: DNA
<213> ORGANISM: Artificial Sequence
<220> FEATURE:
<223> OTHER INFORMATION: Dlk1_R

<400> SEQUENCE: 14

ggcagggaga accattgat                                                    19


<210> SEQ ID NO 15
<211> LENGTH: 21
<212> TYPE: DNA
```

<213> ORGANISM: Artificial Sequence
<220> FEATURE:
<223> OTHER INFORMATION: Oc2_F

<400> SEQUENCE: 15
gctacaccac gccatgagta t 21

<210> SEQ ID NO 16
<211> LENGTH: 19
<212> TYPE: DNA
<213> ORGANISM: Artificial Sequence
<220> FEATURE:
<223> OTHER INFORMATION: Oc2_R

<400> SEQUENCE: 16
tggggctgag cattttgtc 19

<210> SEQ ID NO 17
<211> LENGTH: 21
<212> TYPE: DNA
<213> ORGANISM: Artificial Sequence
<220> FEATURE:
<223> OTHER INFORMATION: Alb_F

<400> SEQUENCE: 17
tgaagttgcc agaagacatc c 21

<210> SEQ ID NO 18
<211> LENGTH: 21
<212> TYPE: DNA
<213> ORGANISM: Artificial Sequence
<220> FEATURE:
<223> OTHER INFORMATION: Alb_R

<400> SEQUENCE: 18
caagttccgc cctgtcatct g 21

<210> SEQ ID NO 19
<211> LENGTH: 21
<212> TYPE: DNA
<213> ORGANISM: Artificial Sequence
<220> FEATURE:
<223> OTHER INFORMATION: Ttr_F

<400> SEQUENCE: 19
gcttcccttc gactcttcct c 21

<210> SEQ ID NO 20
<211> LENGTH: 21
<212> TYPE: DNA
<213> ORGANISM: Artificial Sequence
<220> FEATURE:
<223> OTHER INFORMATION: Ttr_R

<400> SEQUENCE: 20
gccaagtgtc ttccagtacg a 21

<210> SEQ ID NO 21
<211> LENGTH: 20
<212> TYPE: DNA
<213> ORGANISM: Artificial Sequence
<220> FEATURE:
<223> OTHER INFORMATION: CK8_F

<400> SEQUENCE: 21
agaaggatgt ggacgaagca 20

<210> SEQ ID NO 22
<211> LENGTH: 20
<212> TYPE: DNA
<213> ORGANISM: Artificial Sequence
<220> FEATURE:
<223> OTHER INFORMATION: CK8_R

<400> SEQUENCE: 22
atctctgtct ttgtgcggcg 20

<210> SEQ ID NO 23
<211> LENGTH: 21
<212> TYPE: DNA
<213> ORGANISM: Artificial Sequence
<220> FEATURE:
<223> OTHER INFORMATION: CK18_F

<400> SEQUENCE: 23
atgaagagga agtccaaggt c 21

<210> SEQ ID NO 24
<211> LENGTH: 21
<212> TYPE: DNA
<213> ORGANISM: Artificial Sequence
<220> FEATURE:
<223> OTHER INFORMATION: CK18_R

<400> SEQUENCE: 24
gttctccaag ttgatgttct g 21

<210> SEQ ID NO 25
<211> LENGTH: 20
<212> TYPE: DNA
<213> ORGANISM: Artificial Sequence
<220> FEATURE:
<223> OTHER INFORMATION: Afp_F

<400> SEQUENCE: 25
gcaggatggg gaaaaagtca 20

<210> SEQ ID NO 26
<211> LENGTH: 21
<212> TYPE: DNA
<213> ORGANISM: Artificial Sequence
<220> FEATURE:
<223> OTHER INFORMATION: Afp_R

<400> SEQUENCE: 26
cctaaggtct ggtagagagc g 21

<210> SEQ ID NO 27
<211> LENGTH: 20
<212> TYPE: DNA
<213> ORGANISM: Artificial Sequence
<220> FEATURE:
<223> OTHER INFORMATION: Afp_R

<400> SEQUENCE: 27
gaccaagaca cagttttcgc 20

<210> SEQ ID NO 28
<211> LENGTH: 20
<212> TYPE: DNA
<213> ORGANISM: Artificial Sequence
<220> FEATURE:

<223> OTHER INFORMATION: Aat_R

<400> SEQUENCE: 28
atctgggcta accttctgcg 20

<210> SEQ ID NO 29
<211> LENGTH: 20
<212> TYPE: DNA
<213> ORGANISM: Artificial Sequence
<220> FEATURE:
<223> OTHER INFORMATION: Tat_F

<400> SEQUENCE: 29
atcggctacc tatccagtcg 20

<210> SEQ ID NO 30
<211> LENGTH: 21
<212> TYPE: DNA
<213> ORGANISM: Artificial Sequence
<220> FEATURE:
<223> OTHER INFORMATION: Tat_R

<400> SEQUENCE: 30
gccactgcca aaatcttctg a 21

<210> SEQ ID NO 31
<211> LENGTH: 23
<212> TYPE: DNA
<213> ORGANISM: Artificial Sequence
<220> FEATURE:
<223> OTHER INFORMATION: G6P_F

<400> SEQUENCE: 31
tcaacctcgt cttcaagtgg att 23

<210> SEQ ID NO 32
<211> LENGTH: 20
<212> TYPE: DNA
<213> ORGANISM: Artificial Sequence
<220> FEATURE:
<223> OTHER INFORMATION: G6P_R

<400> SEQUENCE: 32
cacagcaatg cctgacaaga 20

<210> SEQ ID NO 33
<211> LENGTH: 20
<212> TYPE: DNA
<213> ORGANISM: Artificial Sequence
<220> FEATURE:
<223> OTHER INFORMATION: Cyp7a1_F

<400> SEQUENCE: 33
ggagccctga agcaatgaaa 20

<210> SEQ ID NO 34
<211> LENGTH: 20
<212> TYPE: DNA
<213> ORGANISM: Artificial Sequence
<220> FEATURE:
<223> OTHER INFORMATION: Cyp7a1_R

<400> SEQUENCE: 34
aaaagtcaaa gggtctgggt 20

```
<210> SEQ ID NO 35
<211> LENGTH: 22
<212> TYPE: DNA
<213> ORGANISM: Artificial Sequence
<220> FEATURE:
<223> OTHER INFORMATION: CK7_F

<400> SEQUENCE: 35

ccttcacgag acagagttag ca                                               22


<210> SEQ ID NO 36
<211> LENGTH: 19
<212> TYPE: DNA
<213> ORGANISM: Artificial Sequence
<220> FEATURE:
<223> OTHER INFORMATION: CK7_R

<400> SEQUENCE: 36

acttggcacg ctggttctt                                                   19


<210> SEQ ID NO 37
<211> LENGTH: 21
<212> TYPE: DNA
<213> ORGANISM: Artificial Sequence
<220> FEATURE:
<223> OTHER INFORMATION: CK19_F

<400> SEQUENCE: 37

agtttgagac agaacacgcc t                                                21


<210> SEQ ID NO 38
<211> LENGTH: 18
<212> TYPE: DNA
<213> ORGANISM: Artificial Sequence
<220> FEATURE:
<223> OTHER INFORMATION: CK19_R

<400> SEQUENCE: 38

ctcctcaatc cgagcaag                                                    18


<210> SEQ ID NO 39
<211> LENGTH: 21
<212> TYPE: DNA
<213> ORGANISM: Artificial Sequence
<220> FEATURE:
<223> OTHER INFORMATION: Ggt1_F

<400> SEQUENCE: 39

atctacaaca gcaccacagg a                                                21


<210> SEQ ID NO 40
<211> LENGTH: 21
<212> TYPE: DNA
<213> ORGANISM: Artificial Sequence
<220> FEATURE:
<223> OTHER INFORMATION: Ggt1_R

<400> SEQUENCE: 40

tcaaccgtca taatgccacc a                                                21


<210> SEQ ID NO 41
<211> LENGTH: 24
<212> TYPE: DNA
<213> ORGANISM: Artificial Sequence
<220> FEATURE:
<223> OTHER INFORMATION: Gapdh_F
```

<400> SEQUENCE: 41 acgaccctt cattgacctc aact 24

<210> SEQ ID NO 42
<211> LENGTH: 24
<212> TYPE: DNA
<213> ORGANISM: Artificial Sequence
<220> FEATURE:
<223> OTHER INFORMATION: Gapdh_R

<400> SEQUENCE: 42
atatttctcg tggttcacac ccat 24

<210> SEQ ID NO 43
<211> LENGTH: 21
<212> TYPE: DNA
<213> ORGANISM: Artificial Sequence
<220> FEATURE:
<223> OTHER INFORMATION: Cyp1a2_F

<400> SEQUENCE: 43
ataacttcgt gctgtttctg c 21

<210> SEQ ID NO 44
<211> LENGTH: 20
<212> TYPE: DNA
<213> ORGANISM: Artificial Sequence
<220> FEATURE:
<223> OTHER INFORMATION: Cyp1a2_R

<400> SEQUENCE: 44
accgccattg tctttgtagt 20

<210> SEQ ID NO 45
<211> LENGTH: 19
<212> TYPE: DNA
<213> ORGANISM: Artificial Sequence
<220> FEATURE:
<223> OTHER INFORMATION: Cyp1b1_F

<400> SEQUENCE: 45
attctcagtg ggcaaacgg 19

<210> SEQ ID NO 46
<211> LENGTH: 21
<212> TYPE: DNA
<213> ORGANISM: Artificial Sequence
<220> FEATURE:
<223> OTHER INFORMATION: Cyp1b1_R

<400> SEQUENCE: 46
ggattctaaa cgacttgggc t 21

<210> SEQ ID NO 47
<211> LENGTH: 20
<212> TYPE: DNA
<213> ORGANISM: Artificial Sequence
<220> FEATURE:
<223> OTHER INFORMATION: Cyp2b10_F

<400> SEQUENCE: 47
ctgtcgttga gccaaccttc 20

<210> SEQ ID NO 48
<211> LENGTH: 20

<212> TYPE: DNA
<213> ORGANISM: Artificial Sequence
<220> FEATURE:
<223> OTHER INFORMATION: Cyp2b10_R

<400> SEQUENCE: 48
tccgcagttc ctccactaaa 20

<210> SEQ ID NO 49
<211> LENGTH: 22
<212> TYPE: DNA
<213> ORGANISM: Artificial Sequence
<220> FEATURE:
<223> OTHER INFORMATION: Cyp2c37_F

<400> SEQUENCE: 49
tgtggaggaa cttaggaaaa cc 22

<210> SEQ ID NO 50
<211> LENGTH: 21
<212> TYPE: DNA
<213> ORGANISM: Artificial Sequence
<220> FEATURE:
<223> OTHER INFORMATION: Cyp2c37_R

<400> SEQUENCE: 50
agggctgctc agaatctttg t 21

<210> SEQ ID NO 51
<211> LENGTH: 20
<212> TYPE: DNA
<213> ORGANISM: Artificial Sequence
<220> FEATURE:
<223> OTHER INFORMATION: Cyp2d22_F

<400> SEQUENCE: 51
gccttcatgc cattctcagc 20

<210> SEQ ID NO 52
<211> LENGTH: 18
<212> TYPE: DNA
<213> ORGANISM: Artificial Sequence
<220> FEATURE:
<223> OTHER INFORMATION: Cyp2d22_R

<400> SEQUENCE: 52
cagagcccta aagacgcc 18

<210> SEQ ID NO 53
<211> LENGTH: 21
<212> TYPE: DNA
<213> ORGANISM: Artificial Sequence
<220> FEATURE:
<223> OTHER INFORMATION: Cyp2e1_F

<400> SEQUENCE: 53
ggaatgggga aacagggtaa t 21

<210> SEQ ID NO 54
<211> LENGTH: 20
<212> TYPE: DNA
<213> ORGANISM: Artificial Sequence
<220> FEATURE:
<223> OTHER INFORMATION: Cyp2e1_R

<400> SEQUENCE: 54
gcacagccaa tcagaaaggt 20

<210> SEQ ID NO 55
<211> LENGTH: 22
<212> TYPE: DNA
<213> ORGANISM: Artificial Sequence
<220> FEATURE:
<223> OTHER INFORMATION: Cyp3a11_F

<400> SEQUENCE: 55
tgggactcgt aaacatgaac tt 22

<210> SEQ ID NO 56
<211> LENGTH: 20
<212> TYPE: DNA
<213> ORGANISM: Artificial Sequence
<220> FEATURE:
<223> OTHER INFORMATION: Cyp3a11_R

<400> SEQUENCE: 56
ttgaccatca aacaaccccc 20

<210> SEQ ID NO 57
<211> LENGTH: 20
<212> TYPE: DNA
<213> ORGANISM: Artificial Sequence
<220> FEATURE:
<223> OTHER INFORMATION: Cyp3a13_F

<400> SEQUENCE: 57
ggggacgatt cttgcttacc 20

<210> SEQ ID NO 58
<211> LENGTH: 21
<212> TYPE: DNA
<213> ORGANISM: Artificial Sequence
<220> FEATURE:
<223> OTHER INFORMATION: Cyp3a13_R

<400> SEQUENCE: 58
aaatacccac tggaccaaag c 21

<210> SEQ ID NO 59
<211> LENGTH: 20
<212> TYPE: DNA
<213> ORGANISM: Artificial Sequence
<220> FEATURE:
<223> OTHER INFORMATION: hCOLIA2-qF

<400> SEQUENCE: 59
cagagtggag cagtggttac 20

<210> SEQ ID NO 60
<211> LENGTH: 20
<212> TYPE: DNA
<213> ORGANISM: Artificial Sequence
<220> FEATURE:
<223> OTHER INFORMATION: hCOLIA2-qR

<400> SEQUENCE: 60
cagttcttgg ctgggatgtt 20

<210> SEQ ID NO 61
<211> LENGTH: 18
<212> TYPE: DNA
<213> ORGANISM: Artificial Sequence
<220> FEATURE:
<223> OTHER INFORMATION: hTWIST2-qF

<400> SEQUENCE: 61
cctcagctac gccttctc 18

<210> SEQ ID NO 62
<211> LENGTH: 22
<212> TYPE: DNA
<213> ORGANISM: Artificial Sequence
<220> FEATURE:
<223> OTHER INFORMATION: hTWIST2-qR

<400> SEQUENCE: 62
gaatgcatcc caattccact tg 22

<210> SEQ ID NO 63
<211> LENGTH: 22
<212> TYPE: DNA
<213> ORGANISM: Artificial Sequence
<220> FEATURE:
<223> OTHER INFORMATION: hALB-qF

<400> SEQUENCE: 63
gcacagaatc cttggtgaac ag 22

<210> SEQ ID NO 64
<211> LENGTH: 22
<212> TYPE: DNA
<213> ORGANISM: Artificial Sequence
<220> FEATURE:
<223> OTHER INFORMATION: hALB-qR

<400> SEQUENCE: 64
atggaaggtg aatgtttcag ca 22

<210> SEQ ID NO 65
<211> LENGTH: 20
<212> TYPE: DNA
<213> ORGANISM: Artificial Sequence
<220> FEATURE:
<223> OTHER INFORMATION: hAFP qF

<400> SEQUENCE: 65
gcttggtggt ggatgaaaca 20

<210> SEQ ID NO 66
<211> LENGTH: 23
<212> TYPE: DNA
<213> ORGANISM: Artificial Sequence
<220> FEATURE:
<223> OTHER INFORMATION: hAFP qR

<400> SEQUENCE: 66
tcctctgtta tttgtggctt ttg 23

<210> SEQ ID NO 67
<211> LENGTH: 20
<212> TYPE: DNA
<213> ORGANISM: Artificial Sequence
<220> FEATURE:
<223> OTHER INFORMATION: hHNF4a qF

<400> SEQUENCE: 67
tcgcagatgt gtgtgagtcc 20

<210> SEQ ID NO 68
<211> LENGTH: 20
<212> TYPE: DNA
<213> ORGANISM: Artificial Sequence
<220> FEATURE:
<223> OTHER INFORMATION: hHNF4a qR

<400> SEQUENCE: 68
cactcaacga gaaccagcag 20

<210> SEQ ID NO 69
<211> LENGTH: 20
<212> TYPE: DNA
<213> ORGANISM: Artificial Sequence
<220> FEATURE:
<223> OTHER INFORMATION: hFOXA2 qF

<400> SEQUENCE: 69
accactacgc cttcaaccac 20

<210> SEQ ID NO 70
<211> LENGTH: 20
<212> TYPE: DNA
<213> ORGANISM: Artificial Sequence
<220> FEATURE:
<223> OTHER INFORMATION: hFOXA2 qR

<400> SEQUENCE: 70
gccttgaggt ccattttgtg 20

<210> SEQ ID NO 71
<211> LENGTH: 20
<212> TYPE: DNA
<213> ORGANISM: Artificial Sequence
<220> FEATURE:
<223> OTHER INFORMATION: hGAPDH R

<400> SEQUENCE: 71
ggaggagtgg gtgtcgctgt 20

<210> SEQ ID NO 72
<211> LENGTH: 20
<212> TYPE: DNA
<213> ORGANISM: Artificial Sequence
<220> FEATURE:
<223> OTHER INFORMATION: hGAPDH F

<400> SEQUENCE: 72
gtggacctga cctgccgtct 20

<210> SEQ ID NO 73
<211> LENGTH: 1430
<212> TYPE: DNA
<213> ORGANISM: Homo sapiens

<400> SEQUENCE: 73
agagaggggt tgagtagtcc cttcgcaagc cctcatttca ccaggccccc ggcttggggc 60
gccttccttc cccatggcgg gacacctggc ttcggatttc gccttctcgc cccctccagg 120
tggtggaggt gatgggccag gggggccgga gccgggctgg gttgatcctc ggacctggct 180
aagcttccaa ggccctcctg gagggccagg aatcgggccg ggggttgggc caggctctga 240
ggtgtggggg attcccccat gccccccgcc gtatgagttc tgtgggggga tggcgtactg 300
tgggccccag gttggagtgg ggctagtgcc ccaaggcggc ttggagacct ctcagcctga 360

```
gggcgaagca ggagtcgggg tggagagcaa ctccgatggg gcctccccgg agccctgcac    420

cgtcacccct ggtgccgtga agctggagaa ggagaagctg gagcaaaacc cggaggagtc    480

ccaggacatc aaagctctgc agaaagaact cgagcaattt gccaagctcc tgaagcagaa    540

gaggatcacc ctgggatata cacaggccga tgtggggctc accctggggg ttctatttgg    600

gaaggtattc agccaaacga ccatctgccg ctttgaggct ctgcagctta gcttcaagaa    660

catgtgtaag ctgcggccct tgctgcagaa gtgggtggag gaagctgaca acaatgaaaa    720

tcttcaggag atatgcaaag cagaaaccct cgtgcaggcc cgaaagagaa agcgaaccag    780

tatcgagaac cgagtgagag gcaacctgga gaatttgttc ctgcagtgcc cgaaacccac    840

actgcagcag atcagccaca tcgcccagca gcttgggctc gagaaggatg tggtccgagt    900

gtggttctgt aaccggcgcc agaagggcaa gcgatcaagc agcgactatg cacaacgaga    960

ggattttgag gctgctgggt ctcctttctc agggggacca gtgtcctttc ctctggcccc   1020

agggccccat tttggtaccc caggctatgg gagccctcac ttcactgcac tgtactcctc   1080

ggtccctttc cctgaggggg aagcctttcc ccctgtctcc gtcaccactc tgggctctcc   1140

catgcattca aactgaggtg cctgcccttc taggaatggg ggacaggggg aggggaggag   1200

ctagggaaag aaaacctgga gtttgtgcca gggtttttgg gattaagttc ttcattcact   1260

aaggaaggaa ttgggaacac aaagggtggg ggcaggggag tttggggcaa ctggttggag   1320

ggaaggtgaa gttcaatgat gctcttgatt ttaatcccac atcatgtatc actttttttct   1380

taaataaaga agcctgggac acagtagata gacacactta aaaaaaaaaa              1430
```

```
<210> SEQ ID NO 74
<211> LENGTH: 360
<212> TYPE: PRT
<213> ORGANISM: Homo sapiens

<400> SEQUENCE: 74

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
```

-continued 180 185 190

Ser Phe Lys Asn Met Cys Lys Leu Arg Pro Leu Leu Gln Lys Trp Val
195 200 205

Glu Glu Ala Asp Asn Asn Glu Asn Leu Gln Glu Ile Cys Lys Ala Glu
210 215 220

Thr Leu Val Gln Ala Arg Lys Arg Lys Arg Thr Ser Ile Glu Asn Arg
225 230 235 240

Val Arg Gly Asn Leu Glu Asn Leu Phe Leu Gln Cys Pro Lys Pro Thr
245 250 255

Leu Gln Gln Ile Ser His Ile Ala Gln Gln Leu Gly Leu Glu Lys Asp
260 265 270

Val Val Arg Val Trp Phe Cys Asn Arg Arg Gln Lys Gly Lys Arg Ser
275 280 285

Ser Ser Asp Tyr Ala Gln Arg Glu Asp Phe Glu Ala Ala Gly Ser Pro
290 295 300

Phe Ser Gly Gly Pro Val Ser Phe Pro Leu Ala Pro Gly Pro His Phe
305 310 315 320

Gly Thr Pro Gly Tyr Gly Ser Pro His Phe Thr Ala Leu Tyr Ser Ser
325 330 335

Val Pro Phe Pro Glu Gly Glu Ala Phe Pro Pro Val Ser Val Thr Thr
340 345 350

Leu Gly Ser Pro Met His Ser Asn
355 360

<210> SEQ ID NO 75
<211> LENGTH: 4737
<212> TYPE: DNA
<213> ORGANISM: Homo sapiens

<400> SEQUENCE: 75
ggtttgaaag gaaggcagag agggcactgg gaggaggcag tgggagggcg gagggcgggg 60
gccttcgggg tgggcgccca gggtagggca ggtggccgcg gcgtggaggc agggagaatg 120
cgactctcca aaaccctcgt cgacatggac atggccgact acagtgctgc actggaccca 180
gcctacacca ccctggaatt tgagaatgtg caggtgttga cgatgggcaa tgacacgtcc 240
ccatcagaag gcaccaacct caacgcgccc aacagcctgg gtgtcagcgc cctgtgtgcc 300
atctgcgggg accgggccac gggcaaacac tacggtgcct cgagctgtga cggctgcaag 360
ggcttcttcc ggaggagcgt gcggaagaac cacatgtact cctgcagatt tagccggcag 420
tgcgtggtgg acaaagacaa gaggaaccag tgccgctact gcaggctcaa gaaatgcttc 480
cgggctggca tgaagaagga agccgtccag aatgagcggg accggatcag cactcgaagg 540
tcaagctatg aggacagcag cctgccctcc atcaatgcgc tcctgcaggc ggaggtcctg 600
tcccgacaga tcacctcccc cgtctccggg atcaacggcg acattcgggc gaagaagatt 660
gccagcatcg cagatgtgtg tgagtccatg aaggagcagc tgctggttct cgttgagtgg 720
gccaagtaca tcccagcttt ctgcgagctc cccctggacg accaggtggc cctgctcaga 780
gcccatgctg gcgagcacct gctgctcgga gccaccaaga gatccatggt gttcaaggac 840
gtgctgctcc taggcaatga ctacattgtc cctcggcact gcccggagct ggcggagatg 900
agccgggtgt ccatacgcat ccttgacgag ctggtgctgc ccttccagga gctgcagatc 960
gatgacaatg agtatgccta cctcaaagcc atcatcttct ttgacccaga tgccaagggg 1020
ctgagcgatc cagggaagat caagcggctg cgttcccagg tgcaggtgag cttggaggac 1080

-continued

```
tacatcaacg accgccagta tgactcgcgt ggccgctttg gagagctgct gctgctgctg   1140
cccaccttgc agagcatcac ctggcagatg atcgagcaga tccagttcat caagctcttc   1200
ggcatggcca agattgacaa cctgttgcag gagatgctgc tgggagggtc ccccagcgat   1260
gcaccccatg cccaccaccc cctgcaccct cacctgatgc aggaacatat gggaaccaac   1320
gtcatcgttg ccaacacaat gcccactcac ctcagcaacg gacagatgtg tgagtggccc   1380
cgacccaggg gacaggcagc cacccctgag accccacagc cctcaccgcc aggtggctca   1440
gggtctgagc cctataagct cctgccggga gccgtcgcca caatcgtcaa gcccctctct   1500
gccatccccc agccgaccat caccaagcag gaagttatct agcaagccgc tggggcttgg   1560
gggctccact ggctccccc agcccccctaa gagagcacct ggtgatcacg tggtcacggc   1620
aaaggaagac gtgatgccag gaccagtccc agagcaggaa tgggaaggat gaagggcccg   1680
agaacatggc ctaagggcca catcccactg ccacccttga cgccctgctc tggataacaa   1740
gactttgact tggggagacc tctactgcct tggacaactt ttctcatgtt gaagccactg   1800
ccttcacctt caccttcatc catgtccaac ccccgacttc atcccaaagg acagccgcct   1860
ggagatgact tgaggcctta cttaaaccca gctcccttct tccctagcct ggtgcttctc   1920
ctctcctagc ccctgtcatg gtgtccagac agagccctgt gaggctgggt ccaattgtgg   1980
cacttggggc accttgctcc tccttctgct gctgccccca cctctgctgc ctccctctgc   2040
tgtcaccttg ctcagccatc ccgtcttctc caacaccacc tctccagagg ccaaggaggc   2100
cttggaaacg attcccccag tcattctggg aacatgttgt aagcactgac tgggaccagg   2160
caccaggcag ggtctagaag gctgtggtga gggaagacgc ctttctcctc caacccaacc   2220
tcatcctcct tcttcaggga cttgggtggg tacttgggtg aggatccctg aaggccttca   2280
acccgagaaa acaaacccag gttggcgact gcaacaggaa cttggagtgg agaggaaaag   2340
catcagaaag aggcagacca tccaccaggc ctttgagaaa gggtagaatt ctggctggta   2400
gagcaggtga gatgggacat tccaaagaac agcctgagcc aaggcctagt ggtagtaaga   2460
atctagcaag aattgaggaa gaatggtgtg ggagagggat gatgaagaga gagagggcct   2520
gctggagagc atagggtctg gaacaccagg ctgaggtcct gatcagcttc aaggagtatg   2580
cagggagctg ggcttccaga aaatgaacac agcagttctg cagaggacgg gaggctggaa   2640
gctgggaggt caggtggggt ggatgatata atgcgggtga gagtaatgag gcttggggct   2700
ggagaggaca agatgggtaa accctcacat cagagtgaca tccaggagga ataagctccc   2760
agggcctgtc tcaagctctt ccttactccc aggcactgtc ttaaggcatc tgacatgcat   2820
catctcattt aatcctccct tcctccctat taacctagag attgtttttg tttttttattc   2880
tcctcctccc tccccgccct cacccgcccc actccctcct aacctagaga ttgttacaga   2940
agctgaaatt gcgttctaag aggtgaagtg atttttttttc tgaaactcac acaactagga   3000
agtggctgag tcaggacttg aacccaggtc tccctggatc agaacaggag ctcttaacta   3060
cagtggctga atagcttctc caaaggctcc ctgtgttctc accgtgatca agttgagggg   3120
cttccggctc ccttctacag cctcagaaac cagactcgtt cttctgggaa ccctgcccac   3180
tcccaggacc aagattggcc tgaggctgca ctaaaattca cttagggtcg agcatcctgt   3240
ttgctgataa atattaagga gaattcatga ctcttgacag cttttctctc ttcactcccc   3300
aagtcaaggg gaggggtggc aggggtctgt ttcctggaag tcaggctcat ctggcctgtt   3360
ggcatggggg tgggacagtg tgcacagtgt gggggcaggg gagggctaag caggcctggg   3420
tttgagggct gctccggaga ccgtcactcc aggtgcattc tggaagcatt agaccccagg   3480
```

```
atggagcgac cagcatgtca tccatgtgga atcttggtgg ctttgaggac attctggaaa   3540

atgccactga ccagtgtgaa caaaagggat gtgttatggg gctggaggtg tgattaggta   3600

ggagggaaac tgttggaccg actcctgccc cctgctcaac actgacccct ctgagtggtt   3660

ggaggcagtg ccccagtgcc cagaaatccc accattagtg attgtttttt atgagaaaga   3720

ggcgtggaga agtattgggg caatgtgtca gggaggaatc accacatccc tacggcagtc   3780

ccagccaagc cccaatccc agcggagact gtgccctgct cagagctccc aagccttccc   3840

ccaccacctc actcaagtgc ccctgaaatc cctgccagac ggctcagcct ggtctgcggt   3900

aaggcaggga ggctggaacc atttctgggc attgtggtca ttcccactgt gttcctccac   3960

ctcctccctc cagcgttgct cagacctctg tcttgggaga aaggttgaga taagaatgtc   4020

ccatggagtg ccgtgggcaa cagtggccct tcatgggaac aatctgttgg agcagggggt   4080

cagttctctg ctgggaatct acccctttct ggaggagaaa cccattccac cttaataact   4140

ttattgtaat gtgagaaaca caaaacaaag tttacttttt tgactctaag ctgacatgat   4200

attagaaaat ctctcgctct cttttttttt tttttttttt tttttggcta cttgagttgt   4260

ggtcctaaaa cataaaatct gatggacaaa cagagggttg ctggggggac aagcgtgggc   4320

acaatttccc caccaagaca ccctgatctt caggcgggtc tcaggagctt ctaaaaatcc   4380

gcatggctct cctgagagtg gacagaggag aggagagggt cagaaatgaa cgctcttcta   4440

tttcttgtca ttaccaagcc aattactttt gccaaatttt tctgtgatct gccctgatta   4500

agatgaattg tgaaatttac atcaagcaat tatcaaagcg ggctgggtcc catcagaacg   4560

acccacatct ttctgtgggt gtgaatgtca ttaggtcttg cgctgacccc tgagccccca   4620

tcactgccgc ctgatggggc aaagaaacaa aaaacatttc ttactcttct gtgttttaac   4680

aaaagtttat aaaacaaaat aaatggcgca tatgttttct aaaaaaaaaa aaaaaaa      4737
```

<210> SEQ ID NO 76
<211> LENGTH: 474
<212> TYPE: PRT
<213> ORGANISM: Homo sapiens

<400> SEQUENCE: 76

```
Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Thr Asn Leu
        35                  40                  45

Asn Ala Pro Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
```

145 150 155 160

Leu Ser Arg Gln Ile Thr Ser Pro Val Ser Gly Ile Asn Gly Asp Ile
165 170 175

Arg Ala Lys Lys Ile Ala Ser Ile Ala Asp Val Cys Glu Ser Met Lys
180 185 190

Glu Gln Leu Leu Val Leu Val Glu Trp Ala Lys Tyr Ile Pro Ala Phe
195 200 205

Cys Glu Leu Pro Leu Asp Asp Gln Val Ala Leu Leu Arg Ala His Ala
210 215 220

Gly Glu His Leu Leu Leu Gly Ala Thr Lys Arg Ser Met Val Phe Lys
225 230 235 240

Asp Val Leu Leu Leu Gly Asn Asp Tyr Ile Val Pro Arg His Cys Pro
245 250 255

Glu Leu Ala Glu Met Ser Arg Val Ser Ile Arg Ile Leu Asp Glu Leu
260 265 270

Val Leu Pro Phe Gln Glu Leu Gln Ile Asp Asp Asn Glu Tyr Ala Tyr
275 280 285

Leu Lys Ala Ile Ile Phe Phe Asp Pro Asp Ala Lys Gly Leu Ser Asp
290 295 300

Pro Gly Lys Ile Lys Arg Leu Arg Ser Gln Val Gln Val Ser Leu Glu
305 310 315 320

Asp Tyr Ile Asn Asp Arg Gln Tyr Asp Ser Arg Gly Arg Phe Gly Glu
325 330 335

Leu Leu Leu Leu Leu Pro Thr Leu Gln Ser Ile Thr Trp Gln Met Ile
340 345 350

Glu Gln Ile Gln Phe Ile Lys Leu Phe Gly Met Ala Lys Ile Asp Asn
355 360 365

Leu Leu Gln Glu Met Leu Leu Gly Gly Ser Pro Ser Asp Ala Pro His
370 375 380

Ala His His Pro Leu His Pro His Leu Met Gln Glu His Met Gly Thr
385 390 395 400

Asn Val Ile Val Ala Asn Thr Met Pro Thr His Leu Ser Asn Gly Gln
405 410 415

Met Cys Glu Trp Pro Arg Pro Arg Gly Gln Ala Ala Thr Pro Glu Thr
420 425 430

Pro Gln Pro Ser Pro Pro Gly Gly Ser Gly Ser Glu Pro Tyr Lys Leu
435 440 445

Leu Pro Gly Ala Val Ala Thr Ile Val Lys Pro Leu Ser Ala Ile Pro
450 455 460

Gln Pro Thr Ile Thr Lys Gln Glu Val Ile
465 470

<210> SEQ ID NO 77
<211> LENGTH: 3546
<212> TYPE: DNA
<213> ORGANISM: Homo sapiens

<400> SEQUENCE: 77
gctgacgcgc gctgacgcgc ggagacttta ggtgcatgtt ggcagcggca gcgcaagcca 60
cataaacaaa ggcacattgg cggccagggc cagtccgccc ggcggctcgc gcacggctcc 120
gcggtccctt ttgcctgtcc agccggccgc ctgtccctgc tccctccctc cgtgaggtgt 180
ccgggttccc ttcgcccagc tctcccaccc ctacccgacc ccggcgcccg ggctcccaga 240
gggaactgca cttcggcaga gttgaatgaa tgaagagaga cgcggagaac tcctaaggag 300

```
gagattggac aggctggact ccccattgct tttctaaaaa tcttggaaac tttgtccttc    360
attgaattac gacactgtcc acctttaatt tcctcgaaaa cgcctgtaac tcggctgaag    420
ccatgccttg tgttcaggcg cagtatgggt cctcgcctca aggagccagc cccgcttctc    480
agagctacag ttaccactct tcgggagaat acagctccga tttcttaact ccagagtttg    540
tcaagtttag catggacctc accaacactg aaatcactgc caccacttct ctccccagct    600
tcagtacctt tatggacaac tacagcacag gctacgacgt caagccacct tgcttgtacc    660
aaatgcccct gtccggacag cagtcctcca ttaaggtaga agacattcag atgcacaact    720
accagcaaca cagccacctg cccccccagt ctgaggagat gatgccgcac tccgggtcgg    780
tttactacaa gccctcctcg cccccgacgc ccaccacccc gggcttccag gtgcagcaca    840
gccccatgtg ggacgacccg ggatctctcc acaacttcca ccagaactac gtggccacta    900
cgcacatgat cgagcagagg aaaacgccag tctcccgcct ctccctcttc tcctttaagc    960
aatcgccccc tggcaccccg gtgtctagtt gccagatgcg cttcgacggg cccctgcacg   1020
tccccatgaa cccggagccc gccggcagcc accacgtggt ggacgggcag accttcgctg   1080
tgcccaaccc cattcgcaag cccgcgtcca tgggcttccc gggcctgcag atcggccacg   1140
cgtctcagct gctcgacacg caggtgccct caccgccgtc gcggggctcc ccctccaacg   1200
aggggctgtg cgctgtgtgt ggggacaacg cggcctgcca acactacggc gtgcgcacct   1260
gtgagggctg caaaggcttc tttaagcgca cagtgcaaaa aaatgcaaaa tacgtgtgtt   1320
tagcaaataa aaactgccca gtggacaagc gtcgccggaa tcgctgtcag tactgccgat   1380
ttcagaagtg cctggctgtt gggatggtca aagaagtggt tcgcacagac agtttaaaag   1440
gccggagagg tcgtttgccc tcgaaaccga agagcccaca ggagccctct ccccccttcgc  1500
ccccggtgag tctgatcagt gccctcgtca gggcccatgt cgactccaac ccggctatga   1560
ccagcctgga ctattccagg ttccaggcga accctgacta tcaaatgagt ggagatgaca   1620
cccagcatat ccagcaattc tatgatctcc tgactggctc catggagatc atccggggct   1680
gggcagagaa gatccctggc ttcgcagacc tgcccaaagc cgaccaagac ctgctttttg   1740
aatcagcttt cttagaactg tttgtccttc gattagcata caggtccaac ccagtggagg   1800
gtaaactcat cttttgcaat ggggtggtct tgcacaggtt gcaatgcgtt cgtggctttg   1860
gggaatggat tgattccatt gttgaattct cctccaactt gcagaatatg aacatcgaca   1920
tttctgcctt ctcctgcatt gctgccctgg ctatggtcac agagagacac gggctcaagg   1980
aacccaagag agtggaagaa ctgcaaaaca agattgtaaa ttgtctcaaa gaccacgtga   2040
ctttcaacaa tgggggggttg aaccgcccca attatttgtc caaactgttg gggaagctcc   2100
cagaacttcg taccctttgc acacaggggc tacagcgcat ttctacctg aaattggaag    2160
acttggtgcc accgccagca ataattgaca aacttttcct ggacacttta cctttctaag   2220
acctcctccc aagcacttca aaggaactgg aatgataatg gaaactgtca agaggggggca  2280
agtcacatgg gcagagatag ccgtgtgagc agtctcagct caagctgccc cccatttctg   2340
taaccctcct agccccttg atccctaaag aaaacaaaca aacaaacaaa aactgttgct    2400
atttcctaac ctgcaggcag aacctgaaag ggcattttgg ctccggggca tcctggattt   2460
agaacatgga ctacacacaa tacagtggta taaacttttt attctcagtt taaaaatcag   2520
tttgttgttc agaagaaaga ttgctataat gtataatggg aaatgtttgg ccatgcttgg   2580
ttgttgcagt tcagacaaat gtaacacaca cacacataca cacacacaca cacacacaga   2640
```

```
gacacatctt aaggggaccc acaagtattg ccctttaaca agacttcaaa gttttctgct   2700

gtaaagaaag ctgtaatata tagtaaaact aaatgttgcg tgggtggcat gagttgaaga   2760

aggcaaaggc ttgtaaattt acccaatgca gtttggcttt ttaaattatt ttgtgcctat   2820

ttatgaataa atattacaaa ttctaaaaga taagtgtgtt tgcaaaaaaa aagaaaataa   2880

atacataaaa aagggacaag catgttgatt ctaggttgaa aatgttatag gcacttgcta   2940

cttcagtaat gtctatatta tataaatagt atttcagaca ctatgtagtc tgttagattt   3000

tataaagatt ggtagttatc tgagcttaaa cattttctca attgtaaaat aggtgggcac   3060

aagtattaca catcagaaaa tcctgacaaa agggacacat agtgtttgta acaccgtcca   3120

acattccttg tttgtaagtg ttgtatgtac cgttgatgtt gataaaaaga aagtttatat   3180

cttgattatt ttgttgtcta aagctaaaca aaacttgcat gcagcagctt ttgactgttt   3240

ccagagtgct tataatatac ataactccct ggaaataact gagcactttg aatttttttt   3300

atgtctaaaa ttgtcagtta atttattatt ttgtttgagt aagaatttta atattgccat   3360

attctgtagt atttttcttt gtatatttct agtatggcac atgatatgag tcactgcctt   3420

tttttctatg gtgtatgaca gttagagatg ctgatttttt ttctgataaa ttctttcttt   3480

gagaaagaca attttaatgt ttacaacaat aaaccatgta aatgaacaga aaaaaaaaaa   3540

aaaaaa                                                              3546
```

```
<210> SEQ ID NO 78
<211> LENGTH: 598
<212> TYPE: PRT
<213> ORGANISM: Homo sapiens

<400> SEQUENCE: 78

Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Thr Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205
```

-continued

```
Ser His His Val Val Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu Ala Asn Lys Asn
    290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
                325                 330                 335

Ser Leu Lys Gly Arg Arg Gly Arg Leu Pro Ser Lys Pro Lys Ser Pro
            340                 345                 350

Gln Glu Pro Ser Pro Pro Ser Pro Pro Val Ser Leu Ile Ser Ala Leu
        355                 360                 365

Val Arg Ala His Val Asp Ser Asn Pro Ala Met Thr Ser Leu Asp Tyr
    370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ala Ile Ile Asp Lys Leu Phe
            580                 585                 590

Leu Asp Thr Leu Pro Phe
        595
```

<210> SEQ ID NO 79
<211> LENGTH: 2603
<212> TYPE: DNA

<213> ORGANISM: Homo sapiens

<400> SEQUENCE: 79

```
ttcctggtgt aagctttggt atggatggtg gccgtctccc tacagactgg gagctgttag     60
agggcaggga tcctagctga cacatctatg tcctcgcctt ggttggaggc ctccaccatg    120
gacagaggcc aggccctgcc cctcccaggc agcctggctc cttctgctgg gccctgaagg    180
cagacgggat aatgtggttg gccaaggcct gttggtccat ccagagtgag atgccctgta    240
tccaagccca atatgggaca ccagcaccga gtccgggacc ccgtgaccac ctggcaagcg    300
accccctgac ccctgagttc atcaagccca ccatggacct ggccagcccc gaggcagccc    360
ccgctgcccc cactgccctg cccagcttca gcaccttcat ggacggctac acaggagagt    420
ttgacacctt cctctaccag ctgccaggaa cagtccagcc atgctcctca gcctcctcct    480
cggcctcctc cacatcctcg tcctcagcca cctcccctgc ctctgcctcc ttcaagttcg    540
aggacttcca ggtgtacggc tgctaccccg gcccctgag cggcccagtg gatgaggccc     600
tgtcctccag tggctctgac tactatggca gcccctgctc ggccccgtcg ccctccacgc    660
ccagcttcca gccgccccag ctctctccct gggatggctc cttcggccac ttctcgccca    720
gccagactta cgaaggcctg cgggcatgga cagagcagct gcccaaagcc tctgggcccc    780
cacagcctcc agccttcttt tccttcagtc ctcccaccgg ccccagcccc agcctggccc    840
agagccccct gaagttgttc ccctcacagg ccacccacca gctgggggag ggagagagct    900
attccatgcc tacggccttc ccaggtttgg cacccacttc tccacacctt gagggctcgg    960
ggatactgga tacacccgtg acctcaacca aggcccggag cggggcccca ggtggaagtg   1020
aaggccgctg tgctgtgtgt ggggacaacg cttcatgcca gcattatggt gtccgcacat   1080
gtgagggctg caagggcttc ttcaagcgca cagtgcagaa aaacgccaag tacatctgcc   1140
tggctaacaa ggactgccct gtggacaaga ggcggcgaaa ccgctgccag ttctgccgct   1200
tccagaagtg cctggcggtg ggcatggtga aggaagttgt ccgaacagac agcctgaagg   1260
ggcggcgggg ccggctacct tcaaaaccca agcagccccc agatgcctcc cctgccaatc   1320
tcctcacttc cctggtccgt gcacacctgg actcagggcc cagcactgcc aaactggact   1380
actccaagtt ccaggagctg gtgctgcccc actttgggaa ggaagatgct ggggatgtac   1440
agcagttcta cgacctgctc tccggttctc tggaggtcat ccgcaagtgg gcggagaaga   1500
tccctggctt tgctgagctg tcaccggctg accaggacct gttgctggag tcggccttcc   1560
tggagctctt catcctccgc ctggcgtaca ggtctaagcc aggcgagggc aagctcatct   1620
tctgctcagg cctggtgcta caccggctgc agtgtgcccg tggcttcggg gactggattg   1680
acagtatcct ggccttctca aggtccctgc acagcttgct tgtcgatgtc cctgccttcg   1740
cctgcctctc tgcccttgtc ctcatcaccg accggcatgg gctgcaggag ccgcggcggg   1800
tggaggagct gcagaaccgc atcgccagct gcctgaagga gcacgtggca gctgtggcgg   1860
gcgagcccca gccagccagc tgcctgtcac gtctgttggg caaactgccc gagctgcgga   1920
ccctgtgcac ccagggcctg cagcgcatct tctacctcaa gctggaggac ttggtgcccc   1980
ctccacccat cattgacaag atcttcatgg acacgctgcc cttctgaccc ctgcctggga   2040
acacgtgtgc acatgcgcac tctcatatgc caccccatgt gcctttagtc cacggacccc   2100
cagagcaccc ccaagcctgg gcttgagctg cagaatgact ccaccttctc acctgctcca   2160
ggaggtttgc agggagctca agcccttggg gagggggatg ccttcatggg ggtgacccca   2220
cgatttgtct tatccccccc agcctggccc cggcctttat gtttttttgta agataaaccg   2280
```

```
tttttaacac atagcgccgt gctgtaaata agcccagtgc tgctgtaaat acaggaagaa   2340

agagcttgag gtgggagcgg ggctgggagg aagggatggg ccccgccttc ctgggcagcc   2400

tttccagcct cctgctggct ctctcttcct accctccttc cacatgtaca taaactgtca   2460

ctctaggaag aagacaaatg acagattctg acatttatat ttgtgtattt tcctggattt   2520

atagtatgtg acttttctga ttaatatatt taatatattg aataaaaaat agacatgtag   2580

ttggaactga aaaaaaaaaa aaa                                           2603


<210> SEQ ID NO 80
<211> LENGTH: 611
<212> TYPE: PRT
<213> ORGANISM: Homo sapiens

<400> SEQUENCE: 80

Met Trp Leu Ala Lys Ala Cys Trp Ser Ile Gln Ser Glu Met Pro Cys
1               5                   10                  15

Ile Gln Ala Gln Tyr Gly Thr Pro Ala Pro Ser Pro Gly Pro Arg Asp
            20                  25                  30

His Leu Ala Ser Asp Pro Leu Thr Pro Glu Phe Ile Lys Pro Thr Met
        35                  40                  45

Asp Leu Ala Ser Pro Glu Ala Ala Pro Ala Ala Pro Thr Ala Leu Pro
    50                  55                  60

Ser Phe Ser Thr Phe Met Asp Gly Tyr Thr Gly Glu Phe Asp Thr Phe
65                  70                  75                  80

Leu Tyr Gln Leu Pro Gly Thr Val Gln Pro Cys Ser Ser Ala Ser Ser
                85                  90                  95

Ser Ala Ser Ser Thr Ser Ser Ser Ser Ala Thr Ser Pro Ala Ser Ala
            100                 105                 110

Ser Phe Lys Phe Glu Asp Phe Gln Val Tyr Gly Cys Tyr Pro Gly Pro
        115                 120                 125

Leu Ser Gly Pro Val Asp Glu Ala Leu Ser Ser Ser Gly Ser Asp Tyr
    130                 135                 140

Tyr Gly Ser Pro Cys Ser Ala Pro Ser Pro Ser Thr Pro Ser Phe Gln
145                 150                 155                 160

Pro Pro Gln Leu Ser Pro Trp Asp Gly Ser Phe Gly His Phe Ser Pro
                165                 170                 175

Ser Gln Thr Tyr Glu Gly Leu Arg Ala Trp Thr Glu Gln Leu Pro Lys
            180                 185                 190

Ala Ser Gly Pro Pro Gln Pro Pro Ala Phe Phe Ser Phe Ser Pro Pro
        195                 200                 205

Thr Gly Pro Ser Pro Ser Leu Ala Gln Ser Pro Leu Lys Leu Phe Pro
    210                 215                 220

Ser Gln Ala Thr His Gln Leu Gly Glu Gly Glu Ser Tyr Ser Met Pro
225                 230                 235                 240

Thr Ala Phe Pro Gly Leu Ala Pro Thr Ser Pro His Leu Glu Gly Ser
                245                 250                 255

Gly Ile Leu Asp Thr Pro Val Thr Ser Thr Lys Ala Arg Ser Gly Ala
            260                 265                 270

Pro Gly Gly Ser Glu Gly Arg Cys Ala Val Cys Gly Asp Asn Ala Ser
        275                 280                 285

Cys Gln His Tyr Gly Val Arg Thr Cys Glu Gly Cys Lys Gly Phe Phe
    290                 295                 300

Lys Arg Thr Val Gln Lys Asn Ala Lys Tyr Ile Cys Leu Ala Asn Lys
```

```
305                 310                 315                 320

Asp Cys Pro Val Asp Lys Arg Arg Arg Asn Arg Cys Gln Phe Cys Arg
                325                 330                 335

Phe Gln Lys Cys Leu Ala Val Gly Met Val Lys Glu Val Val Arg Thr
            340                 345                 350

Asp Ser Leu Lys Gly Arg Arg Gly Arg Leu Pro Ser Lys Pro Lys Gln
        355                 360                 365

Pro Pro Asp Ala Ser Pro Ala Asn Leu Leu Thr Ser Leu Val Arg Ala
    370                 375                 380

His Leu Asp Ser Gly Pro Ser Thr Ala Lys Leu Asp Tyr Ser Lys Phe
385                 390                 395                 400

Gln Glu Leu Val Leu Pro His Phe Gly Lys Glu Asp Ala Gly Asp Val
                405                 410                 415

Gln Gln Phe Tyr Asp Leu Leu Ser Gly Ser Leu Glu Val Ile Arg Lys
            420                 425                 430

Trp Ala Glu Lys Ile Pro Gly Phe Ala Glu Leu Ser Pro Ala Asp Gln
        435                 440                 445

Asp Leu Leu Leu Glu Ser Ala Phe Leu Glu Leu Phe Ile Leu Arg Leu
    450                 455                 460

Ala Tyr Arg Ser Lys Pro Gly Glu Gly Lys Leu Ile Phe Cys Ser Gly
465                 470                 475                 480

Leu Val Leu His Arg Leu Gln Cys Ala Arg Gly Phe Gly Asp Trp Ile
                485                 490                 495

Asp Ser Ile Leu Ala Phe Ser Arg Ser Leu His Ser Leu Leu Val Asp
            500                 505                 510

Val Pro Ala Phe Ala Cys Leu Ser Ala Leu Val Leu Ile Thr Asp Arg
        515                 520                 525

His Gly Leu Gln Glu Pro Arg Arg Val Glu Glu Leu Gln Asn Arg Ile
    530                 535                 540

Ala Ser Cys Leu Lys Glu His Val Ala Ala Val Ala Gly Glu Pro Gln
545                 550                 555                 560

Pro Ala Ser Cys Leu Ser Arg Leu Leu Gly Lys Leu Pro Glu Leu Arg
                565                 570                 575

Thr Leu Cys Thr Gln Gly Leu Gln Arg Ile Phe Tyr Leu Lys Leu Glu
            580                 585                 590

Asp Leu Val Pro Pro Pro Pro Ile Ile Asp Lys Ile Phe Met Asp Thr
        595                 600                 605

Leu Pro Phe
    610


<210> SEQ ID NO 81
<211> LENGTH: 4754
<212> TYPE: DNA
<213> ORGANISM: Homo sapiens

<400> SEQUENCE: 81

gaattctaga ggcggcggag ggtggcgagg agctctcgct ttctctcgct ccctccctct     60

ccgactccgt ctctctctct ctctctctct ctcccctccc tctctttccc tctgttccat    120

tttttccccc tctaaatcct ccctgccctg cgcgcctgga cacagattta ggaagcgaat    180

tcgctcacgt tttaggacaa ggaagagaga gaggcacggg agaagagccc agcaagattt    240

ggattgaaac cgagacaccc tccggaggct cggagcagag gaaggaggag gagggcggcg    300

aacggaagcc agtttgcaat tcaagttttg atagcgctgg tagaaggggg tttaaatcag    360
```

```
atttttttt ttttaaagga gagagacttt ttccgctctc tcgctccctg ttaaagccgg    420
gtctagcaca gctgcagacg ccaccagcga gaaagaggga gaggaagaca gataggggc    480
gggggaagaa gaaaaagaaa ggtaaaaagt cttctaggag aacctttcac atttgcaaca    540
aaagacctag gggctggaga gagattcctg ggacgcaggg ctggagtgtc tatttcgagc    600
tcagcggcag ggctcgggcg cgagtcgaga ccctgctcgc tcctctcgct tctgaaaccg    660
acgttcagga gcggcttttt aaaaacgcaa ggcacaagga cggtcacccg cgcgactatg    720
tttgctgatt tttcgccttg ccctctttaa aagcggcctc ccattctcca aaagacactt    780
cccctcctcc ctttgaagtg cattagttgt gatttctgcc tcctttctt ttttctttct    840
tttttgtttt gctttttccc cccttttgaa ttatgtgctg ctgttaaaca acaacaaaaa    900
aacaacaaaa cacagcagct gcggacttgt ccccggctgg agcccagcgc cccgcctgga    960
gtggatgagc ctctccatga gagatccggt cattcctggg acaagcatgg cctaccatcc   1020
gttcctacct caccgggcgc cggacttcgc catgagcgcg gtgctgggtc accagccgcc   1080
gttcttcccc gcgctgacgc tgcctcccaa cggcgcggcg gcgctctcgc tgccgggcgc   1140
cctggccaag ccgatcatgg atcaattggt gggggcggcc gagaccggca tcccgttctc   1200
ctccctgggg ccccaggcgc atctgaggcc tttgaagacc atggagcccg aagaagaggt   1260
ggaggacgac cccaaggtgc acctggaggc taaagaactt tgggatcagt ttcacaagcg   1320
gggcaccgag atggtcatta ccaagtcggg aaggcgaatg tttcctccat ttaaagtgag   1380
atgttctggg ctggataaaa aagccaaata cattttattg atggacatta tagctgctga   1440
tgactgtcgt tataaatttc acaattctcg gtggatggtg gctggtaagg ccgaccccga   1500
aatgccaaag aggatgtaca ttcacccgga cagccccgct actggggaac agtggatgtc   1560
caaagtcgtc actttccaca aactgaaact caccaacaac atttcagaca aacatggatt   1620
tactatattg aactccatgc acaaatacca gccccggttc cacattgtaa gagccaatga   1680
catcttgaaa ctcccttata gtacatttcg gacatacttg ttccccgaaa ctgaattcat   1740
cgctgtgact gcataccaga atgataagat aacccagtta aaaatagaca acaacccttt   1800
tgcaaaaggt ttccgggaca ctggaaatgg ccgaagagaa aaaagaaaac agctcaccct   1860
gcagtccatg agggtgtttg atgaaagaca caaaaaggag aatgggacct ctgatgagtc   1920
ctccagtgaa caagcagctt tcaactgctt cgcccaggct tcttctccag ccgcctccac   1980
tgtagggaca tcgaacctca aagatttatg tcccagcgag ggtgagagcg acgccgaggc   2040
cgagagcaaa gaggagcatg gccccgaggc ctgcgacgcg gccaagatct ccaccaccac   2100
gtcggaggag ccctgccgtg acaagggcag ccccgcggtc aaggctcacc ttttcgctgc   2160
tgagcggccc cgggacagcg ggcggctgga caaagcgtcg cccgactcac gccatagccc   2220
cgccaccatc tcgtccagca ctcgcggcct gggcgcggag gagcgcagga gcccggttcg   2280
cgagggcaca gcgccggcca aggtggaaga ggcgcgcgcg ctcccgggca aggaggcctt   2340
cgcgccgctc acggtgcaga cggacgcggc cgccgcgcac ctggcccagg gcccccctgcc   2400
tggcctcggc ttcgccccgg gcctggcggg ccaacagttc ttcaacgggc acccgctctt   2460
cctgcacccc agccagtttg ccatgggggg cgccttctcc agcatggcgg ccgctggcat   2520
gggtcccctc ctggccacgg tttctggggc ctccaccggt gtctcgggcc tggattccac   2580
ggccatggcc tctgccgctg cggcgcaggg actgtccggg gcgtccgcgg ccaccctgcc   2640
cttccacctc cagcagcacg tcctggcctc tcagggcctg gccatgtccc ctttcggaag   2700
cctgttccct taccccctaca cgtacatggc cgcagcggcg gccgcctcct ctgcggcagc   2760
```

```
ctccagctcg gtgcaccgcc accccttcct caatctgaac accatgcgcc cgcggctgcg   2820
ctacagcccc tactccatcc cggtgccggt cccggacggc agcagtctgc tcaccaccgc   2880
cctgccctcc atggcggcgg ccgcggggcc cctggacggc aaagtcgccg ccctggccgc   2940
cagcccggcc tcggtggcag tggactcggg ctctgaactc aacagccgct cctccacgct   3000
ctcctccagc tccatgtcct tgtcgcccaa actctgcgcg gagaaagagg cggccaccag   3060
cgaactgcag agcatccagc ggttggttag cggcttggaa gccaagccgg acaggtcccg   3120
cagcgcgtcc ccgtagaccc gtcccagaca cgtcttttca ttccagtcca gttcaggctg   3180
ccgtgcactt tgtcggatat aaaataaacc acgggcccgc catggcgtta gcccttcctt   3240
ttgcagttgc gtctgggaag ggccccgga ctccctcgag agaatgtgct agagacagcc   3300
cctgtcttct tggcgtggtt tatatgtccg ggatctggat cagattctgg gggctcagaa   3360
acgtcggttg cattgagcta ctgggggtag gagttccaac atttatgtcc agagcaactt   3420
ccagcaaggc tggtctgggt ctctgcccac caggcgggga ggtgttcaaa gacatctccc   3480
tcagtgcgga tttatatata tatttttcct tcactgtgtc aagtggaaac aaaaacaaaa   3540
tctttcaaaa aaaaaatcgg gacaagtgaa cacattaaca tgattctgtt tgtgcagatt   3600
aaaaacttta tagggacttg cattatcggt tctcaataaa ttactgagca gctttgtttg   3660
gggagggaag tccctaccat ccttgtttag tctatattaa gaaaatctgt gtctttttaa   3720
tattcttgtg atgttttcag agccgctgta ggtctcttct tgcatgtcca cagtaatgta   3780
tttgtggttt ttattttgaa cgcttgcttt tagagagaaa acaatatagc cccctaccct   3840
tttcccaatc ctttgccctc aaatcagtga cccaagggag ggggggattt aaagggaagg   3900
agtgggcaaa acacataaaa tgaatttatt atatctaagc tctgtagcag gattcatgtc   3960
gttctttgac agttctttct ctttcctgta tatgcaataa caaggtttta aaaaaataat   4020
aaagaagtga gactattaga caaagtattt atgtaattat ttgataactc ttgtaaatag   4080
gtggaatatg aatgcttgga aaattaaact ttaatttatt gacattgtac atagctctgt   4140
gtaaatagaa ttgcaactgt caggttttgt gttcttgttt tcctttagtt gggtttattt   4200
ccaggtcaca gaattgctgt taacactaga aaacacactt cctgcaccaa caccaatacc   4260
ctttcaaaag agttgtctgc aacatttttg ttttcttttt taatgtccaa aagtgggggga   4320
aagtgctatt tcctattttc accaaaattg gggaaggagt gccactttcc agctccactt   4380
caaattcctt aaaatataac tgagattgct gtggggaggg aggagggcag aggctgcggt   4440
ttgacttttt aatttttctt ttgttatttg tatttgctag tctctgattt cctcaaaacg   4500
aagtggaatt tactactgtt gtcagtatcg gtgttttgaa ttggtgcctg cctatagaga   4560
tatattcaca gttcaaaagt caggtgctga gagatggttt aaagacaaat tcatgaaggt   4620
atattttgtg ttatagttgt tgatgagttc tttggttttc tgtatttttc cccctctctt   4680
taaaacatca ctgaaatttc aataaatttt tattgaaatg tctaaaaaaa aaaaaaaaaa   4740
aaaaaaaaaa aaaa                                                     4754
```

```
<210> SEQ ID NO 82
<211> LENGTH: 723
<212> TYPE: PRT
<213> ORGANISM: Homo sapiens

<400> SEQUENCE: 82

Met Ser Leu Ser Met Arg Asp Pro Val Ile Pro Gly Thr Ser Met Ala
1               5                   10                  15
```

```
Tyr His Pro Phe Leu Pro His Arg Ala Pro Asp Phe Ala Met Ser Ala
            20                  25                  30

Val Leu Gly His Gln Pro Pro Phe Phe Pro Ala Leu Thr Leu Pro Pro
        35                  40                  45

Asn Gly Ala Ala Ala Leu Ser Leu Pro Gly Ala Leu Ala Lys Pro Ile
    50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
    130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Ile Leu Asn Ser
    210                 215                 220

Met His Lys Tyr Gln Pro Arg Phe His Ile Val Arg Ala Asn Asp Ile
225                 230                 235                 240

Leu Lys Leu Pro Tyr Ser Thr Phe Arg Thr Tyr Leu Phe Pro Glu Thr
                245                 250                 255

Glu Phe Ile Ala Val Thr Ala Tyr Gln Asn Asp Lys Ile Thr Gln Leu
            260                 265                 270

Lys Ile Asp Asn Asn Pro Phe Ala Lys Gly Phe Arg Asp Thr Gly Asn
        275                 280                 285

Gly Arg Arg Glu Lys Arg Lys Gln Leu Thr Leu Gln Ser Met Arg Val
    290                 295                 300

Phe Asp Glu Arg His Lys Lys Glu Asn Gly Thr Ser Asp Glu Ser Ser
305                 310                 315                 320

Ser Glu Gln Ala Ala Phe Asn Cys Phe Ala Gln Ala Ser Ser Pro Ala
                325                 330                 335

Ala Ser Thr Val Gly Thr Ser Asn Leu Lys Asp Leu Cys Pro Ser Glu
            340                 345                 350

Gly Glu Ser Asp Ala Glu Ala Glu Ser Lys Glu Glu His Gly Pro Glu
        355                 360                 365

Ala Cys Asp Ala Ala Lys Ile Ser Thr Thr Thr Ser Glu Glu Pro Cys
    370                 375                 380

Arg Asp Lys Gly Ser Pro Ala Val Lys Ala His Leu Phe Ala Ala Glu
385                 390                 395                 400

Arg Pro Arg Asp Ser Gly Arg Leu Asp Lys Ala Ser Pro Asp Ser Arg
                405                 410                 415

His Ser Pro Ala Thr Ile Ser Ser Ser Thr Arg Gly Leu Gly Ala Glu
            420                 425                 430
```

```
Glu Arg Arg Ser Pro Val Arg Glu Gly Thr Ala Pro Ala Lys Val Glu
        435                 440                 445

Glu Ala Arg Ala Leu Pro Gly Lys Glu Ala Phe Ala Pro Leu Thr Val
    450                 455                 460

Gln Thr Asp Ala Ala Ala Ala His Leu Ala Gln Gly Pro Leu Pro Gly
465                 470                 475                 480

Leu Gly Phe Ala Pro Gly Leu Ala Gly Gln Gln Phe Phe Asn Gly His
                485                 490                 495

Pro Leu Phe Leu His Pro Ser Gln Phe Ala Met Gly Gly Ala Phe Ser
            500                 505                 510

Ser Met Ala Ala Ala Gly Met Gly Pro Leu Leu Ala Thr Val Ser Gly
        515                 520                 525

Ala Ser Thr Gly Val Ser Gly Leu Asp Ser Thr Ala Met Ala Ser Ala
    530                 535                 540

Ala Ala Ala Gln Gly Leu Ser Gly Ala Ser Ala Ala Thr Leu Pro Phe
545                 550                 555                 560

His Leu Gln Gln His Val Leu Ala Ser Gln Gly Leu Ala Met Ser Pro
                565                 570                 575

Phe Gly Ser Leu Phe Pro Tyr Pro Tyr Thr Tyr Met Ala Ala Ala Ala
            580                 585                 590

Ala Ala Ser Ser Ala Ala Ala Ser Ser Ser Val His Arg His Pro Phe
        595                 600                 605

Leu Asn Leu Asn Thr Met Arg Pro Arg Leu Arg Tyr Ser Pro Tyr Ser
    610                 615                 620

Ile Pro Val Pro Val Pro Asp Gly Ser Ser Leu Leu Thr Thr Ala Leu
625                 630                 635                 640

Pro Ser Met Ala Ala Ala Ala Gly Pro Leu Asp Gly Lys Val Ala Ala
                645                 650                 655

Leu Ala Ala Ser Pro Ala Ser Val Ala Val Asp Ser Gly Ser Glu Leu
            660                 665                 670

Asn Ser Arg Ser Ser Thr Leu Ser Ser Ser Ser Met Ser Leu Ser Pro
        675                 680                 685

Lys Leu Cys Ala Glu Lys Glu Ala Ala Thr Ser Glu Leu Gln Ser Ile
    690                 695                 700

Gln Arg Leu Val Ser Gly Leu Glu Ala Lys Pro Asp Arg Ser Arg Ser
705                 710                 715                 720

Ala Ser Pro


<210> SEQ ID NO 83
<211> LENGTH: 3095
<212> TYPE: DNA
<213> ORGANISM: Homo sapiens

<400> SEQUENCE: 83

ggaggacgga cggacagggc cagcctgctg tccggctgcc gcccgccgtg gtgtgagggg      60

gtttctgcgc acccacagtc gccaccgtcc cacctgggct gccggagcct ccccctggac     120

ccctggtgcc cactgccacc ctcatccggt gtgagagcgc tgcttccgct tcgcggacgc     180

cgcgggcatg gactattcgt acgacgagga cctggacgag ctgtgccccg tgtgcgggga     240

caaggtgtcc ggctaccact acggactgct cacgtgtgag agctgcaagg gcttcttcaa     300

gcgcacggtg cagaacaaca agcactacac gtgcaccgag agccagagct gcaagatcga     360

caagacgcag cgcaagcgct gtcccttctg ccgcttccag aaatgcctga cggtggggat     420

gcgcctggaa gccgtgcgcg ctgaccgtat gaggggtggc cggaacaagt ttgggccgat     480
```

```
gtacaagcgg gaccgggccc tgaaacagca gaagaaggca cagattcggg ccaatggctt    540
caagctggag acagggcccc cgatgggggt gcccccgccg cccccctcccg caccggacta    600
cgtgctgcct cccagcctgc atgggcctga gcccaagggc ctggccgccg gtccacctgc    660
tgggccactg ggcgactttg gggccccagc actgcccatg gccgtgcccg gtgcccacgg    720
gccactggct ggctacctct accctgcctt tcctggccgt gccatcaagt ctgagtaccc    780
ggagccttat gccagccccc cacagcctgg gctgccgtac ggctacccag agcccttctc    840
tggagggccc aacgtgcctg agctcatcct gcagctgctg cagctggagc cggatgagga    900
ccaggtgcgg gcccgcatct tgggctgcct gcaggagccc accaaaagcc gccccgacca    960
gccggcggcc ttcggcctcc tgtgcagaat ggccgaccag accttcatct ccatcgtgga   1020
ctgggcacgc aggtgcatgg tcttcaagga gctggaggtg gccgaccaga tgacgctgct   1080
gcagaactgc tggagcgagc tgctggtgtt cgaccacatc taccgccagg tccagcacgg   1140
caaggagggc agcatcctgc tggtcaccgg gcaggaggtg gagctgacca cagtggccac   1200
ccaggcgggc tcgctgctgc acagcctggt gttgcgggcg caggagctgg tgctgcagct   1260
gcttgcgctg cagctggacc ggcaggagtt tgtctgcctc aagttcatca tcctcttcag   1320
cctggatttg aagttcctga ataaccacat cctggtgaaa gacgctcagg agaaggccaa   1380
cgccgccctg cttgactaca ccctgtgcca ctacccgcac tgcggggaca aattccagca   1440
gctgctgctg tgcctggtgg aggtgcgggc cctgagcatg caggccaagg agtacctgta   1500
ccacaagcac ctgggcaacg agatgccccg caacaacctg ctcatcgaaa tgctgcaagc   1560
caagcagact tgagcctggg ccgggggcgg ggccgggact gggggcggga ctgggggcgg   1620
ggcctgggcg gggccgcagc cacaccgctg gctccgcatg gttcattttc tgatgcccac   1680
cgaggagccc cagccccgtc ccagaggccg ctgcccctga gttctgacac tgtgtgtttg   1740
ggaaggtggg tgaggctggg cagggcctgg cggaggtgga gtggccactg gcacttgcct   1800
gctgcttgga gtgccccaag gaggtggctg ttaaccaccc gccccgcccc ctccctgctc   1860
ccagctctct ctcctggagt ctgaagcctg caggtccggg gaggaggttc gggattccct   1920
ggtgggcctc gacgtccctt ggatcagagg tcatcccttc ctcctctcct ggaaacagac   1980
agggagaagt tgagcaggta tcaactaggg gaggagagag ggtctccagt gttcccccca   2040
tagagaccag gagggagagc ctctgttttg taaactaagg ataaccgagt ttgctaaatt   2100
gagaggggct attgggccct agaggacact aggagactgg ttaggacaaa aagaccttct   2160
ccctagccct tctaccccac ctgacctctg caagaggggg cattgataca tcatcgggaa   2220
aaaactttgc tccaggcatc actgattccc tctcccaccc aaggagaacg tttggtacaa   2280
tcgacatcct agccccaccc agaggtggcc ctcccaggct ggtatttatc tgcaaggttg   2340
tagtcaagag gtttttctcc ccgctttttg tttttaagct tctagacact ccttgaaatg   2400
tgtgtgtgat ggagggaagg ggacagattt gaggactgaa gctggggctt ggggattgcc   2460
actaagtaca gctgacggtt tctccccgga cactcgccta ctaagtaccc ttggggtggt   2520
gctgggtcat tacttctgag ccccagcccc aatccagaga agcgctgttg cccgccctcc   2580
acccactagg tgaacagcag gatgccctgt tgggggcttc aggtctctgt gggtgggaat   2640
gcaagtgaac ttgggagggg gcacgggcct gtagatcagg gatagcgctg ttgatcccct   2700
ctctgtggct ccaacccgtt gggtcccttg ctgcaaaccc atgaagctgg ccctcagctc   2760
cctgaccccc tgtcctaggt catgaaggac actctgcagg gtgaagcacc agggagaggc   2820
```

```
ctcggctgtc tcctgtcccc ggcggggtgc ctgctgtccg tcccgctttc atgttactgt   2880

tgcagcttgt gctgagcctg cccagttgga ggagactggg cacccctgcc tcctgcctcc   2940

cgcctcccgc caccctgtct cagtacctcc cctccccgcc ccctgaaaca tgtgcccctg   3000

ccaaggccgg agacccacag ccctgaaacg agaagtgccc ttaaggatca ccccagcccc   3060

cacagccctg gaataaattt cgcaattagt ttcca                              3095


<210> SEQ ID NO 84
<211> LENGTH: 461
<212> TYPE: PRT
<213> ORGANISM: Homo sapiens

<400> SEQUENCE: 84

Met Asp Tyr Ser Tyr Asp Glu Asp Leu Asp Glu Leu Cys Pro Val Cys
1               5                   10                  15

Gly Asp Lys Val Ser Gly Tyr His Tyr Gly Leu Leu Thr Cys Glu Ser
            20                  25                  30

Cys Lys Gly Phe Phe Lys Arg Thr Val Gln Asn Asn Lys His Tyr Thr
        35                  40                  45

Cys Thr Glu Ser Gln Ser Cys Lys Ile Asp Lys Thr Gln Arg Lys Arg
    50                  55                  60

Cys Pro Phe Cys Arg Phe Gln Lys Cys Leu Thr Val Gly Met Arg Leu
65                  70                  75                  80

Glu Ala Val Arg Ala Asp Arg Met Arg Gly Gly Arg Asn Lys Phe Gly
                85                  90                  95

Pro Met Tyr Lys Arg Asp Arg Ala Leu Lys Gln Gln Lys Lys Ala Gln
            100                 105                 110

Ile Arg Ala Asn Gly Phe Lys Leu Glu Thr Gly Pro Pro Met Gly Val
        115                 120                 125

Pro Pro Pro Pro Pro Pro Ala Pro Asp Tyr Val Leu Pro Pro Ser Leu
    130                 135                 140

His Gly Pro Glu Pro Lys Gly Leu Ala Ala Gly Pro Pro Ala Gly Pro
145                 150                 155                 160

Leu Gly Asp Phe Gly Ala Pro Ala Leu Pro Met Ala Val Pro Gly Ala
                165                 170                 175

His Gly Pro Leu Ala Gly Tyr Leu Tyr Pro Ala Phe Pro Gly Arg Ala
            180                 185                 190

Ile Lys Ser Glu Tyr Pro Glu Pro Tyr Ala Ser Pro Pro Gln Pro Gly
        195                 200                 205

Leu Pro Tyr Gly Tyr Pro Glu Pro Phe Ser Gly Gly Pro Asn Val Pro
    210                 215                 220

Glu Leu Ile Leu Gln Leu Leu Gln Leu Glu Pro Asp Glu Asp Gln Val
225                 230                 235                 240

Arg Ala Arg Ile Leu Gly Cys Leu Gln Glu Pro Thr Lys Ser Arg Pro
                245                 250                 255

Asp Gln Pro Ala Ala Phe Gly Leu Leu Cys Arg Met Ala Asp Gln Thr
            260                 265                 270

Phe Ile Ser Ile Val Asp Trp Ala Arg Arg Cys Met Val Phe Lys Glu
        275                 280                 285

Leu Glu Val Ala Asp Gln Met Thr Leu Leu Gln Asn Cys Trp Ser Glu
    290                 295                 300

Leu Leu Val Phe Asp His Ile Tyr Arg Gln Val Gln His Gly Lys Glu
305                 310                 315                 320

Gly Ser Ile Leu Leu Val Thr Gly Gln Glu Val Glu Leu Thr Thr Val
```

```
                325                 330                 335

Ala Thr Gln Ala Gly Ser Leu Leu His Ser Leu Val Leu Arg Ala Gln
            340                 345                 350

Glu Leu Val Leu Gln Leu Leu Ala Leu Gln Leu Asp Arg Gln Glu Phe
        355                 360                 365

Val Cys Leu Lys Phe Ile Ile Leu Phe Ser Leu Asp Leu Lys Phe Leu
    370                 375                 380

Asn Asn His Ile Leu Val Lys Asp Ala Gln Glu Lys Ala Asn Ala Ala
385                 390                 395                 400

Leu Leu Asp Tyr Thr Leu Cys His Tyr Pro His Cys Gly Asp Lys Phe
                405                 410                 415

Gln Gln Leu Leu Leu Cys Leu Val Glu Val Arg Ala Leu Ser Met Gln
            420                 425                 430

Ala Lys Glu Tyr Leu Tyr His Lys His Leu Gly Asn Glu Met Pro Arg
        435                 440                 445

Asn Asn Leu Leu Ile Glu Met Leu Gln Ala Lys Gln Thr
    450                 455                 460


<210> SEQ ID NO 85
<211> LENGTH: 4787
<212> TYPE: DNA
<213> ORGANISM: Homo sapiens

<400> SEQUENCE: 85

atagtttgtc atctttttag ctgcgaagac gccttcgtgg gtctgcgtcc ggagcaaggc      60

ggttacccga tcccggcagt gagccgcgcc gcgcgtcgtg gcggcctgat ttctgtttaa     120

ctttaatagg gcgatctcga gtgtctcaat ttaaaatggt gaattactcc tatgatgaag     180

atctggaaga gctttgtccc gtgtgtggag ataaagtgtc tgggtaccat tatgggctcc     240

tcacctgtga aagctgcaag ggattttta agcgaacagt ccaaaataat aaaaggtaca      300

catgtataga aaaccagaac tgccaaattg acaaaacaca gagaaagcgt tgtccttact     360

gtcgttttca aaaatgtcta agtgttggaa tgaagctaga agctgtaagg gccgaccgaa     420

tgcgtggagg aaggaataag tttgggccaa tgtacaagag agacagggcc ctgaagcaac     480

agaaaaaagc cctcatccga gccaatggac ttaagctaga agccatgtct caggtgatcc     540

aagctatgcc ctctgacctg accatttcct ctgcaattca aaacatccac tctgcctcca     600

aaggcctacc tctgaaccat gctgccttgc ctcctacaga ctatgacaga agtccctttg     660

taacatcccc cattagcatg acaatgcccc ctcacggcag cctgcaaggt taccaaacat     720

atggccactt tcctagccgg gccatcaagt ctgagtaccc agacccctat accagctcac     780

ccgagtccat aatgggctat tcatatatgg atagttacca gacgagctct ccagcaagca     840

tcccacatct gatactggaa cttttgaagt gtgagccaga tgagcctcaa gtccaggcta     900

aaatcatggc ctatttgcag caagagcagg ctaaccgaag caagcacgaa aagctgagca     960

cctttgggct tatgtgcaaa atggcagatc aaactctctt ctccattgtc gagtgggcca    1020

ggagtagtat cttcttcaga gaacttaagg ttgatgacca aatgaagctg cttcagaact    1080

gctggagtga gctcttaatc ctcgaccaca tttaccgaca agtggtacat ggaaaggaag    1140

gatccatctt cctggttact gggcaacaag tggactattc cataatagca tcacaagccg    1200

gagccaccct caacaacctc atgagtcatg cacaggagtt agtggcaaaa cttcgttctc    1260

tccagtttga tcaacgagag ttcgtatgtc tgaaattctt ggtgctcttt agtttagatg    1320

tcaaaaacct tgaaaacttc cagctggtag aaggtgtcca ggaacaagtc aatgccgccc    1380
```

```
tgctggacta cacaatgtgt aactacccgc agcagacaga gaaatttgga cagctacttc   1440
ttcgactacc cgaaatccgg gccatcagta tgcaggctga agaatacctc tactacaagc   1500
acctgaacgg ggatgtgccc tataataacc ttctcattga aatgttgcat gccaaaagag   1560
cataagttac aacccctagg agctctgctt tcaaaacaaa aagagattgg gggagtgggg   1620
agggggaaga agaacaggaa gaaaaaaagt actctgaact gctccaagta acgctaatta   1680
aaaacttgct ttaaagatat tgaatttaaa aaggcataat aatcaaatac ttaatagcaa   1740
ataaatgatg tatcagggta tttgtattgc aaactgtgaa tcaaaggctt cacagcccca   1800
gaggattcca tataaaagac attgtaatgg agtggattga actcacagat ggataccaac   1860
acggtcagaa gaaaaacgga cagaacggtt cttgtatatt taaactgatc tccactatga   1920
agaaatttag gaactaatct tattaattag gcttatacag cgggggattt gagcttacag   1980
gattcctcca tggtaaagct gaactgaaac aattctcaag aatgcatcag ctgtacctac   2040
aatagcccct ccctcttcct ttgaaggccc cagcacctct gccctgtggt caccgaatct   2100
gtactaagga cctgtgttca gccacaccca gtggtagctc caccaaatca tgaacagcct   2160
aattttgagt gtctgtgtct tagacctgca aacagctaat aggaaattct attaatatgt   2220
tagcttgcca ttttaaatat gttctgaggg ttgttttgtc tcgtgttcat gatgttaaga   2280
aaatgcaggc agtatccctc atcttatgta agtgttaatt aatattaagg gaaatgacta   2340
caaactttca aagcaaatgc tccatagcta aagcaactta gaccttattt ctgctactgt   2400
tgctgaaatg tggctttggc attgttggat ttcataaaaa atttctggca ggaagtcttg   2460
ttagtataca tcagtctttt tcatcatcca agtttgtagt tcatttaaaa atacaacatt   2520
aaacacattt tgctaggatg tcaaatagtc acagttctaa gtagttggaa acaaaattga   2580
cgcatgttaa tctatgcaaa gagaaaggaa aggatgaggt gatgtattga ctcaaggttc   2640
attcttgctg caattgaaca tcctcaagag ttgggatgga aatggtgatt tttacatgtg   2700
tcctggaaag atattaaagt aattcaaatc ttccccaaag gggaaaggaa gagagtgata   2760
ctgacctttt taagtcatag accaaagtct gctgtagaac aaatatggga ggacaaagaa   2820
tcgcaaattc ttcaaatgac tattatcagt attattaaca tgcgatgcca caggtatgaa   2880
agtcttgcct tatttcacaa ttttaaaagg tagctgtgca gatgtggatc aacatttgtt   2940
taaaataaag tattaatact ttaaagtcaa ataagatata gtgtttacat tctttaggtc   3000
ctgaggggca gggggatctg tgatataaca aaatagcaaa agcggtaatt tccttaatgt   3060
tatttttctg attggtaatt atttttaaca gtacttaatt attctatgtc gtgagacact   3120
aaaatcaaaa acgggaatct catttagact ttaatttttt tgagattatc ggcggcacaa   3180
tcactttgta gaaactgtaa aaaataaaag tatctcctag tcccttaatt ttttcataaa   3240
tatttctggc ttttgagtag tgtatttata ttgtatatca tactttcaac tgtagacaat   3300
tatgatgcta atttattgtt tcttggtttc acctttgtat aagatatagc caagactgaa   3360
gaaaccaaat atatgtgttt actgtagcat gtcttcaaat tagtggaact tagttcaggg   3420
acatagaaga gtcttaatga attaaaatca ttcacttgat taaatgtctg taaatcttca   3480
tcattcctac tgtagtttat ttaatatcta ttgtaaatta tgtgacttgt agcttcctct   3540
ggttttcaag taaactcaac aaggtggagt cttacctggt tttcctttcc aagcattgta   3600
aattgtatac caaagatatt agttattact tctgtgtgta caaagaggat tattttatta   3660
tgtttattaa tcacctctaa tactcatcca catgaagggt acacattagg taagctgggc   3720
```

```
gttgactcat gcgcagtctc agtcacccgt gttatcttcg tggctcaaag gacaatgcaa   3780

aatcgccgat cagagctcat acccaaagca ttacagagaa cagcagcatc attgccctcc   3840

ccagctgaaa aacaagttgg ctagaagata catggagagg aatggtgtgg tcaacagtta   3900

atgaaacggt tctatcatgc atgtgtaatg tggatggaga caattataag atttgactat   3960

aactatttgg agggtcttta acattgccaa aaaaacaaat atgttgattt ttattttatt   4020

ttatttttta ttttaagagg cgggatcttg atctcacatg ttgcccaggc tggccttgaa   4080

ctcctgggct caagcattcc tcctgcctca gcctccccca tagctgggac taggggtgca   4140

tgccagcata cctggctacg ttgactctta aaatctatgt tctcttattt taaagataca   4200

gtgctcccca ctgaaaatta aacctaaaaa atgtcacata ttggtatgtt gttaacctgg   4260

tagattaaat catgagaatg attagaaaga cgggcaacac agcgggttac atccacactg   4320

ctgatcacac caacgacagg agctgataag caagaaagcg tcacagccag cgtctgttca   4380

cccaaggttg acaagtgaag tttctctaat gttgattgtt agccgatttg taacctggca   4440

tttacttagc aactgcctta tcaattacag gatttgccgg taaaagcaga ctcaaatata   4500

aaggtttttg gcttaacttg gtttattata gttgctctat gtttgtaaac agacaatctc   4560

taatgtctga ttatttgtat cacagatctg cagctgcctt ggacttgaat ccatgcaatg   4620

tttagagtgt gaagtcagtt acttgttgat gttttcttac tgtatcaatg aaatacatat   4680

tgtcatgtca gttcttgcca ggaacttctc aacaaaatgg aatttttttt ttcagtattt   4740

caataaatat tgatatgccc agcctgataa tttttaaaaa aaaaaaa                 4787
```

```
<210> SEQ ID NO 86
<211> LENGTH: 469
<212> TYPE: PRT
<213> ORGANISM: Homo sapiens

<400> SEQUENCE: 86

Met Val Asn Tyr Ser Tyr Asp Glu Asp Leu Glu Glu Leu Cys Pro Val
1               5                   10                  15

Cys Gly Asp Lys Val Ser Gly Tyr His Tyr Gly Leu Leu Thr Cys Glu
            20                  25                  30

Ser Cys Lys Gly Phe Phe Lys Arg Thr Val Gln Asn Asn Lys Arg Tyr
        35                  40                  45

Thr Cys Ile Glu Asn Gln Asn Cys Gln Ile Asp Lys Thr Gln Arg Lys
    50                  55                  60

Arg Cys Pro Tyr Cys Arg Phe Gln Lys Cys Leu Ser Val Gly Met Lys
65                  70                  75                  80

Leu Glu Ala Val Arg Ala Asp Arg Met Arg Gly Gly Arg Asn Lys Phe
                85                  90                  95

Gly Pro Met Tyr Lys Arg Asp Arg Ala Leu Lys Gln Gln Lys Lys Ala
            100                 105                 110

Leu Ile Arg Ala Asn Gly Leu Lys Leu Glu Ala Met Ser Gln Val Ile
        115                 120                 125

Gln Ala Met Pro Ser Asp Leu Thr Ile Ser Ser Ala Ile Gln Asn Ile
    130                 135                 140

His Ser Ala Ser Lys Gly Leu Pro Leu Asn His Ala Ala Leu Pro Pro
145                 150                 155                 160

Thr Asp Tyr Asp Arg Ser Pro Phe Val Thr Ser Pro Ile Ser Met Thr
                165                 170                 175

Met Pro Pro His Gly Ser Leu Gln Gly Tyr Gln Thr Tyr Gly His Phe
            180                 185                 190
```

```
Pro Ser Arg Ala Ile Lys Ser Glu Tyr Pro Asp Pro Tyr Thr Ser Ser
        195                 200                 205

Pro Glu Ser Ile Met Gly Tyr Ser Tyr Met Asp Ser Tyr Gln Thr Ser
    210                 215                 220

Ser Pro Ala Ser Ile Pro His Leu Ile Leu Glu Leu Leu Lys Cys Glu
225                 230                 235                 240

Pro Asp Glu Pro Gln Val Gln Ala Lys Ile Met Ala Tyr Leu Gln Gln
                245                 250                 255

Glu Gln Ala Asn Arg Ser Lys His Glu Lys Leu Ser Thr Phe Gly Leu
            260                 265                 270

Met Cys Lys Met Ala Asp Gln Thr Leu Phe Ser Ile Val Glu Trp Ala
        275                 280                 285

Arg Ser Ser Ile Phe Phe Arg Glu Leu Lys Val Asp Asp Gln Met Lys
    290                 295                 300

Leu Leu Gln Asn Cys Trp Ser Glu Leu Leu Ile Leu Asp His Ile Tyr
305                 310                 315                 320

Arg Gln Val Val His Gly Lys Glu Gly Ser Ile Phe Leu Val Thr Gly
                325                 330                 335

Gln Gln Val Asp Tyr Ser Ile Ile Ala Ser Gln Ala Gly Ala Thr Leu
            340                 345                 350

Asn Asn Leu Met Ser His Ala Gln Glu Leu Val Ala Lys Leu Arg Ser
        355                 360                 365

Leu Gln Phe Asp Gln Arg Glu Phe Val Cys Leu Lys Phe Leu Val Leu
    370                 375                 380

Phe Ser Leu Asp Val Lys Asn Leu Glu Asn Phe Gln Leu Val Glu Gly
385                 390                 395                 400

Val Gln Glu Gln Val Asn Ala Ala Leu Leu Asp Tyr Thr Met Cys Asn
                405                 410                 415

Tyr Pro Gln Gln Thr Glu Lys Phe Gly Gln Leu Leu Leu Arg Leu Pro
            420                 425                 430

Glu Ile Arg Ala Ile Ser Met Gln Ala Glu Glu Tyr Leu Tyr Tyr Lys
        435                 440                 445

His Leu Asn Gly Asp Val Pro Tyr Asn Asn Leu Leu Ile Glu Met Leu
    450                 455                 460

His Ala Lys Arg Ala
465
```

<210> SEQ ID NO 87
<211> LENGTH: 1277
<212> TYPE: DNA
<213> ORGANISM: Homo sapiens

<400> SEQUENCE: 87

```
tttttttcaa tgaacatgac ttctggagtc aaggttgttg ggccattccc cccgttccac      60

tcactgggaa tataaatagc acccacagcg cagaacacag agccagagag ctggaagtga     120

gagcagatcc ctaaccatga gcaccagcca accaggggcc tgcccatgcc agggagctgc     180

aagccgcccc gccattctct acgcacttct gagctccagc ctcaaggctg tccccccgacc     240

ccgtagccgc tgcctatgta ggcagcaccg gcccgtccag ctatgtgcac ctcatcgcac     300

ctgccgggag gccttggatg ttctggccaa gacagtggcc ttcctcagga acctgccatc     360

cttctggcag ctgcctcccc aggaccagcg gcggctgctg cagggttgct ggggcccccct     420

cttcctgctt gggttggccc aagatgctgt gacctttgag gtggctgagg ccccggtgcc     480
```

```
cagcatactc aagaagattc tgctggagga gcccagcagc agtggaggca gtggccaact    540

gccagacaga ccccagccct ccctggctgc ggtgcagtgg cttcaatgct gtctggagtc    600

cttctggagc ctggagctta gccccaagga atatgcctgc ctgaaaggga ccatcctctt    660

caaccccgat gtgccaggcc tccaagccgc ctcccacatt gggcacctgc agcaggaggc    720

tcactgggtg ctgtgtgaag tcctggaacc ctggtgccca gcagcccaag gccgcctgac    780

ccgtgtcctc ctcacggcct ccaccctcaa gtccattccg accagcctgc ttggggacct    840

cttctttcgc cctatcattg gagatgttga catcgctggc cttcttgggg acatgctttt    900

gctcaggtga cctgttccag cccaggcaga gatcaggtgg gcagaggctg gcagtgctga    960

ttcagcctgg ccatccccag aggtgaccca atgctcctgg agggggcaag cctgtataga   1020

cagcacttgg ctccttagga acagctcttc actcagccac accccacatt ggacttcctt   1080

ggtttggaca cagtgttcca gctgcctggg aggcttttgg tggtccccac agcctctggg   1140

ccaagactcc tgtcccttct tgggatgaga atgaaagctt aggctgctta ttggaccaga   1200

agtcctatcg actttataca gaactgaatt aagttattga tttttgtaat aaaaggtatg   1260

aaacacttgg aaaaaaa                                                  1277


<210> SEQ ID NO 88
<211> LENGTH: 257
<212> TYPE: PRT
<213> ORGANISM: Homo sapiens

<400> SEQUENCE: 88

Met Ser Thr Ser Gln Pro Gly Ala Cys Pro Cys Gln Gly Ala Ala Ser
1               5                   10                  15

Arg Pro Ala Ile Leu Tyr Ala Leu Leu Ser Ser Ser Leu Lys Ala Val
            20                  25                  30

Pro Arg Pro Arg Ser Arg Cys Leu Cys Arg Gln His Arg Pro Val Gln
        35                  40                  45

Leu Cys Ala Pro His Arg Thr Cys Arg Glu Ala Leu Asp Val Leu Ala
    50                  55                  60

Lys Thr Val Ala Phe Leu Arg Asn Leu Pro Ser Phe Trp Gln Leu Pro
65                  70                  75                  80

Pro Gln Asp Gln Arg Arg Leu Leu Gln Gly Cys Trp Gly Pro Leu Phe
                85                  90                  95

Leu Leu Gly Leu Ala Gln Asp Ala Val Thr Phe Glu Val Ala Glu Ala
            100                 105                 110

Pro Val Pro Ser Ile Leu Lys Lys Ile Leu Leu Glu Glu Pro Ser Ser
        115                 120                 125

Ser Gly Gly Ser Gly Gln Leu Pro Asp Arg Pro Gln Pro Ser Leu Ala
    130                 135                 140

Ala Val Gln Trp Leu Gln Cys Cys Leu Glu Ser Phe Trp Ser Leu Glu
145                 150                 155                 160

Leu Ser Pro Lys Glu Tyr Ala Cys Leu Lys Gly Thr Ile Leu Phe Asn
                165                 170                 175

Pro Asp Val Pro Gly Leu Gln Ala Ala Ser His Ile Gly His Leu Gln
            180                 185                 190

Gln Glu Ala His Trp Val Leu Cys Glu Val Leu Glu Pro Trp Cys Pro
        195                 200                 205

Ala Ala Gln Gly Arg Leu Thr Arg Val Leu Leu Thr Ala Ser Thr Leu
    210                 215                 220

Lys Ser Ile Pro Thr Ser Leu Leu Gly Asp Leu Phe Phe Arg Pro Ile
```

```
225                 230                 235                 240

Ile Gly Asp Val Asp Ile Ala Gly Leu Leu Gly Asp Met Leu Leu Leu
                245                 250                 255

Arg


<210> SEQ ID NO 89
<211> LENGTH: 1353
<212> TYPE: DNA
<213> ORGANISM: Mus musculus

<400> SEQUENCE: 89

gaggtgaaac cgtccctagg tgagccgtct ttccaccagg cccccggctc ggggtgccca      60

ccttccccat ggctggacac ctggcttcag acttcgcctt ctcaccccca ccaggtgggg     120

gtgatgggtc agcagggctg gagccgggct gggtggatcc tcgaacctgg ctaagcttcc     180

aagggcctcc aggtgggcct ggaatcggac caggctcaga ggtattgggg atctccccat     240

gtccgcccgc atacgagttc tgcggaggga tggcatactg tggacctcag gttggactgg     300

gcctagtccc ccaagttggc gtggagactt tgcagcctga gggccaggca ggagcacgag     360

tggaaagcaa ctcagaggga acctcctctg agccctgtgc cgaccgcccc aatgccgtga     420

agttggagaa ggtggaacca actcccgagg agtcccagga catgaaagcc ctgcagaagg     480

agctagaaca gtttgccaag ctgctgaagc agaagaggat caccttgggg tacacccagg     540

ccgacgtggg gctcaccctg ggcgttctct ttggaaaggt gttcagccag accaccatct     600

gtcgcttcga ggccttgcag ctcagcctta agaacatgtg taagctgcgg cccctgctgg     660

agaagtgggt ggaggaagcc gacaacaatg agaaccttca ggagatatgc aaatcggaga     720

ccctggtgca ggcccggaag agaaagcgaa ctagcattga gaaccgtgtg aggtggagtc     780

tggagaccat gtttctgaag tgcccgaagc cctccctaca gcagatcact cacatcgcca     840

atcagcttgg gctagagaag gatgtggttc gagtatggtt ctgtaaccgg cgccagaagg     900

gcaaaagatc aagtattgag tattcccaac gagaagagta tgaggctaca gggacacctt     960

tcccaggggg ggctgtatcc tttcctctgc cccaggtccc ccactttggc accccaggct    1020

atggaagccc ccacttcacc acactctact cagtcccttt tcctgagggc gaggcctttc    1080

cctctgttcc cgtcactgct ctgggctctc ccatgcattc aaactgaggc accagccctc    1140

cctggggatg ctgtgagcca aggcaaggga ggtagacaag agaacctgga gctttggggt    1200

taaattcttt tactgaggag ggattaaaag cacaacaggg gtggggggtg ggatggggaa    1260

agaagctcag tgatgctgtt gatcaggagc ctggcctgtc tgtcactcat cattttgttc    1320

ttaaataaag actgggacac acagtagata gct                                 1353


<210> SEQ ID NO 90
<211> LENGTH: 352
<212> TYPE: PRT
<213> ORGANISM: Mus musculus

<400> SEQUENCE: 90

Met Ala Gly His Leu Ala Ser Asp Phe Ala Phe Ser Pro Pro Pro Gly
1               5                   10                  15

Gly Gly Asp Gly Ser Ala Gly Leu Glu Pro Gly Trp Val Asp Pro Arg
            20                  25                  30

Thr Trp Leu Ser Phe Gln Gly Pro Pro Gly Gly Pro Gly Ile Gly Pro
        35                  40                  45

Gly Ser Glu Val Leu Gly Ile Ser Pro Cys Pro Pro Ala Tyr Glu Phe
```

```
    50                  55                  60

Cys Gly Gly Met Ala Tyr Cys Gly Pro Gln Val Gly Leu Gly Leu Val
65                  70                  75                  80

Pro Gln Val Gly Val Glu Thr Leu Gln Pro Glu Gly Gln Ala Gly Ala
                85                  90                  95

Arg Val Glu Ser Asn Ser Glu Gly Thr Ser Ser Glu Pro Cys Ala Asp
            100                 105                 110

Arg Pro Asn Ala Val Lys Leu Glu Lys Val Glu Pro Thr Pro Glu Glu
        115                 120                 125

Ser Gln Asp Met Lys Ala Leu Gln Lys Glu Leu Glu Gln Phe Ala Lys
    130                 135                 140

Leu Leu Lys Gln Lys Arg Ile Thr Leu Gly Tyr Thr Gln Ala Asp Val
145                 150                 155                 160

Gly Leu Thr Leu Gly Val Leu Phe Gly Lys Val Phe Ser Gln Thr Thr
                165                 170                 175

Ile Cys Arg Phe Glu Ala Leu Gln Leu Ser Leu Lys Asn Met Cys Lys
            180                 185                 190

Leu Arg Pro Leu Leu Glu Lys Trp Val Glu Glu Ala Asp Asn Asn Glu
        195                 200                 205

Asn Leu Gln Glu Ile Cys Lys Ser Glu Thr Leu Val Gln Ala Arg Lys
    210                 215                 220

Arg Lys Arg Thr Ser Ile Glu Asn Arg Val Arg Trp Ser Leu Glu Thr
225                 230                 235                 240

Met Phe Leu Lys Cys Pro Lys Pro Ser Leu Gln Gln Ile Thr His Ile
                245                 250                 255

Ala Asn Gln Leu Gly Leu Glu Lys Asp Val Val Arg Val Trp Phe Cys
            260                 265                 270

Asn Arg Arg Gln Lys Gly Lys Arg Ser Ser Ile Glu Tyr Ser Gln Arg
        275                 280                 285

Glu Glu Tyr Glu Ala Thr Gly Thr Pro Phe Pro Gly Gly Ala Val Ser
    290                 295                 300

Phe Pro Leu Pro Pro Gly Pro His Phe Gly Thr Pro Gly Tyr Gly Ser
305                 310                 315                 320

Pro His Phe Thr Thr Leu Tyr Ser Val Pro Phe Pro Glu Gly Glu Ala
                325                 330                 335

Phe Pro Ser Val Pro Val Thr Ala Leu Gly Ser Pro Met His Ser Asn
            340                 345                 350


<210> SEQ ID NO 91
<211> LENGTH: 4391
<212> TYPE: DNA
<213> ORGANISM: Mus musculus

<400> SEQUENCE: 91

agaggacagt ttgaaagaga ggaaggcaga gaagggacct gggaggaggc aggaggaggg      60

cggggacggg gggggctggg gctcagccca ggggcttggg tggcatcctg ggccgggcag     120

gacagggggc taaggcgtgg gtaggggaga atgcgactct ctaaaaccct tgccggcatg     180

gatatggccg actacagcgc tgccctggac ccagcctaca ccaccctgga gtttgaaaat     240

gtgcaggtgt tgaccatggg caatgacacg tccccatctg aaggtgccaa cctcaattca     300

tccaacagcc tgggcgtcag tgccctgtgc gccatctgtg gcgaccgggc caccggcaaa     360

cactacggag cctcgagctg tgacggctgc aaggggttct tcaggaggag cgtgaggaag     420

aaccacatgt actcctgcag gtttagccga caatgtgtgg tagacaaaga taagaggaac     480
```

```
cagtgtcgtt actgcaggct taagaagtgc ttccgggctg gcatgaagaa ggaagctgtc    540
caaaatgagc gggaccggat cagcacgcgg aggtcaagct acgaggacag cagcctgccc    600
tccatcaacg cgctcctgca ggcagaggtt ctgtcccagc agatcacctc tcccatctct    660
gggatcaatg gcgacattcg ggcaaagaag attgccaaca tcacagacgt gtgtgagtct    720
atgaaggagc agctgctggt cctggtcgag tgggccaagt acatcccggc cttctgcgaa    780
ctccttctgg atgaccaggt ggcgctgctc agggcccacg ccggtgagca tctgctgctt    840
ggagccacca agaggtccat ggtgtttaag gacgtgctgc tcctaggcaa tgactacatc    900
gtccctcggc actgtccaga gctagcggag atgagccgtg tgtccatccg catcctcgat    960
gagctggtcc tgcccttcca agagctgcag attgatgaca atgaatatgc ctgcctcaaa   1020
gccatcatct tctttgatcc agatgccaag gggctgagtg acccgggcaa gatcaagcgg   1080
ctgcggtcac aggtgcaagt gagcctggag gattacatca acgaccggca gtacgactct   1140
cggggccgct ttggagagct gctgctgctg ttgcccacgc tgcagagcat cacctggcag   1200
atgatcgaac agatccagtt catcaagctc ttcggcatgg ccaagattga caacctgctg   1260
caggagatgc ttctcggagg gtctgccagt gatgcacccc acacccacca cccccctgcac   1320
cctcacctga tgcaagaaca catgggcacc aatgtcattg ttgctaacac gatgccctct   1380
cacctcagca atggacagat gtgtgagtgg ccccgaccca gggggcaggc agccactccc   1440
gagactccac agccatcacc accaagtggc tcgggatctg aatcctacaa gctcctgcca   1500
ggagccatca ccaccatcgt caagcctccc tctgccattc cccagccaac gatcaccaag   1560
caagaagcca tctagcaagc tgctgggggg gtcaggggtt ctgctggctc ataccctcag   1620
aagagcacct gggagtaacc tagtcatggc aaagaagatg tgacacgagg gaccagtccc   1680
agagcagcta cagaaagggt gtgaggcccc aaaaccgtgt gctgaggggc gaatgcgtcg   1740
ccacccctga ccccgcatct ggagggcggg gctttgcttg agaagacccc agggaggact   1800
gtcttccact gcctggactc ctctcaagtt gaagtcatcg tcttcatctt cctccgtatc   1860
ttcttccctc aacttcttca cccctgaagg acgactgtct gcagatgttg caggaccttg   1920
ttttaaaatc aactcccttc tctcccagcg gggggcctct tccttcctgg tgctggtcag   1980
ggggcctgga aacaaacttt ctgaggctgg gtcagcttgc cttatagtac tcctctcctg   2040
ctatgccaac ctcaggtgac ctgctaccat cctctatacc ttcctccgcc atctgacttc   2100
tctaaagcca tctctctgga ggctgaggaa gctgtggtaa ccatttcccc actcattctg   2160
agagccttct gtaagcactg acctgggtaa ggcagagggt aggagtcacc atccctcctc   2220
tgccaatatc gctacaactc ctgcctccag cactaggcta taactttgga gtgataagtc   2280
ctatggcttt ctacagtaga gaaccaccca agggtgtcga ttataacaga atgtggagag   2340
tgggtggccg tcattgggaa agcatcgaga aagaggcgag ctttgcatct gtcccttgac   2400
agggaaggta ggcttctggc tagcagagca ggtgacacaa accagtttat tggagaacag   2460
cctggacaaa ggcccatagg taggtaaaat agtatgggag ggaggcaatg aagaaatcag   2520
ttcccatgga gttgtgacag ggtacacact ggggaccatt gaatgacaaa ctgaggtcag   2580
gggtagctgc agtgtggggc tgtcagaaga tgaatacagc atcccgcaga ggtaggatat   2640
gaggaggcta tactggagcg tagggatgag ataaagggat ggatccgagt cctcccgggg   2700
cctgccaagc ttttccatac ttccagatga tgttataagg cattaaacag ccaccatcgc   2760
atagaacctt ccctgtaacc cagacattgt caaggaagat atacgtagag gatcttaact   2820
```

```
gactcacagg aagcacttgt ccccccctggc acggaatcca gagggttcct cgtcctttac   2880

cagtgtcaac cccagaggct ttctctctcc agaactggcc agctagagac cgttctaaag   2940

tccactggaa gtcaagaatc tcgtttactg ataatagtaa agttgattca tgacccctgt   3000

cctttttttt ctactgatct acccaagtgt aggtgagccg cagcagggag tgattcctag   3060

aagacggatc agtctagtct ggcagtcaag gctcaggagt ttgggagagg ggcaggagaa   3120

ggataagaaa gcctgggttt taggcttgcc tgggaagcta cagtcaaggt gcattctggg   3180

agctactcat ccccagcagt tagcgctccg ccccggttga ctcttgatgg ctttgcggag   3240

cccctgcaaa gtgtcactag tcaatgggaa caagaggaat gtcccctggt ctggaagtgt   3300

gctaagtgga aggaatgggc tgtgagactg gatagttatg gtgcatcaag gctgatcctt   3360

ctgattgggt ggggcgagca tcccagtgtc caaaaattcc agcctaaatg acaggtcctc   3420

tgaaaaagag gtgctgagga gtaatggggc cagctgatta aagaaaaaga acccccacac   3480

aacaggactg tcaggacaga ttgagttaac ccctcaagcc aagtcccggg tgtcaggaac   3540

agttgtccat gctcagagcc ctcaagccat ccttggccac tctcactcca gtgcccccca   3600

gagaccccag ccagatggct cagactgtcc tgcatgaagg caggagagct gaactctctc   3660

tggtccttgt ctttcccaat ctttgtccct ccatccccag tggcatcagg agaggagtag   3720

gtaatgttgg ccttcagtgg tagcagtctt ctggggcagg ggtcagccac tgtcccaatc   3780

agtcctttct gaaggagaaa cccattccac attaacaaat ttattacagt acagggaaca   3840

tggaataaag gaaagtttac tcttctgatt ataagctgag gatgctatgt tgcagtttgt   3900

ttgcttgttt ttttcttctg agctttgttt ctagtacacg atatgacggg accaagtaca   3960

agctggtggt ggacagagct gggtgccaca gttttccacc aagagcagcc tcttttcttc   4020

atggagttct cagaaccttt cagggttcag gaggctcccc tgagaataga caggagaggg   4080

tcagaagcag acgtcctcct tttcttgtga taaccacgct acttgccttt gctagagctc   4140

tctgtggcca accctgggaa atgctaatca tgaccttcac accaaacatt cagaagtagg   4200

ctgtgtccca tcagatcaat ctgcaccttc ctgtggttgt gcaaacatca cggggcccta   4260

ccctgatccc caaggcccca ccatcactgc ccaagggggt aaaaaagaga aaaagccctc   4320

aaaaacagtt cttactcctg tgttttagca aaaatttatc aaacaaaata aatggtactt   4380

atgtttcta a                                                          4391
```

```
<210> SEQ ID NO 92
<211> LENGTH: 474
<212> TYPE: PRT
<213> ORGANISM: Mus musculus

<400> SEQUENCE: 92

Met Arg Leu Ser Lys Thr Leu Ala Gly Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Ala Asn Leu
        35                  40                  45

Asn Ser Ser Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95
```

```
Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Gln Gln Ile Thr Ser Pro Ile Ser Gly Ile Asn Gly Asp Ile
                165                 170                 175

Arg Ala Lys Lys Ile Ala Asn Ile Thr Asp Val Cys Glu Ser Met Lys
            180                 185                 190

Glu Gln Leu Leu Val Leu Val Glu Trp Ala Lys Tyr Ile Pro Ala Phe
        195                 200                 205

Cys Glu Leu Leu Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Cys
        275                 280                 285

Leu Lys Ala Ile Ile Phe Phe Asp Pro Asp Ala Lys Gly Leu Ser Asp
    290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
        355                 360                 365

Leu Leu Gln Glu Met Leu Leu Gly Gly Ser Ala Ser Asp Ala Pro His
    370                 375                 380

Thr His His Pro Leu His Pro His Leu Met Gln Glu His Met Gly Thr
385                 390                 395                 400

Asn Val Ile Val Ala Asn Thr Met Pro Ser His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Ser Gly Ser Gly Ser Glu Ser Tyr Lys Leu
        435                 440                 445

Leu Pro Gly Ala Ile Thr Thr Ile Val Lys Pro Pro Ser Ala Ile Pro
    450                 455                 460

Gln Pro Thr Ile Thr Lys Gln Glu Ala Ile
465                 470
```

<210> SEQ ID NO 93
<211> LENGTH: 16
<212> TYPE: DNA
<213> ORGANISM: Artificial Sequence
<220> FEATURE:

-continued

```
<223> OTHER INFORMATION: NR5A2 binding site

<400> SEQUENCE: 93

aacgaccgac cttgag                                                16


<210> SEQ ID NO 94
<211> LENGTH: 18
<212> TYPE: DNA
<213> ORGANISM: Artificial Sequence
<220> FEATURE:
<223> OTHER INFORMATION: Gapdh for RT-PCR normalization 1

<400> SEQUENCE: 94

tgcccccatg tttgtgat                                              18


<210> SEQ ID NO 95
<211> LENGTH: 18
<212> TYPE: DNA
<213> ORGANISM: Artificial Sequence
<220> FEATURE:
<223> OTHER INFORMATION: Gapdh for RT-PCR normalization 2

<400> SEQUENCE: 95

tgtggtcatg agcccttc                                              18


<210> SEQ ID NO 96
<211> LENGTH: 16
<212> TYPE: DNA
<213> ORGANISM: Artificial Sequence
<220> FEATURE:
<223> OTHER INFORMATION: Element sequence in the hepatitis B virus gene

<400> SEQUENCE: 96

aacgaccgac cttgag                                                16
```

DIRECT CONVERSION METHOD OF SOMATIC CELL INTO HEPATIC STEM CELL, HEPATIC CELL, OR CHOLANGIOCYTE

CROSS-REFERENCE TO RELATED APPLICATIONS

This application claims the benefit of Korea Patent Application No. 10-2016-0096469 filed on Jul. 28, 2016 with the Korea Industrial Property Office, the entire disclosure of which is hereby incorporated by reference.

BACKGROUND OF THE INVENTION

1. Field of the Invention

The present invention relates to a composition for inducing direct conversion from a somatic cell into one or more kinds selected from the group consisting of an induced Hepatic stem cell (iHSC), a hepatocyte, and a cholangiocyte, and a method of direct conversion of a somatic cell into one or more kinds selected from the group consisting of an induced Hepatic stem cell, a hepatocyte, and a cholangiocyte, comprising introducing the composition into the somatic cell.

2. Description of the Related Art

In the conventional methods for differentiating a hepatocyte using embryonic stem cells and pluripotent stem cells, the hepatocyte can be prepared by establishing embryonic stem cells by disrupting embryo or reprogramming as a step of pluripotent stem cells from a somatic cell, followed by differentiation into a hepatocyte. However, the conventional methods have ethical problems occurring in the process of obtaining embryonic stem cells, and there is a problem that is a inefficient method, because when pluripotent stem cells are used, time, monetary costs and efforts of differentiation are required, and efficiency is low, and artificial regulation of differentiation potency is not easy.

In addition, the conventional methods of differentiation of a hepatocyte using embryonic stem cells and pluripotent stem cells have a problem that is a technique in which safety is not secured, because a sufficient number of cells required for drug metabolism and toxicity test at an in vitro level are difficult to obtained and there is a high probability that teratomas derived from undifferentiated cells can be formed during application step of cellular therapy for regeneration of liver function.

Therefore, the development of a technology of direct conversion from a somatic cell into a hepatic stem cell, a hepatocyte, a cholangiocyte has been required.

In addition, various cell resources used for conventional drug screening have the following problems and limitations. For example, mouse-derived primary culture hepatocytes are not cells derived from human, so it is difficult to verify effects of drugs, and human-derived primary culture hepatocytes have limitations in its restrictive securement, difficult proliferation and maintenance of function in vitro. In case of HepG2 and HepaRG derived from liver cancer cells, it is inappropriate for using in drug screening, because they are cells in which proliferation is possible in vitro, but differentiation potency into a cholangiocyte is not present or very low, and have inappropriate level of drug metabolism functions to test functions of drugs.

Therefore, a need to obtain cell resources which are suitable for drug screening has been issued.

SUMMARY OF THE INVENTION

A purpose of the present invention is to provide a composition for inducing direct conversion from a somatic cell into one or more kinds selected from the group consisting of an induced hepatic stem cell (iHSC), a hepatocyte, and a cholangiocyte comprising a direct conversion factor.

The direct conversion factor may be one or more kinds selected from the group consisting of (1) OCT4 protein, HNF4α protein, NR4A2 protein, NR4A1 protein, TBX3 protein, NR5A1 protein, NR5A2 protein, and NR0B2 protein (2) nucleic acid molecules encoding each of the proteins, and (3) vectors into which each of the nucleic acid molecules is introduced.

Another purpose of the present invention is to provide a method of direct conversion of a somatic cell into one or more kinds selected from a group consisting of a hepatic stem cell, a hepatocyte and a cholangiocyte, comprising a step of introducing the direct conversion factor into the somatic cell.

Other purpose of the present invention is to provide a pharmaceutical composition for preventing or treating a liver disease, comprising one or more kinds selected from the group consisting of hepatic stem cell, hepatocyte and cholangiocyte in which direct conversion is induced by the method, and hepatocyte and cholangiocyte in which differentiation is induced from the direct conversion-induced hepatic stem cell.

DETAILED DESCRIPTION

Figure 1:
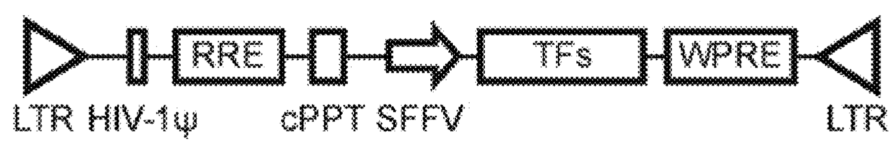
FIG. 1 shows a viral delivery system used for preparing hepatic stem cells.

In a specific example of the present invention, a direct conversion factor such as OCT4, HNF4 α, etc was introduced into a mouse fibroblast which was selected as a representative example of a somatic cell using lentivirus, thereby directly converting the fibroblast into a hepatic stem cell. Reverse transcription PCR was performed to confirm that markers of hepatocyte and cholangiocyte were negative in the fibroblast before introduction of the direct conversion factor.

In another example, the induced hepatic stem cell was differentiated into a hepatocyte and a cholangiocyte. It was demonstrated that the hepatocyte and cholangiocyte differentiated from the hepatic stem cell normally functioned by confirming drug metabolism, glycogen storage function, detoxification function, fat absorption function of the hepatocyte, and in vitro secretion function of the cholangiocyte.

In addition, it was confirmed that it can be used as an in vitro alcoholic fatty liver disease model using the induced hepatic stem cell or the hepatocyte differentiated from the induced hepatic stem cell by performing Oil Red O staining and Bodipy fluorescence staining.

In addition, it was confirmed that the hepatocyte had a treatment effect of inhibiting a hepatic fibrosis phenomenon by injecting the induced hepatic stem cell or the hepatocyte differentiated from the induced hepatic stem cell.

Hereinafter, the present invention will be described in more detail.

One embodiment of the present invention relates to a composition for inducing direct conversion from a somatic cell into one or more kinds selected from the group consisting of a hepatic stem cell, a hepatocyte and a cholangiocyte comprising a direct conversion factor.

Other embodiment relates to a method of direct conversion of a somatic cell into one or more kinds selected from the group consisting of a hepatic stem cell, a hepatocyte and a cholangiocyte, comprising a step of introducing a direct conversion factor into the somatic cell. The method may be conducted in vivo or in vitro, and for example, may be conducted outside a human body.

The direct conversion factor used in the composition for inducing direct conversion and the method of direct conversion provided in the present description may be one or more kinds selected from the group consisting of (1) OCT4 protein, HNF4α protein, NR4A2 protein, NR4A1 protein, TBX3 protein, NR5A1 protein, NR5A2 protein, and NR0B2 protein (2) nucleic acid molecules encoding each of the proteins, and (3) vectors into which each of the nucleic acid molecules is introduced.

In one specific example, the direct conversion factor may comprise one or more selected from the group consisting of OCT4 protein, HNF4α protein, NR4A2 protein, NR4A1 protein, TBX3 protein, NR5 A1 protein, NR5A2 protein, NR0B2 protein, a nucleic acid molecule encoding OCT4 protein, a nucleic acid molecule encoding HNF4α protein, a nucleic acid molecule encoding NR4A2 protein, a nucleic acid molecule encoding NR4A1 protein, a nucleic acid molecule encoding TBX3 protein, a nucleic acid molecule encoding NR5A1 protein, a nucleic acid molecule encoding NR5A2 protein, a nucleic acid molecule encoding NR0B2 protein, a vector into which the nucleic acid molecule encoding OCT4protein is introduced, a vector into which the nucleic acid molecule encoding HNF4α protein is introduced, a vector into which the nucleic acid molecule encoding NR4A2 protein is introduced, a vector into which the nucleic acid molecule encoding NR4A1 protein is introduced, a vector into which the nucleic acid molecule encoding TBX3 protein is introduced, a vector into which the nucleic acid molecule encoding NR5A1 protein is introduced, a vector into which the nucleic acid molecule encoding NR5A2 protein is introduced, and a vector into which the nucleic acid molecule encoding NR0B2 protein is introduced.

In other specific example, the direct conversion factor may comprise (a) one or more kinds of selected from the group consisting of OCT4 protein, a nucleic acid molecule encoding OCT4 protein, and a vector into which the nucleic acid molecule encoding OCT4 protein is introduced, and (b) one or more kinds selected from the group consisting of HNF4α protein, NR4A1 protein, NR4A2 protein, a nucleic acid molecule encoding HNF4α protein, a nucleic acid molecule encoding NR4A1 protein, a nucleic acid molecule encoding NR4A2 protein, a vector into which the nucleic acid molecule encoding HNF4α protein is introduced, a vector into which the nucleic acid molecule encoding NR4A1 protein is introduced, and a vector into which the nucleic acid molecule encoding NR4A2 protein is introduced.

In other specific example, the direct conversion factor may further comprise (c) one or more kinds selected from the group consisting of TBX3 protein, NR5A1 protein, NR5A2 protein, NR0B2 protein, a nucleic acid molecule encoding TBX3 protein, a nucleic acid molecule encoding NR5A1 protein, a nucleic acid molecule encoding NR5A2 protein, a nucleic acid molecule encoding NR0B2 protein, a vector into which the nucleic acid molecule encoding TBX3 protein is introduced, a vector into which the nucleic acid molecule encoding NR5A1 protein is introduced, a vector into which the nucleic acid molecule encoding NR5A2 protein is introduced, and a vector into which the nucleic acid molecule encoding NR0B2 protein is introduced, in addition to the (a) and (b).

The direct conversion factor can obtain an additional effect with a further improved direct conversion speed, by further comprising (c) in addition to the (a) and (b).

The OCT4 (octamer-binding transcription factor 4) protein, also known as POU5F1 protein, is encoded by POU5F1 gene. OCT4 is one of homeodomain transcription factors of POU family. OCT4 protein is known to be involved in autotomy of undifferentiated embryonic stem cells, but the content related to direct conversion from a somatic cell into a hepatic stem cell, a hepatocyte, or a cholangiocyte is not known at all. The gene sequence of human OCT4 of SEQ ID NO: 73 is known as NM_002701.5. (NCBI) and the amino acid sequence of human OCT4 protein of SEQ ID NO: 74 is known as NP_002692.2. (NCBI), respectively. The corresponding gene sequence of mouse OCT4 is NM_013633.3 (SEQ ID NO: 89), and the amino acid sequence of mouse OCT4 is NP_038661.2 (SEQ ID NO: 90).

The HNF4α (Hepatocyte nuclear factor 4-alpha) protein is a transcription factor which is regulated in the transcription stage, and is known to play an essential role in development process of liver, kidney and intestine. The gene sequence of human HNF4α of SEQ ID NO: 75 is known as NM_000457.4. (NCBI), and the amino acid sequence of human HNF4α protein of SEQ ID NO: 76 is known as NP_000448.3. (NCBI), respectively. The corresponding gene sequence of mouse HNF4α is NM_008261.3 (SEQ ID NO: 91), and the amino acid sequence of mouse HNF4α is NP_032287.2 (SEQ ID NO: 92).

The NR4A2 (Nuclear receptor subfamily 4 group A member 2) protein is known as a transcriptional regulator which plays an important role in differentiation and maintenance of meso-diencephalic dopaminergic (mdDA) neurons during development process, but the content related to direct conversion from a somatic cell into a hepatic stem cell, a hepatocyte, or a cholangiocyte is not known at all. The gene sequence of human NR4A2 of SEQ ID NO: 77 is known as NM_006186.3. (NCBI), and the amino acid sequence of human NR4A2 of SEQ ID NO: 78 is known as NP_006177.1. (NCBI), respectively.

The NR4A1 (Nuclear receptor subfamily 4 group A member 2) protein is an orphan nuclear receptor whose ligand is unknown, and it was known to regulate expression of delayed-early genes during liver regeneration, but the content related to direct conversion from a somatic cell into a hepatic stem cell, a hepatocyte, or a cholangiocyte is not known at all. The gene sequence of human NR4A1 of SEQ ID NO: 79 is known as NM_001202233.1. (NCBI), and the amino acid sequence of human NR4A1 of SEQ ID NO: 80 is known as NP_001189162.1. (NCBI), respectively.

The TBX3 (T-box transcription factor 3) is known to function as a transcriptional inhibitor during development process, but the content related to direct conversion from a somatic cell into a hepatic stem cell, a hepatocyte, or a cholangiocyte is not known at all. The gene sequence of human TBX3 of SEQ ID NO: 81 is known as NM_005996.3. (NCBI), and the amino acid sequence of human TBX3 of SEQ ID NO: 82 is known as NP_005987.3. (NCBI), respectively.

The NR5A1 (Nuclear receptor subfamily 5 group A member 1) is known as a transcriptional activator essential for sexual development, but the content related to direct conversion from a somatic cell into a hepatic stem cell, a hepatocyte, or a cholangiocyte is not known at all. The gene sequence of human NR5A1 of SEQ ID NO: 83 is known as NM_004959.4. (NCBI), and the amino acid sequence of human NR5A1 of SEQ ID NO: 84 is known as NP_004950.2. (NCBI), respectively.

The NR5A2 (Nuclear receptor subfamily 5 group A member 2 ) is known to play an important role in expression and regulation of cis-element by binding to 5'-AACGACCGACCTTGAG-3' (SEQ ID NO: 96) element sequence in the hepatitis B virus gene, but the content related to direct conversion from a somatic cell into a hepatic stem cell, a hepatocyte, or a cholangiocyte is not known at all. The gene sequence of human NR5A2 of SEQ ID NO: 85 is known as NM_001276464.1. (NCBI), and the amino acid sequence of human NR5A2 of SEQ ID NO: 86 is known as NP_001263393.1. (NCBI), respectively.

The NR0B2 (Nuclear receptor subfamily 0 group B member 1) is known to play an important role in maintaining pluripotency of embryonic stem cells and regulating embryonic development as an orphan nuclear receptor, but the content related to direct conversion from a somatic cell into a hepatic stem cell, a hepatocyte, or a cholangiocyte is not known at all. The gene sequence of human NR0B2 of SEQ ID NO: 87 is known as NM_021969.2. (NCBI), and the amino acid sequence of human NR0B2 of SEQ ID NO: 88 is known as NP_068804.1. (NCBI), respectively.

The OCT4, HNF4α, NR4A1, NR4A2, TBX3, NR5A1, NR5A2, and/or NR0B2 may be provided as a form of protein or nucleic acid encoding the protein. The OCT4, HNF4α, NR4A1, NR4A2, TBX3, NR5A1, NR5A2, and/or NR0B2 proteins may comprise all OCT4, HNF4α, NR4A1, TBX3, NR5A1, NR5A2, or NR0B2 derived from mammals such as human, horse, sheep, pig, goat, camel, antelope, dog, etc. In addition, the OCT4, HNF4α, NR4A1, NR4A2, TBX3, NR5A1, NR5A2, and/or NR0B2 proteins which can be used in the present invention may comprise not only proteins having amino acid sequences of their wild types but also variants of OCT4, HNF4α, NR4A1, NR4A2, TBX3, NR5A1, NR5A2, and/or NR0B2 proteins (for example, subtypes of each protein).

The variants of OCT4, HNF4α, NR4A1, NR4A2, TBX3, NR5A1, NR5A2, and/or NR0B2 proteins means proteins have a sequence different from a natural amino acid sequence by deletion, insertion, non-conserved or conserved substitution or combinations thereof of one or more amino acid residues of the natural amino acid and maintain native biological functions of the natural (wild-type) protein. The variants may be functional equivalents exhibiting the same biological activity as the natural protein or variants in which physicochemical properties of the protein is modified by necessity, and may be variants in which structural stability against physical or chemical environment is increased or physiological activity is increased.

The OCT4, HNF4α, NR4A1, NR4A2, TBX3, NR5A1, NR5A2, and/or NR0B2 proteins or their variants may be isolated form nature, or recombinantly or synthetically produced (non-naturally occurring).

In addition, nucleic acids encoding the OCT4, HNF4α, NR4A1, NR4A2, TBX3, NR5A1, NR5A2, and/or NR0B2 protein are base sequences encoding wild type or aforementioned variant form of OCT4, HNF4α, NR4A1, NR4A2, TBX3, NR5A1, NR5A2, and/or NR0B2 proteins, and may be varied by substitution, deletion, insertion or combination thereof of one or more bases, and may be isolated from nature or prepared by using a chemical synthetic method. The nucleic acids having base sequences encoding the OCT4, HNF4α, NR4A1, NR4A2, TBX3, NR5A1, NR5A2, and/or NR0B2 proteins may be single strand or double strand, and may be DNA molecule (genome, cDNA) or RNA (mRNA) molecule.

As one specific example of the present invention, in the present invention, nucleic acid molecules encoding OCT4, HNF4α, NR4A1, NR4A2, TBX3, NR5A1, NR5A2, and/or NR0B2 proteins may be used as inserted into a vector expressing OCT4, HNF4α, NR4A1, NR4A2, TBX3, NR5A1, NR5A2, and/or NR0B2 proteins comprising nucleic acids encoding OCT4, HNF4α, NR4A1, NR4A2, TBX3, NR5A1, NR5A2, and/or NR0B2 proteins.

In the present invention, "vector" is an expression vector which is capable of expressing a targeted protein in an appropriate host cell, and may means a gene transporter comprising an essential regulatory element operable linked to express gene inserts.

The vector of the present invention may comprise a signal sequence or a leader sequence for membrane targeting or secretion, in addition to an expression regulatory element such as a promoter, an operator, an initiation codon, a stop codon, a polyadenylation signal, an enhancer and the like, and be prepared variously according to purposes. The promoter of the vector may be constitutive or inducible. In addition, the expression vector comprises a selective marker for selecting a host cell containing a vector, and comprises a replication origin in case of replicable expression vector. The vector may be self-replicated or integrated into host DNA.

The vector comprises plasmid vector, cosmid vector, virus vector, etc. Preferably, it is virus vector. The virus vector comprises Lentivirus vector, and vectors derived from Retrovius, for example, HIV (Human immunodeficiency virus), MLV (Murineleukemia virus) ASLV (Avian sarcoma/leukosis), SNV (Spleen necrosis virus), RSV (Rous sarcoma virus), MMTV (Mouse mammary tumor virus), etc, Adenovirus, Adeno-associated virus, Herpes simplex virus, etc, but not limited thereto. Such a vector system is used for the purpose of inducing direct conversion by overexpressing a gene related to a specific cell in a somatic cell, so that any vector system can exhibit the effect of the present invention.

As a specific example of the present invention, it may be Lentivirus vector expressing aforementioned direct conversion-inducing factors, but not limited thereto (FIG. 1).

In addition, the nucleic acid encoding OCT4 protein, the nucleic acid encoding HNF4α protein, the nucleic acid encoding NR4A2 protein, the nucleic acid encoding NR4A1 protein, the nucleic acid encoding TBX3 protein, the nucleic acid encoding NR5A1 protein, the nucleic acid encoding NR5A2 protein, and the nucleic acid encoding NR0B2 protein may be delivered into cells by known methods in the art, for example, as naked DNA in the form of a vector, or be delivered into cells using liposome, cationic polymer, etc. Liposome is a phospholipid membrane prepared by mixing cationic phospholipids such as DOTMA or DOTAP, etc for gene delivery, and a nucleic acid-liposome complex may be formed, if cationic liposome and anionic nucleic acid are mixed at a certain ratio.

In the present invention, the nucleic acid encoding OCT4 protein, the nucleic acid encoding HNF4α protein, the nucleic acid encoding NR4A2 protein, the nucleic acid encoding NR4A1 protein, the nucleic acid encoding TBX3 protein, the nucleic acid encoding NR5A1 protein, the nucleic acid encoding NR5A2 protein, and the nucleic acid encoding NR0B2 protein may be introduced into a somatic cell as comprised in a vector (for example, virus vector) prepared to express OCT4 protein, NR4A2 protein, HNF4α protein, NR4A1 protein, TBX3 protein, NR5A1 protein, NR5A2 protein, and NR0B2 protein, by transforming and infecting a virus vector comprising the nucleic acid encoding OCT4 protein, the nucleic acid encoding HNF4α protein, the nucleic acid encoding NR4A2 protein, the nucleic acid encoding NR4A1 protein, the nucleic acid encoding TBX3 protein, the nucleic acid encoding NR5A1 protein, the nucleic acid encoding NR5A2 protein, and the nucleic acid encoding NR0B2 protein with a packaging cell. For example, a virus vector which can be applied to the present invention comprises Retrovirus, Adenovirus, Adeno-associated virus, Herpes simplex virus vector, etc, but not limited thereto.

By direct conversion induced in a composition for inducing direct conversion and a method of direct conversion that are provided in one example of the present invention, induction of transdifferentiation from a somatic cell into a hepatic stem cell, a hepatocyte and/or a cholangiocyte is possible.

By direct conversion induced in a composition for inducing direct conversion and a method of direct conversion that are provided in other example, transdifferentiation from a somatic cell into a hepatic stem cell is induced, and here again may be differentiated into a hepatocyte and/or a cholangiocyte. In this case, the method of direct conversion may further comprise a step of differentiating the hepatic stem cell obtained by introducing aforementioned direct conversion factor into a somatic cell into a hepatocyte and/or a cholangiocyte, and the step of differentiating the hepatic stem cell into a hepatocyte and/or a cholangiocyte may be conducted by applying a common differentiation technology.

In the present invention, the term "somatic cell" may mean all cells except reproductive cells, and for example, may be derived or isolated from mammals such as human, horse, sheep, pig, goat, camel, antelope, and dog. For example, the somatic cell may be one selected from the group consisting of fibroblast, epithelial cell, muscle cell, neural cell, hair cell, dermal papilla cell, hair follicular cell, oral epithelial cell, somatic cell extracted from urine, gastric mucosal cell, goblet cell, G cell, B cell, pericyte, astrocyte, blood cell, neural stem cell, hematopoietic stem cell, mesenchymal stem cell, etc, but not limited thereto, because it can be applied regardless of a specific tissue cell, if a starting cell is a somatic cell. In a specific example of the present invention, a dermal fibroblast derived from a mouse tail or human fibroblast was used.

The term "hepatic stem cell" means a cell having the potential to differentiate into a hepatocyte and a cholangiocyte. The hepatic stem cell may differentiate a hepatocyte producing albumin and a cholangiocyte which is cytokeratin 19 positive. In addition, in the present invention, "iHSC (induced hepatic stem cell)" means a hepatic stem cell which is induced, and for example, may mean a hepatic stem cell induced from a somatic cell through direct conversion according to the method of the present invention.

The term "hepatocyte" means a cell constituting parenchymal tissue of liver. It is about 20 um in size, and is involved in synthesis and storage of proteins, conversion of carbohydrates, synthesis of cholesterol, bile acids, and phospholipids, detoxification, degeneration, and excretion of endogenous and exogenous substances, and acts to promote production and secretion of bile. In addition, in the present invention, "iHep" means induced hepatocyte, and for example, may mean a hepatocyte induced from a somatic cell through direct conversion according to the method of the present invention or a hepatocyte differentiated from the induced hepatic stem cell.

In one example of the present invention, it was confirmed that direct conversion from a somatic cell into a hepatic stem cell and a hepatocyte was induced by introducing a direct conversion factor into a human somatic cell (fibroblast) (Examples 6-1 and 6-2), and it was confirmed that it had normal properties of the hepatocyte by conducting analysis of properties of the direct conversion-induced hepatocyte from the somatic cell (Example 6-3).

In one example of the present invention, the direct conversion factor used for inducing direct conversion from a human somatic cell into a hepatic stem cell and a hepatocyte is human OCT4 (NM_002701.5, SEQ ID NO: 73) and HNF4α (NM_000457.4., SEQ ID NO: 75) (Example 1), or OU, OUT, ON7, or ON7T (O:OCT4, NM_002701.5., SEQ ID NO: 73); U:NR4A2/NURR1, NM_006186.3., SEQ ID NO: 77; N7:NR4A1/NUR77, NM_001202233.1., SEQ ID NO: 79; T:TBX3, NM_005996.3., SEQ ID NO: 81) (Example 6).

The term "cholangiocyte" means a bile duct epithelial cell. In a health liver, cholangiocytes function to secret bile. In addition, in the present invention, "cholangiocyte" means an induced cholangiocyte, and for example, may mean a cholangiocyte induced from a somatic cell through direct conversion according to the method of the present invention or a cholangiocyte differentiated from the induced hepatic stem cell.

In one example of the present invention, it was confirmed that direct conversion from a somatic cell into a cholangiocyte was induced by introducing a direct conversion factor into a human somatic cell (Example 5 and Example 6-4).

In one example of the present invention, the direct conversion factor used for inducing direct conversion from a somatic cell into a cholangiocyte is human OCT4 (NM_002701.5, SEQ ID NO: 73) and HNF4α (NM_000457.4., SEQ ID NO: 75) (Example 1), or OU, OUT, ON7, or ON7T (O:OCT4, NM_002701.5., SEQ ID NO: 73); U:NR4A2/NURR1, NM_006186.3., SEQ ID NO: 77; N7:NR4A1/NUR77, NM_001202233.1., SEQ ID NO: 79; T:TBX3, NM_005996.3., SEQ ID NO: 81) (Example 6).

The term "direct conversion (direct reprogramming, transdifferentiation)" is a process inducing conversion between mature (differentiation finished) cells having totally different cell types in a higher organism. This is different from a process of reprogramming into induced pluripotent stem cells (iPSCs) and redifferentiating them into targeted cells, in that it induces conversion into targeted cells directly without going through a stage of induced pluripotent stem cells. Currently, direct conversion is considered to be used for disease modeling and new drug discovery, etc, and is expected to be applied to gene therapy and regenerative medicine in the future.

As described above, one example of the present invention provides a method of direct conversion from a somatic cell into one or more kinds selected from the group consisting of a hepatic stem cell, a hepatocyte and a cholangiocyte, comprising a step of introducing the composition for inducing direct conversion into the somatic cell.

The method may further comprise a step of differentiation the hepatic stem cell produced by using the method of inducing direct conversion from a somatic cell into a hepatic stem cell into a hepatocyte or cholangiocyte.

In one specific example, the method of direct conversion may comprise a step of culturing a somatic cell in a medium, a step of transfection of one or more kinds selected from the group consisting of a vector in which OCT4 gene is inserted, a vector in which HNF4 α gene is inserted, a vector in which NR4A2 gene is inserted, a vector in which NR4A1 gene is inserted, a vector in which TBX3 gene is inserted, a vector in which NR5A1 gene is inserted, a vector in which NR5A2 gene is inserted, and a vector in which NR0B2 gene is inserted into the cultured somatic cell, and a step of culturing the transfected somatic cell under the culturing condition that direct conversion can be induced.

The medium used for culturing of the somatic cell comprises all media commonly used for culturing of a somatic cell in the art. The medium used for culturing generally comprises carbon source, nitrogen source, and trace element source. In a specific example of the present invention, a medium containing protamine sulfate was used, but not limited thereto.

In addition, the culturing condition that direct conversion of a somatic cell can be induced may comprise media commonly used for inducing direct conversion of a somatic cell in the art and/or common culturing conditions. In a specific example of the present invention, MEF medium (Dulbecco's modified Eagle's medium (DMEM, Invitrogen, 10313-021)) containing 10% (v/v) fetal bovine serum (FBS, Invitrogen), 2 mM L-Glutamine (Invitrogen, 25030-081), MEM Non-essential amino acid (NEAA, Gibco, 11140-050), 55 uM β-Mercaptoethanol (β-ME, Invitrogen, 21985-023) and Penicillin/Streptomycin (Invitrogen, 15140-122)) was used, but not limited thereto.

Through a step of introducing the composition for inducing direct conversion of the present invention into a somatic cell, ectopic expression of direct conversion factors such as OCT4, etc can be induced. The ectopic expression means that certain gene is expressed outside a tissue or a cell in which it is originally expressed, or that it is expressed at a period different from the originally expressed period. In a specific example of the present invention, the expression of one or more kinds selected from the group consisting of OCT4 protein, HNF4α protein, NR4A2 protein, NR4A1 protein, TBX3 protein, NR5A1 protein, NR5A2 protein, and NR0B2 protein may be induced in a somatic cell which does not express one or more kinds selected from the group consisting of OCT4 protein, HNF4α protein, NR4A2 protein, NR4A1 protein, TBX3 protein, NR5A1 protein, NR5A2 protein, and NR0B2 protein by introducing the composition for inducing into a somatic cell. Thereby, one or more kinds selected from the group consisting of a hepatic stem cell, a hepatocyte and a cholangiocyte can be prepared from the somatic cell.

The hepatic stem cell, hepatocyte and/or cholangiocyte prepared according to the present invention play an essential role in processes of production and secretion of bile, storage of proteins, detoxification, etc, and it can be applied to prevention or treatment of a disease caused by liver hypofunction and loss, since the directly converted hepatic stem cell can be differentiated into a hepatocyte and a cholangiocyte.

Therefore, as one embodiment of the present invention, a pharmaceutical composition for preventing or treating a liver disease comprising one or more kinds selected from the group consisting of differentiation-induced hepatic stem cell, hepatocyte and cholangiocyte by the composition or method directly converting a somatic cell into one or more kinds selected from the group consisting of a hepatic stem cell, a hepatocyte and a cholangiocyte as described above, and differentiation-induced hepatocyte and cholangiocyte from the direct conversion-induced hepatic stem cell.

The liver disease may be one or more selected from the group consisting of hepatic fibrosis, liver cirrhosis, hepatitis (for example, B-type hepatitis, C-type hepatitis), liver cancer, alcoholic fatty liver, nonalcoholic fatty liver, hyperhomocysteinemia and related cardiocerebrovascular disease, thrombosis, atherosclerosis, etc, but not limited thereto, and may comprise all diseases and/or pathological symptoms caused by hypofunction, loss and/or abnormal function of liver.

As another embodiment, the present invention provides a method for preventing or treating a liver disease comprising a step of administrating one or more selected from the group consisting of direct conversion-induced hepatic stem cell, hepatocyte and cholangiocyte, and differentiation-induced hepatocyte and cholangiocyte from the directly converted hepatic stem cell, wherein the direct conversion-induced hepatic stem cell, hepatocyte and cholangiocyte are prepared by introducing a composition for inducing direct conversion comprising one or more kinds selected from the group consisting of (1) OCT4 protein, HNF4α protein, NR4A2 protein, NR4A1 protein, TBX3 protein, NR5A1 protein, NR5A2 protein, and NR0B2 protein (2) nucleic acid molecules encoding each of the proteins, and (3) vectors into which each of the nucleic acid molecules is introduced into a somatic cell, thereby inducing direct conversion.

The composition for inducing direct conversion may comprise one or more selected from the group consisting of OCT4 protein, a nucleic acid molecule encoding OCT4 protein, and a vector into which the nucleic acid molecule encoding OCT4 protein is introduced, and one or more kinds selected from the group consisting of HNF4α protein, NR4A1 protein, NR4A2 protein, a nucleic acid molecule encoding HNF4α protein, a nucleic acid molecule encoding NR4A1 protein, a nucleic acid molecule encoding NR4A2 protein, a vector into which the nucleic acid molecule encoding HNF4α protein is introduced, a vector into which the nucleic acid molecule encoding NR4A1 protein is introduced, and a vector into which the nucleic acid molecule encoding NR4A2 protein is introduced.

In addition, the composition for inducing direct conversion may further comprise one or more kinds selected from the group consisting of TBX3 protein, NR5A1 protein, NR5A2 protein, NR0B2 protein, a nucleic acid molecule encoding TBX3 protein, a nucleic acid molecule encoding NR5A1 protein, a nucleic acid molecule encoding NR5A2 protein, a nucleic acid molecule encoding NR0B2 protein, a vector into which the nucleic acid molecule encoding TBX3 protein is introduced, a vector into which the nucleic acid molecule encoding NR5A1 protein is introduced, a vector into which the nucleic acid molecule encoding NR5A2 protein is introduced, and a vector into which the nucleic acid molecule encoding NR0B2 protein is introduced.

The direct conversion-induced hepatic stem cell may be differentiated into a hepatocyte or a cholangiocyte.

A subject of the prevention and/or treatment may be a mammal, for example, a primate including human, a monkey, etc, a rodent including a mouse, a rat, etc, or a pet animal including dog family, cat family, etc, or a cell or tissue isolated from the living body thereof. In one example, the subject may be a mammal, for example, a primate including human, a monkey, etc, a rodent including a mouse, a rat, etc, or a pet animal including dog family, cat family, etc, which suffers a liver disease, for example hepatic fibrosis, or a cell or tissue isolated from the living body thereof.

One or more kinds selected from the group consisting of the direct conversion-induced hepatic stem cell, hepatocyte and cholangiocyte, and differentiation-induced hepatocyte and cholangiocyte from the directly converted hepatic stem cell, which are administered to a patient, may be administered orally or parenterally. In case of parenteral administration, it may be administered by intravenous injection, subcutaneous injection, muscle injection, intraperitoneal injection, endothelial administration, topical administration, intranasal administration, intrapulmonary administration, intrasplenic or intrarectal administration, etc.

In the present invention, an effective dose of one or more kinds selected form the group consisting of the direct conversion-induced hepatic stem cell, hepatocyte and cholangiocyte, and differentiation-induced hepatocyte and cholangiocyte from the directly converted hepatic stem cell of the invention administering into a patient means a degree of exhibiting a significant effect of prevention or treatment of a liver disease. The effective dose for single administration may be prescribed variously depending on factors such as formulation method, administration method, age, body weight, sex, pathological condition of a patient, diet, administration time, administration interval, administration route, excretion rate and reaction sensitivity. Depending on judgment of a doctor or pharmacist, it may be administered once or several times a day at intervals of certain time. For example, the effective dose of one or more kinds selected form the group consisting of the direct conversion-induced hepatic stem cell, hepatocyte and cholangiocyte, and differentiation-induced hepatocyte and cholangiocyte from the directly converted hepatic stem cell may be $1\times10^7$ to $6\times10^9$ cell/kg, specifically $1\times10^7$ to $4\times10^8$ cell/kg, more specifically $1\times10^8$ to $4\times10^8$ cell/kg based on the weight of the subject to be administered, but not limited thereto. The effective dose for the single administration may be formulated as one formulation in a unit dosage form, or formulated in an appropriate amount, or prepared by injecting into a multi-dose container. The dosage is illustrative of the average case, and the dose may be high or low depending on individual differences.

One or more kinds selected from the group consisting of the direct conversion-induced hepatic stem cell, hepatocyte and cholangiocyte, and differentiation-induced hepatocyte and cholangiocyte from the directly converted hepatic stem cell, which are administered to a patient, may further comprise one or more kinds selected from the group consisting of a diluent, an excipient, a lubricant, an humectant, a sweetener, a flavor, an emulsifier, a suspending agent, a preservative and a buffer solution, etc.

As other embodiment, the present invention may be used as a composition for screening therapeutic agents of liver diseases comprising one or more kinds selected from the group consisting of the direct conversion-induced hepatic stem cell, hepatocyte and cholangiocyte, and differentiation-induced hepatocyte and cholangiocyte from the directly converted hepatic stem cell.

In other words, it may be usefully used for screening therapeutic agents of liver diseases in a method of confirming reactivity of one or more kinds selected from the group consisting of the direct conversion-induced hepatic stem cell, hepatocyte and cholangiocyte from a somatic cell, and differentiation-induced hepatocyte and cholangiocyte from the directly converted hepatic stem cell of the present invention in presence or absence of treatment candidate substances of liver diseases.

For example, one or more kinds selected from the group consisting of the direct conversion-induced hepatic stem cell, hepatocyte and cholangiocyte from a somatic cell, and differentiation-induced hepatocyte and cholangiocyte from the directly converted hepatic stem cell of the present invention may be used for evaluating toxicity against candidate substances or medicinal effects as an important cell in recovery or treatment of liver diseases.

The evaluation of toxicity may be evaluated according to a method commonly judging toxicity in the art such that differentiation of the hepatic stem cell in which direct conversion is induced in a somatic cell of the present invention into a hepatocyte or a cholangiocyte is inhibited, or IC50 (the lowest concentration of treatment candidate substances inducing 50% kill of cells) to one or more kinds selected from the group consisting of the direct conversion-induced hepatic stem cell, hepatocyte and cholangiocyte from a somatic cell, and differentiation-induced hepatocyte and cholangiocyte from the directly converted hepatic stem cell of the present invention, in presence or absence of treatment candidate substances of the present invention, etc. In addition, the evaluation of medicinal effects may be evaluated according to a method which is capable of confirming that it has an effect for treating liver diseases in the art, such that differentiation of the hepatic stem cell in which direct conversion is induced in a somatic cell of the present invention into a hepatocyte or a cholangiocyte is promoted, or that one or more kinds selected from the group consisting of the direct conversion-induced hepatic stem cell, hepatocyte and cholangiocyte from a somatic cell, and differentiation-induced hepatocyte and cholangiocyte from the directly converted hepatic stem cell promotes treatment of liver diseases, etc.

In one specific example, a method for screening a drug for preventing or treating a liver disease comprising:

a step of contacting a first cell sample with a candidate substance;

a step of measuring a level of apoptosis, drug metabolism, or fat absorption in the first cell sample;

a step of comparing the level of apoptosis, drug metabolism, or fat absorption in the first cell sample which is contacted with the candidate substance with the level of apoptosis, drug metabolism, or fat absorption in a second cell sample which is not contacted with the candidate substance; and a step of determining the candidate substance as a candidate drug for preventing or treating a liver disease, when the level of apoptosis, drug metabolism, or fat absorption in the first cell sample which is contacted with the candidate substance is lower than the level of apoptosis, drug metabolism, or fat absorption in the second cell sample which is not contacted with the candidate substance is provided.

The liver disease is as described above.

The first cell sample and the second cell sample are each independently one or more kinds selected from the group consisting of hepatic stem cell, hepatocyte and cholangiocyte produced (direct conversion-induced) by the method of direct conversion of the present invention.

The candidate substances may one or more kinds selected from the group consisting of a small molecular drug, a peptide, a protein (for example, antibody, etc), a nucleic acid molecule, a natural substance, an extract of natural substance, etc, but not limited thereto.

The present invention provides a composition inducing direct conversion into a hepatic stem cell, which is capable of differentiation from a somatic cell into a hepatocyte and a cholangiocyte and self-reproducing, through expression of direct conversion inducing factors without going through a pluripotency stage of a pluripotent stem cell, and provides a method for inducing direct conversion from a somatic cell into a hepatic stem cell, a hepatocyte and a cholangiocyte, using the composition, and prevention and treatment of liver diseases is possible using thereof.

EXAMPLES

Hereafter, the present invention will be described in detail by examples.

The following examples are intended merely to illustrate the invention and are not construed to restrict the invention.

<Referential Example 1> Cloning and Constructing Lentivirus Plasmids

Plasmids containing NR4A2, HNF4α, OCT4 were obtained from John Gearhart (Addgene plasmid #43918), Atsushi Suzuki (Addgene plasmid #33002), Shinya Yamanaka (Addgene plasmid #27077). NR4A1, TBX3, NR5A1, NR5A2, NR0B2 were amplified by PCR (polymerase chain reaction) using Phusion® High-Fidelity DNA Polymerase (NEB, M05305) in HepG2, H9 cDNA. NR4A2, HNF4α, OCT4, NR4A1, TBX3, NR5A1, NR5A2, NR0B2 were inserted into a lentiviral transfer vector. Lentiviral transfer plasmids which were prepared by inserting the genes into the lentiviral transfer vector were confirmed by sequence analysis.

<Referential Example 2> Lentivirus Packaging

Packaging mixture was prepared following the 3:2:1 ratio of lentiviral transfer plasmid:packaging plasmid (psPAX2): envelope plasmid (VSV-G) using X-tremeGENE™ 9 DNA Transfection Reagent (Roche, 06365787001). Total volume summed up to 200 uL using DMEM (DMEM, Invitrogen, 10313-021). Before transferred into 293T cells (293 cells with large T antigen, ATCC) with 40-60% confluency, 30 minutes of incubation at room temperature was performed. Separate factors were prepared separately. Cell medium that incubated with virus packaging mixture for 48 hrs at 37° C. under 5% $CO_2$ was harvested through 0.45 um filter for removing cell debris and stored at −80° C.

<Referential Example 3> In Vitro Differentiation

For differentiation of hepatocytes, hepatic stem cells were seeded in a collagen coated dish and cultured in the modified medium by adding 20 ng/mL Oncostatin M (R & D system) to HEP medium (Hepatocyte Culture Medium, hepatocyte culture medium, Lonza HCM bulletkit (cc3198). The culture medium was changed once every 2 days.

For differentiation of cholangiocytes, hepatic stem cells were three-dimensionally cultured using collagen type 1 (BD 354236) according to the manufacturer's instructions. Briefly, hepatic stem cells ($0.5\times10^4$ cells) were mixed with collagen gel comprising 40% (w/v) Matrigel® (BD 354234) which was freshly prepared and placed in a 4-well dish. Cholangiocyte differentiation (CLD) medium (HEP medium in which 20 ng/mL EGF (Peprotech) was added) was added after gel hardening and cultured for 3 days.

<Referential Example 4> Immunofluorescence Staining

For immunocytochemistry, cells were fixed with 4% paraformaldehyde (Santacruz, SC-281692) in Dulbecco's Phosphate-Buffered Saline (DPBS, Corning, 21-031-CV) for 10 minutes at room temperature. Fixed cells were washed three times in PBS comprising 0.05% Tween®-20 (Sigma, P7949) then permeabilized using DPBS with 0.1% Triton® X-100 (Sigma, T9284) for 10 minutes in room temperature. After washing three times with DPBS/Tween®-20 (PBST), 4% FBS in DPBS were used for blocking non-specific binding in room temperature for 60 minutes. Cells were then incubated with primary antibodies (anti-Albumin (1:200; R&D, MAB1455), anti-E-cadherin (1:200; Abcam, AB76055), anti-a-fetoprotein (1:200; R&D, MAB1368) and anti-Cytokeratin19 (1:400; Abbomax, 602-670)) in room temperature for 60 minutes, which was followed by three times washing steps and later on secondary fluorescent antibodies incubation in dark with Alexa Fluorophore-conjugated secondary antibodies 488 or Alexa Fluro® 594 (1:1000; Invitrogen). If double staining was needed, additional blocking for 30 minutes in room temperature was necessary before treating other primary antibodies according to the above procedures. Cells were placed in PBS for visualized using fluorescent microscope.

<Referential Example 5> Statistical Analysis

Every statistical analysis was conducted using unpaired two-tailed Student's t-test, and significance is $*p<0.05$ or $**p<0.01$.

Example 1. Induction of Fibroblasts into Induced Hepatic Stem Cells (iHSCs) by Direct Conversion Factors In order to determine possibility for induction of hepatic stem cells, dermal fibroblasts derived from a mouse tail were seeded in a culture dish and mouse OCT4 (NM_013633.3, SEQ ID NO: 89) and HNF4α (NM_008261.3, SEQ ID NO: 91) were introduced into fibroblasts through the lentivirus expression system of FIG. 1 for 24 hrs. Fibroblasts were obtained by primary culturing after attaching dermal tissue to a gelatin coated culture dish and used. The fibroblasts were cultured in MEF medium (Dullbecco's modified Eagle's medium supplemented with 10% (v/v) FBS, non-essential amino acids, L-glutamine, penicillin/streptomycin, mercaptoethanol) in a 37° C., 5% $CO_2$ incubator.

Figure 21:
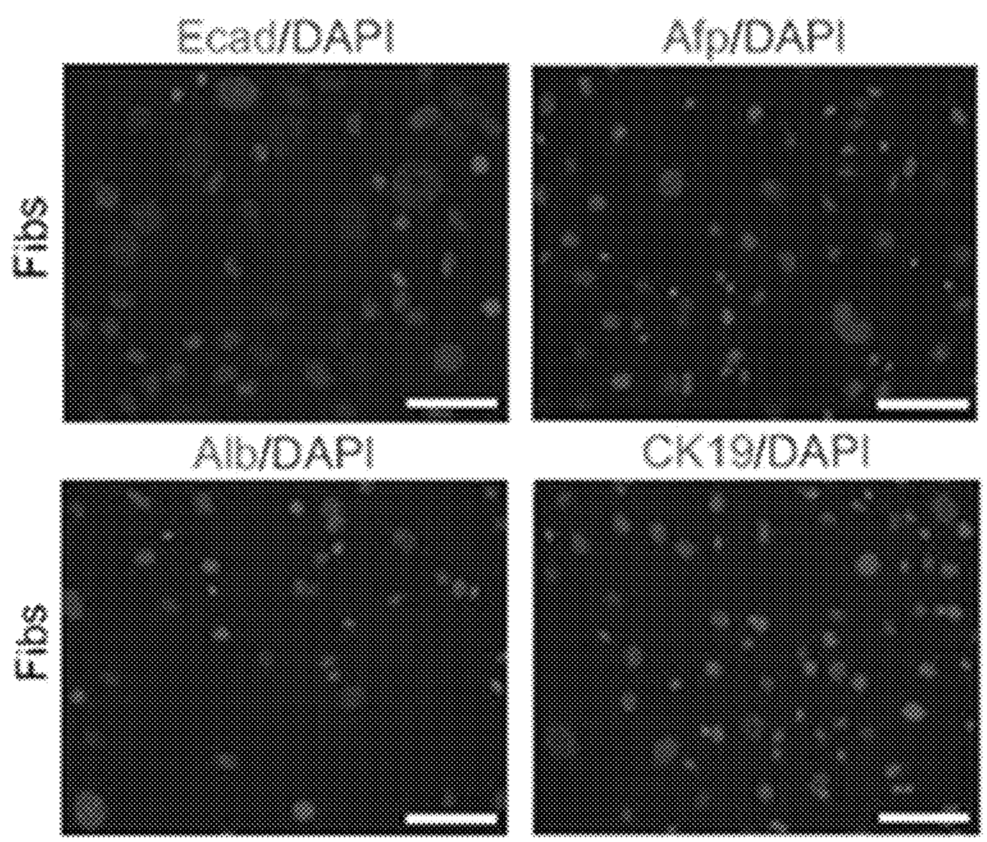
FIG. 21 shows confirmed expression of hepatic stem cell-specific marker in a somatic cell (fibroblast) by fluorescence staining. The scale bar shows 100 um.

In order to confirm that hepatic system cells were not mixed in fibroblasts, as shown in FIG. 21, it was confirmed that hepatic liver marker (Alb and Afp), hepatic stem cell marker (E-cad) and cholangiocyte marker (CK19) exhibited negativity, by conducting immunofluorescence staining in the same method as Referential Example 4.

In the present invention, E-cad was used as one of hepatic stem cell markers, and E-cad is known as an epithelial marker and hepatic stem cell marker.

Figure 2:
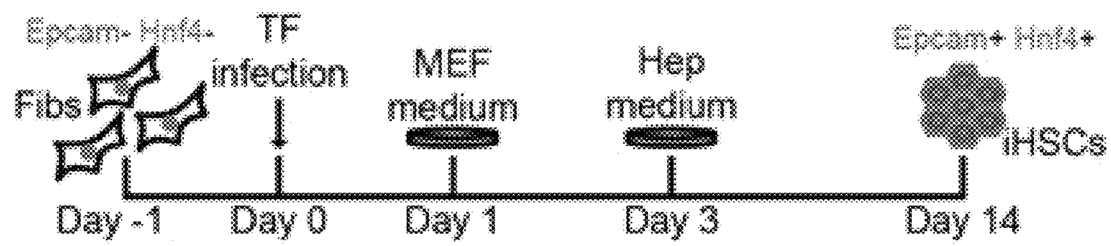
FIG. 2 is a diagram showing preparation flow of hepatic stem cells.

The process of producing hepatic stem cells was as follows. Fibroblasts ($1.0\times10^4$ cells) were seeded in a gelatin coated 12 well dish one day prior to lentiviral infection. Lentiviruses with transcriptional factors were infected the next day after seeding cells. After 3 days of lentiviral infection, MEF medium comprising 10% (v/v) FBS (fetal bovine serum, Invitrogen), 2 mM L-Glutamine (Invitrogen, 25030-081), MEM Non-essential amino acid (NEAA, Gibco, 11140-050), 55 uM β-Mercaptoethanol (β-ME, Invitrogen, 21985-023) and Penicillin/Streptomycin (Invitrogen, 15140-122) (Dulbecco's modified Eagle's medium (DMEM, Invitrogen, 10313-021) was replaced with HEP medium (Hepatocyte Culture Medium, hepatocyte culture medium, Lonza HCM bulletkit (cc3198)). Such production process was illustrated in FIG. 2.

Figure 3:
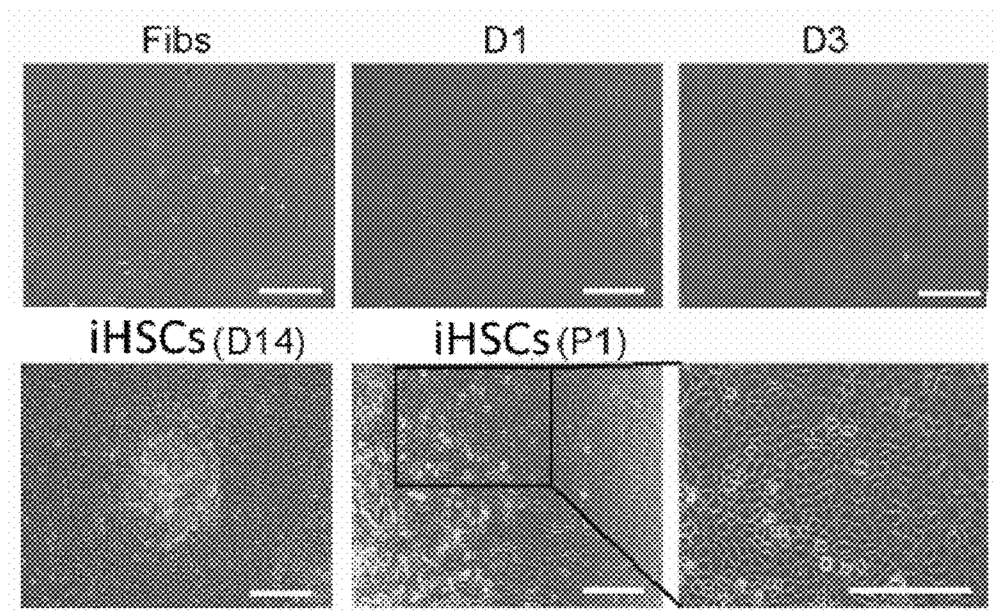
FIG. 3 shows morphological changes of somatic cells after introducing a hepatic stem cell inducing factor observed by a microscope. The scale bar shows 250 um.

As can be seen in FIG. 3, which is a result of observing morphological changes of cells, 14 days after infecting with lentiviruses, even after a cubic form of cells having a clear nucleus passed through a collagen coated plate, colonies which can maintain similar morphology as original morphology were shown. Such cells were called hepatic stem cells.

Hepatic stem cells are characterized by expressing hepatocyte-specific markers and cholangiocyte-specific markers. In order to confirm whether cells infected with lentiviruses express hepatocyte-specific markers, reverse transcription PCR was conducted as follows.

Total RNA was obtained from cell lysates using RNeasy® Mini Kit (Qiagen, 74104) and obtained from liver tissue using TRIzol® Reagent (Invitrogen, 15596-018). 500 ng of synthesized total RNS, Omniscript® Reverse Transcriptase (Qiagen, 205111), and oligo-dT primer were added to 20 uL reaction mixture and reacted at 37° C. for 1 hr to synthesize cDNA. Reverse transcription PCR (Polymerase chain reaction) was conducted under the condition of reacting Taq polymerase (Invitrogen, 10342-020) and primers at 58° C. for 38 cycles. Reaction products were subjected to 2% (w/w) agarose gel electrophoresis at 100 V for 2 hrs. Primer sequences used in Reverse transcription PCR were shown below (sequences below were represented in the 5' to 3' direction).

```
Gata4_F:
                              (SEQ ID NO: 1)
GACACCCCAATCTCGATATGTT

Gata4_R:
                              (SEQ ID NO: 2)
GGACCTGCTGGCGTCTTAG

Foxa2_F:
                              (SEQ ID NO: 3)
CACCTGAGTCCGAGTCTGAG

Foxa2_R:
                              (SEQ ID NO: 4)
AAGGAGAGAGAGTGGCGGAT

Gata6_F:
                              (SEQ ID NO: 5)
GTGAACTGCGGCTCCATCC

Gata6_R:
                              (SEQ ID NO: 6)
TGATGCCCCTACCCCTGAG

Hnf4a_F:
                              (SEQ ID NO: 7)
AGGCAATGACTACATCGTCCC

Hnf4a_R:
                              (SEQ ID NO: 8)
CAGACCCTCCGAGAAGCATC

EpCam_F:
                              (SEQ ID NO: 9)
GGTGAATGCCAGTGTACTT

EpCam_R:
                             (SEQ ID NO: 10)
CAATGATGATCCAGTAGGTCC
```

-continued

```
Ecad_F:
                             (SEQ ID NO: 11)
GCAGGTCTCCTCATGGCTTTG

Ecad_R:
                             (SEQ ID NO: 12)
TTGGATTCAGAGGCAGGGTCG

Dlk1_F:
                             (SEQ ID NO: 13)
GCACCTATGGGGCTGAATG

Dlk1_R:
                             (SEQ ID NO: 14)
GGCAGGGAGAACCATTGAT

Oc2_F:
                             (SEQ ID NO: 15)
GCTACACCACGCCATGAGTAT

Oc2_R:
                             (SEQ ID NO: 16)
TGGGGCTGAGCATTTTGTC

Alb_F:
                             (SEQ ID NO: 17)
TGAAGTTGCCAGAAGACATCC

Alb_R:
                             (SEQ ID NO: 18)
CAAGTTCCGCCCTGTCATCTG

Ttr_F:
                             (SEQ ID NO: 19)
GCTTCCCTTCGACTCTTCCTC

Ttr_R:
                             (SEQ ID NO: 20)
GCCAAGTGTCTTCCAGTACGA

CK8_F:
                             (SEQ ID NO: 21)
AGAAGGATGTGGACGAAGCA

CK8_R:
                             (SEQ ID NO: 22)
ATCTCTGTCTTTGTGCGGCG

CK18_F:
                             (SEQ ID NO: 23)
ATGAAGAGGAAGTCCAAGGTC

CK18_R:
                             (SEQ ID NO: 24)
GTTCTCCAAGTTGATGTTCTG

Afp_F:
                             (SEQ ID NO: 25)
GCAGGATGGGGAAAAAGTCA

Afp_R:
                             (SEQ ID NO: 26)
CCTAAGGTCTGGTAGAGAGCG

Aat_F:
                             (SEQ ID NO: 27)
GACCAAGACACAGTTTTCGC

Aat_R:
                             (SEQ ID NO: 28)
ATCTGGGCTAACCTTCTGCG

Tat_F:
                             (SEQ ID NO: 29)
ATCGGCTACCTATCCAGTCG

Tat_R:
                             (SEQ ID NO: 30)
GCCACTGCCAAAATCTTCTGA
```

-continued

G6P_F:
(SEQ ID NO: 31)
TCAACCTCGTCTTCAAGTGGATT

G6P_R:
(SEQ ID NO: 32)
CACAGCAATGCCTGACAAGA

Cyp7a1_F:
(SEQ ID NO: 33)
GGAGCCCTGAAGCAATGAAA

Cyp7a1_R:
(SEQ ID NO: 34)
AAAAGTCAAAGGGTCTGGGT

CK7_F:
(SEQ ID NO: 35)
CCTTCACGAGACAGAGTTAGCA

CK7_R:
(SEQ ID NO: 36)
ACTTGGCACGCTGGTTCTT

CK19_F:
(SEQ ID NO: 37)
AGTTTGAGACAGAACACGCCT

CK19_R:
(SEQ ID NO: 38)
CTCCTCAATCCGAGCAAG

Ggt1_F:
(SEQ ID NO: 39)
ATCTACAACAGCACCACAGGA

Ggt1_R:
(SEQ ID NO: 40)
TCAACCGTCATAATGCCACCA

Gapdh_F:
(SEQ ID NO: 41)
ACGACCCCTTCATTGACCTCAACT

Gapdh_R:
(SEQ ID NO: 42)
ATATTTCTCGTGGTTCACACCCAT

Figure 4:
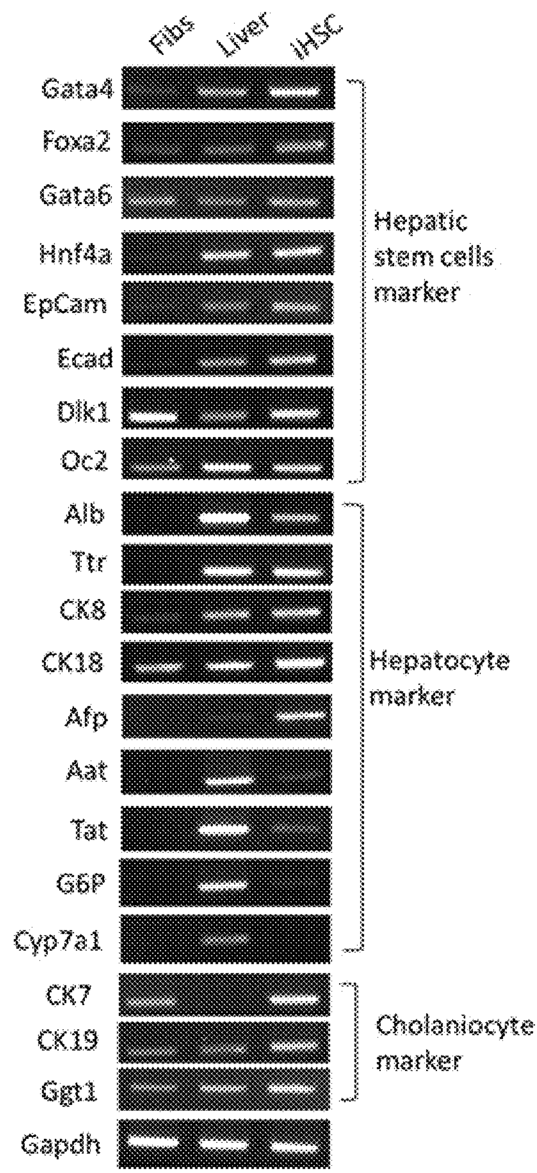
FIG. 4 shows confirmed expression of hepatic stem cell genes (GATA4, FOXA2, GATA6, HNF4α, EPCAM, ECAD, DLK1, OC2), hepatocyte genes (ALB, TTR, CK8, CK18, AFP, AAT, TAT, G6P, CYP7a1), cholangiocyte genes (CK7, CK19, GGT1) of prepared hepatic stem cells.

As a result of conducting reverse transcription PCR by the above method, as shown in FIG. 4, it was confirmed that cells infected with lentiviruses expressed hepatic stem cell markers (GATA4, FOXA2, GATA6, HNF4α, EPCAM, E-CAD, DLK1, OC2), hepatocyte markers (ALB, TTR, CK8, CK18, AFP, AAT, TAT, G6P) and cholangiocyte markers (CK7, CK19, GGT1).

Figure 5:
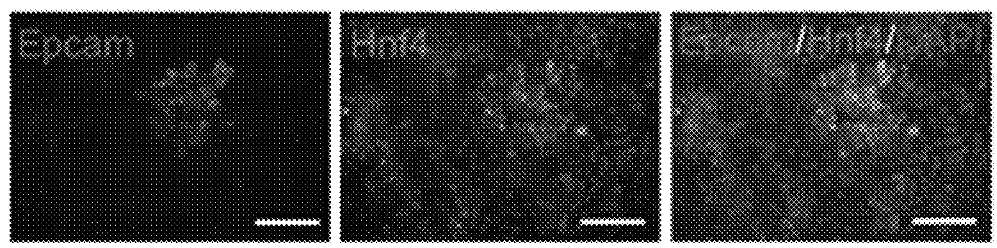
FIG. 5 shows expression of prepared hepatic stem cell-specific marker (Epcam, Hnf4α) proteins observed by immunofluorescence staining. The scale bar shows 100 um.

In addition, in order to confirm protein expression of hepatocyte-specific markers, it was confirmed that cells infected with lentiviruses expressed hepatic stem cell markers (Epcam, Hnf4α) by conducting immunofluorescence image analysis in the same method as Referential Example 4, as shown in FIG. 5.

In other words, to sum up the above results confirming expression of hepatocyte-specific markers in the mRNA level and protein level, it was demonstrated that hepatic stem cells were produced from fibroblasts by infecting lentiviruses and introducing OCT4 and HNF4α into fibroblasts.

Example 2. In Vitro Differentiation of Hepatocytes and Cholangiocytes from Hepatic Stem Cells Whether hepatic stem cells prepared by the same method as Example 1 could differentiate into hepatocytes and cholangiocytes was confirmed. In order to confirm dual differentiation ability of hepatic stem cells, hepatic stem cells were plated in a dish in which HEP medium coated with collagne comprising Oncostatin M was placed, to differentiate into hepatocytes, in the same method as Referential Example 3. After hepatic stem cells differentiated into mature hepatocytes (induced hepatocytes, iHep), additional experiments were performed to confirm function of differentiated hepatocytes.

Cytochrome P450 (CYP) family is an essential enzyme in the in vivo change and reaction of drugs. In order to compare changes of genetic expression related to Cytochrome P450 (CYP) in hepatocytes, qRT-PCR (real time quantitative PCR) was conducted.

Total RNA was extracted and cDNA was synthesized in the same method as Example 1. qRT-PCR was performed using synthesized cDNA. mRNA expression of specific genes was confirmed using SYBR Green I Master (Roche, 04887352001) and primers in LightCycler® 480 equipment. The average value was calculated for three analyzes and normalized using Gapdh (5'-TGCCCCCATGTTTGTGAT-3' (SEQ ID NO: 94) and 5'-TGTGGTCATGAGCCCTTC-3' (SEQ ID NO: 95)). The expression level of mRNA was compared using comparative Ct method. Primer sequences used in qRT-PCR were shown below (sequences below were represented in the 5' to 3' direction).

Cyp1a2_F:
(SEQ ID NO: 43)
ATAACTTCGTGCTGTTTCTGC

Cyp1a2_R:
(SEQ ID NO: 44)
ACCGCCATTGTCTTTGTAGT

Cyp1b1_F:
(SEQ ID NO: 45)
ATTCTCAGTGGGCAAACGG

Cyp1b1_R:
(SEQ ID NO: 46)
GGATTCTAAACGACTTGGGCT

Cyp2b10_F:
(SEQ ID NO: 47)
CTGTCGTTGAGCCAACCTTC

Cyp2b10_R:
(SEQ ID NO: 48)
TCCGCAGTTCCTCCACTAAA

Cyp2c37_F:
(SEQ ID NO: 49)
TGTGGAGGAACTTAGGAAAACC

Cyp2c37_R:
(SEQ ID NO: 50)
AGGGCTGCTCAGAATCTTTGT

Cyp2d22_F:
(SEQ ID NO: 51)
GCCTTCATGCCATTCTCAGC

Cyp2d22_R:
(SEQ ID NO: 52)
CAGAGCCCTAAAGACGCC

Cyp2e1_F:
(SEQ ID NO: 53)
GGAATGGGGAAACAGGGTAAT

Cyp2e1_R:
(SEQ ID NO: 54)
GCACAGCCAATCAGAAAGGT

Cyp3a11_F:
(SEQ ID NO: 55)
TGGGACTCGTAAACATGAACTT

-continued

```
Cyp3a11_R:
                                    (SEQ ID NO: 56)
TTGACCATCAAACAACCCCC

Cyp3a13_F:
                                    (SEQ ID NO: 57)
GGGGACGATTCTTGCTTACC

Cyp3a13_R:
                                    (SEQ ID NO: 58)
AAATACCCACTGGACCAAAGC
```

Figure 6:
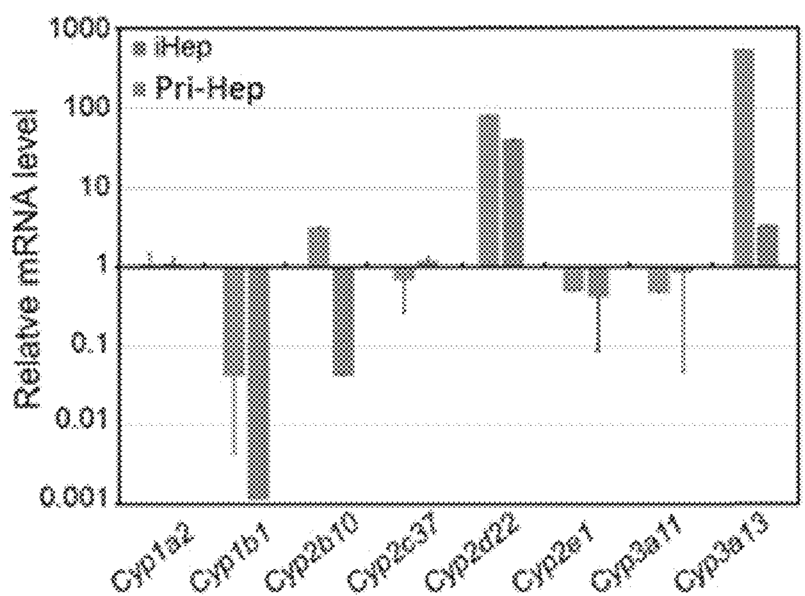
FIG. 6 shows expression of CYP450 related genes confirmed in hepatocytes (iHep) and primary culture hepatocyte (primary hepatocyte, Pri-Hep).

As the result of qRT-PCR, as shown in FIG. 6, hepatocytes (iHep) showed an increased mRNA expression of CYP related genes (orange), and such changes of expression were significantly similar to mRNA expression increase shown in primary culture hepatocytes (Fri-Hep) isolated from 10-week adult mouse liver through 2 steps of decomposition process using collagenases (blue).

The CYP family members were known to be regulated by aryl hydrocarbon receptor (AhR), constitutive androstane receptor (CAR), pregnane X receptor (PXR), and nuclear receptor which were abundantly found in liver tissue. In order to confirm whether hepatocytes induce CYP when a stimulus was given to such receptors, chemical compounds such as 3-methylcholanthrene (3Mc) which acts on aryl hydrocarbon receptors (Cyp1 family members) and glucocorticoid (Dex, dexamethasone) which acts on glucocorticoid receptors (glucocorticoid receptor regulating CAR and PXR is upstream of Cyp2/3 family members) were treated to receptors.

Specifically, cells were cultured with 60% confluency in HEP medium in which dexamethasone was not added. DMSO, 25 mM 3-methylcholanthrene (3-Mc), 1 uM dexamethasone (Dex), or 50 mM ethanol (Eth) was added and fresh medium was changed every day and they were cultured for 72 hrs. Cells treated with Dimethyl sulfoxide (DMSO, Sigma, D2650) were used as a control group.

Figure 7:
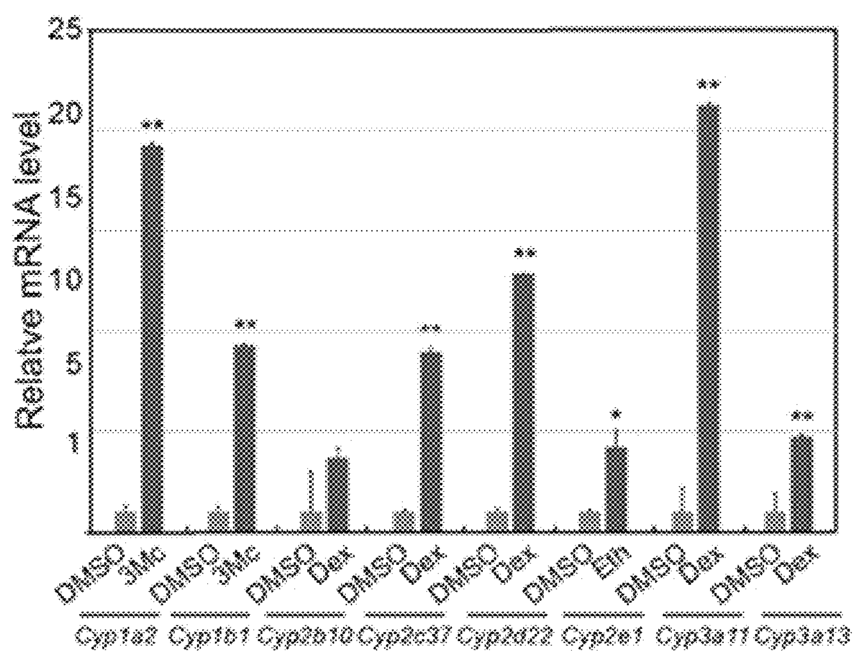
FIG. 7 shows confirmed expression change of CYP450 related genes of hepatocytes by drug treatment. The expression of CYP family genes is induced by using 3-methylcholanthrene (3Mc), glucocorticoid (Dex, dexamethasone), or ethanol.

As a result, as shown in FIG. 7, it was confirmed that mRNA of CYP related genes was increased when chemical compounds were treated to the hepatocytes by conducting qRT-PCR. In addition, it was confirmed that there was no effect on viability of treated cells for 72 hrs when the chemical compounds were treated by observing forms of cells. It was demonstrated that prepared hepatocytes could function drug metabolism normally by such results.

In addition, in order to confirm glycogen storage function of differentiated hepatocytes, Periodic acid-Schiff (PAS) staining was performed in the following method.

Cells were stained with periodic acid-Schiff (PAS, Muto Pure Chemical, Japan, 15792) according to the manufacturer's instructions. To fix cells, 10% (v/v) formalin-methanol was cultured for 15 min, followed by treating 1% (v/v) Periodic acid for 10 min to form free aldehyde groups, to cut between carbon and carbon of glycogen or glycoprotein. Then, to form quinoid magenta color products, aldehyde groups were conjugated with Schiff's reagent at 37° C. for 30 min and stored in PBS for analysis with a microscope. All steps except a step of treating Schiff s reagent were conducted at a room temperature. Cells were washed three times for 5 min using water between each step.

Figure 8:
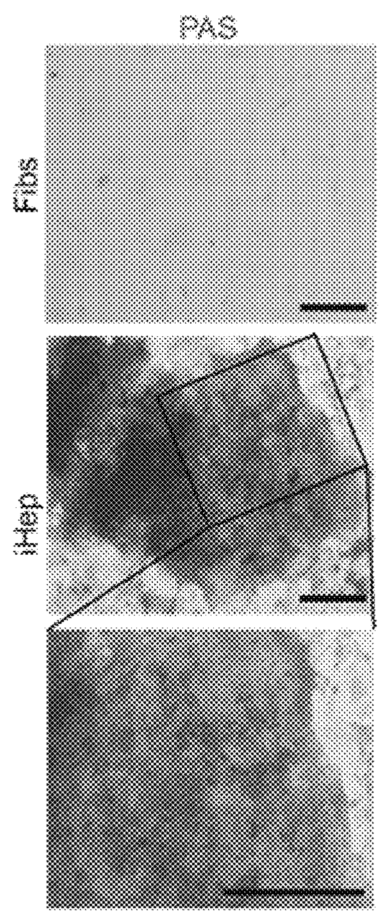
FIG. 8 shows glycogen storage function of hepatocytes (PAS stain) confirmed by a microscope. The scale bar shows 250 um.

As a result, as shown in the left part of FIG. 8, Periodic acid-Schiff (PAS) staining exhibiting glycogen storage in differentiated hepatocytes was confirmed.

In addition, in order to confirm detoxification function of hepatocytes, Indocyanine green (ICG) assay was conducted. ICG is a fluorescent dye and an indicator substance used for diagnosis of liver functions. Since ICG is metabolized in liver and released through liver and bile duct, it was used for judging detoxification function of liver. ICG assay was conducted in the following method.

To make Indocyanine green (ICG, Sigma, I2633-25MG) at 100 mg/mL stock concentration, after aliquoting it which was dissolved in 250 uL DMSO, it was stored at −20° C. in dark. 1 mg/ml ICG was further diluted into cell medium and incubated one hour at 37° C., followed by washing with PBS three times for the present assay (Uptake). Cells were cultured into ICG-free Hep medium for additional six hours at 37° C., and washed with PBS three times, for the present assay (Release). Observation with a microscope after culturing ICG exhibited ICG uptake cells (uptake), and observation with a microscope after culturing for 6 hrs in HEP medium without ICG exhibited those after ICG was released (release). The same spots on the plate were tracked throughout the whole process.

Figure 9:
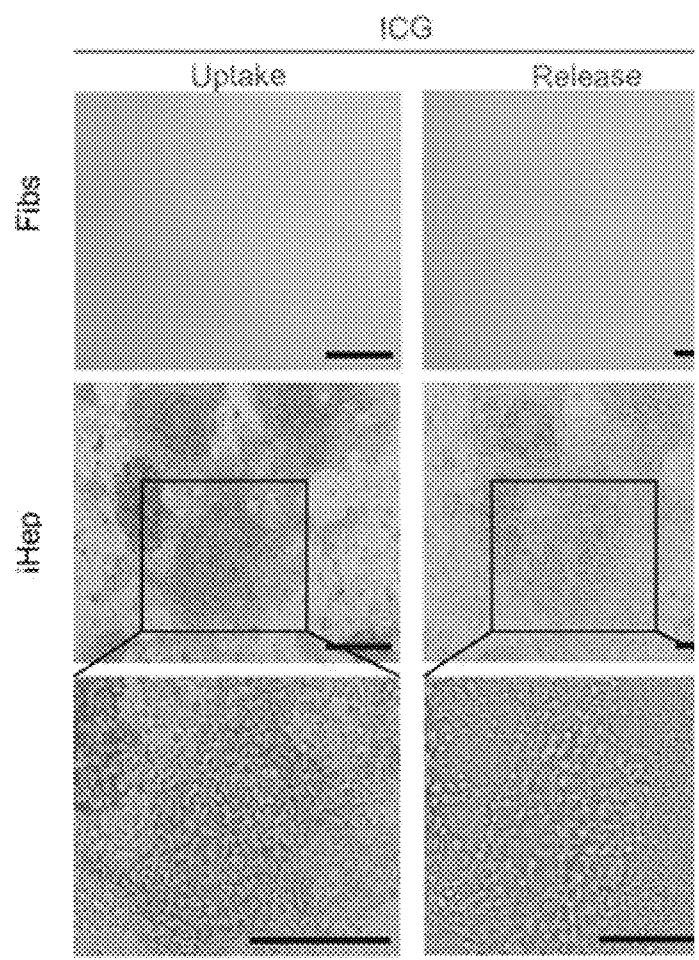
FIG. 9 shows detoxification function of hepatocytes (ICG release assay) confirmed by a microscope. Fibs of the top shows fibroblasts, and iHep of the middle shows hepatocytes which are directly converted from fibroblasts, and the bottom shows magnified hepatocytes which are directly converted. Uptake shows absorption of ICG, and Release shows when after ICG is released. The scale bar shows 250 um.

As the result of ICG assay, as shown in FIG. 9, it was confirmed that ICF uptake cells (green) rapidly disappeared in 6 hrs, and by this, it was demonstrated that differentiated hepatocytes have detoxification ability.

In addition, whether differentiated hepatocytes could absorb LDL was confirmed by conducting Dil-ac-LDL uptake assay. Dil-ac-LDL uptake assay was conducted by observing cells absorbing acetylated low density lipoprotein (ac-LDL) labeled with 1,1'-dioctadecyl-3,3,3',3'-tetramethyl-indocarbocyanine perchlorate (Biomedical Technologies, BT-902) with a fluorescence microscope equipped with standard rhodamine excitation/emission filter. Dil-ac-LDL uptake assay was done by treating 200 ng/mL ac-LDL to cells and culturing them under the condition of 5% $CO_2$ and 37° C. Nuclei were counterstained with DAPI.

Figure 10:
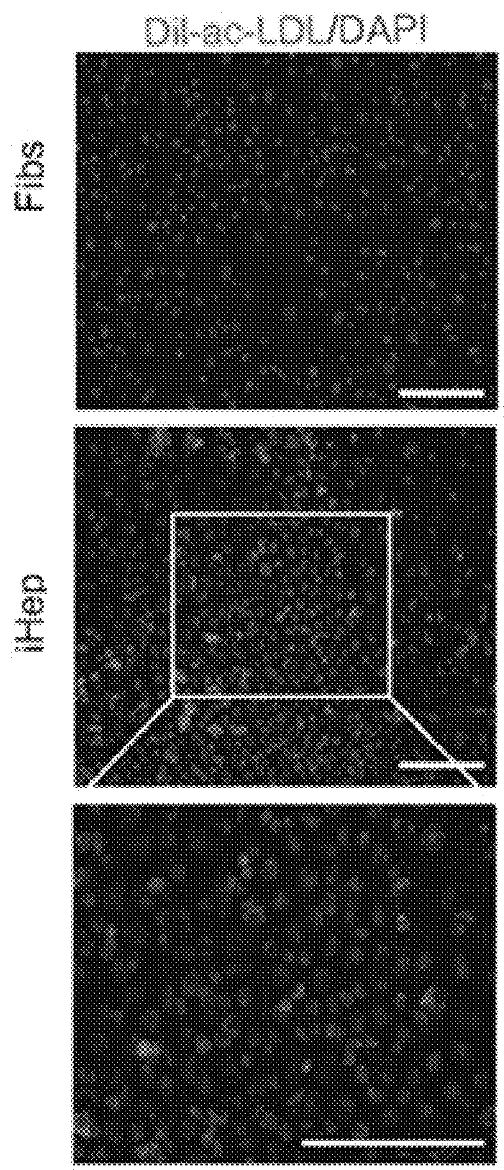
FIG. 10 shows confirmed cholesterol metabolism functions of hepatocytes (LDL uptake). The scale bar shows 100 um.

As the result of Dil-ac-LDL uptake assay, as shown in FIG. 10, differentiated hepatocytes absorbed LDL (low-density lipoprotein) through endocytosis mediated by LDL receptors.

In addition, in order to confirm the function of producing albumin proteins of hepatocytes, the amount of albumins which were present in the culturing medium was measured. Culture supernatant obtained by culturing mouse embryonic fibroblasts (MEF), hepatocytes and primary culture hepatocytes using albumin ELISA Kit (Bethyl Laboratories) according to the manufacturer's instructions was analyzed.

Figure 11:
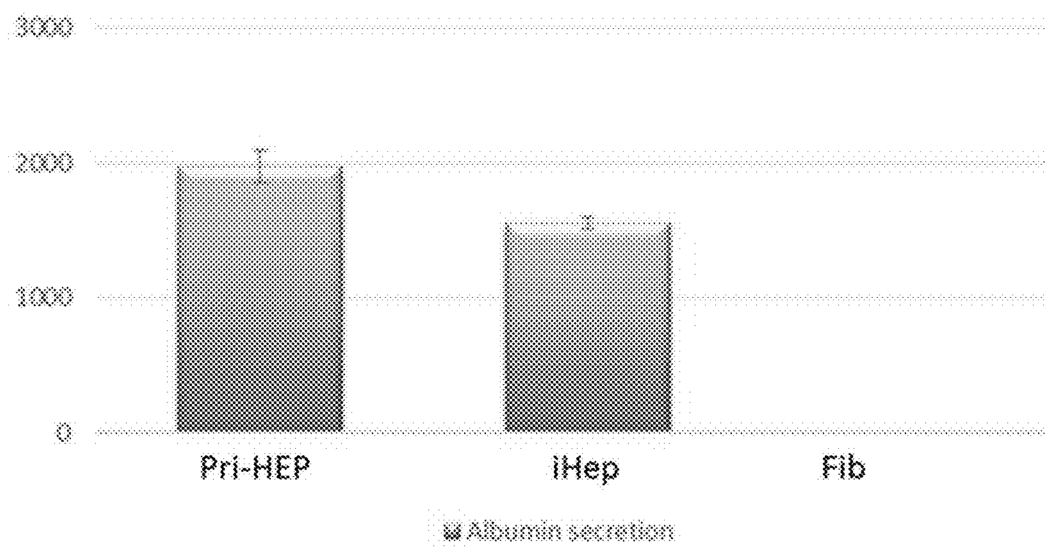
FIG. 11 shows confirmed albumin release of hepatocytes. Y axis shows albumin concentration (ng/mL/$1.0\times10^6$ cells).

As a result, as shown in FIG. 11, it was confirmed that albumins were released into the medium in which hepatocytes were cultured.

To sum up the above results, it was demonstrated that hepatocytes differentiated from hepatic stem cells were hepatocytes normally functioning.

To differentiate from hepatic stem cells into cholangiocytes, hepatic stem cells were cultured in cholangiocyte differentiation (CLD) medium comprising 40% Matrigel® in three-dimensional type I collagen gel culture system in the same method as Referential Example 3.

Figure 12:
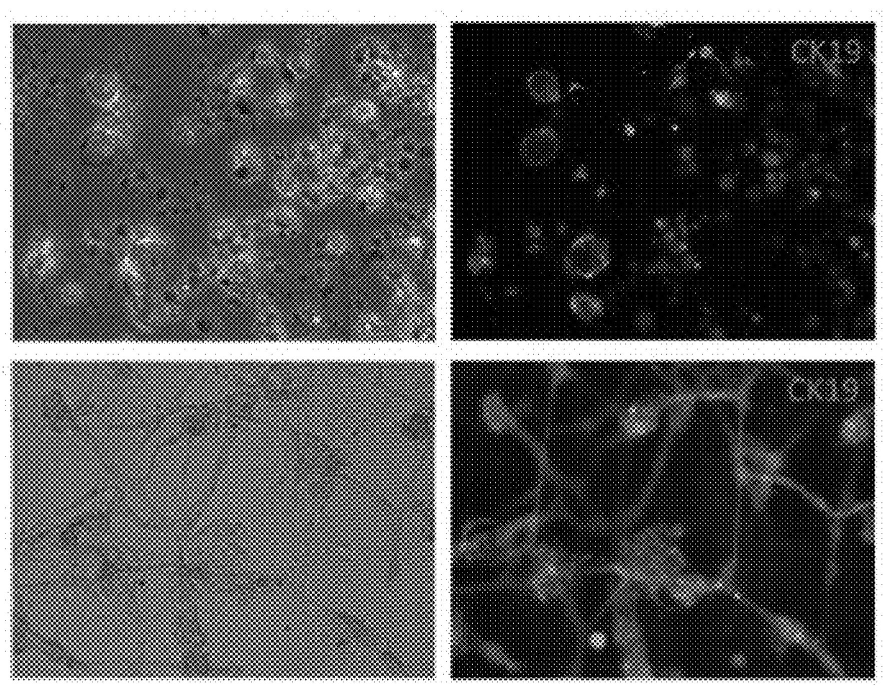
FIG. 12 shows observation of cystic type of cholangiocyte formation by three-dimensional culturing in Matrigel® (left upper part) and observation of tube type of cholangiocyte formation by three-dimensional culturing in Collagen (left lower part). The expression of Keratin 19 (CK19), which is a cholangiocyte-specific marker protein, is confirmed by conducting immunofluorescence staining (right).

As shown in FIG. 12, it was observed that differentiated hepatocytes differentiated into cholangiocytes which formed cystic and tube with a phase contrast microscope (left), and it was confirmed that CK19, which is a cholangiocyte-specific marker, was expressed by conducting immunofluorescence staining in the same method as Referential Example 4 (right).

Figure 13:
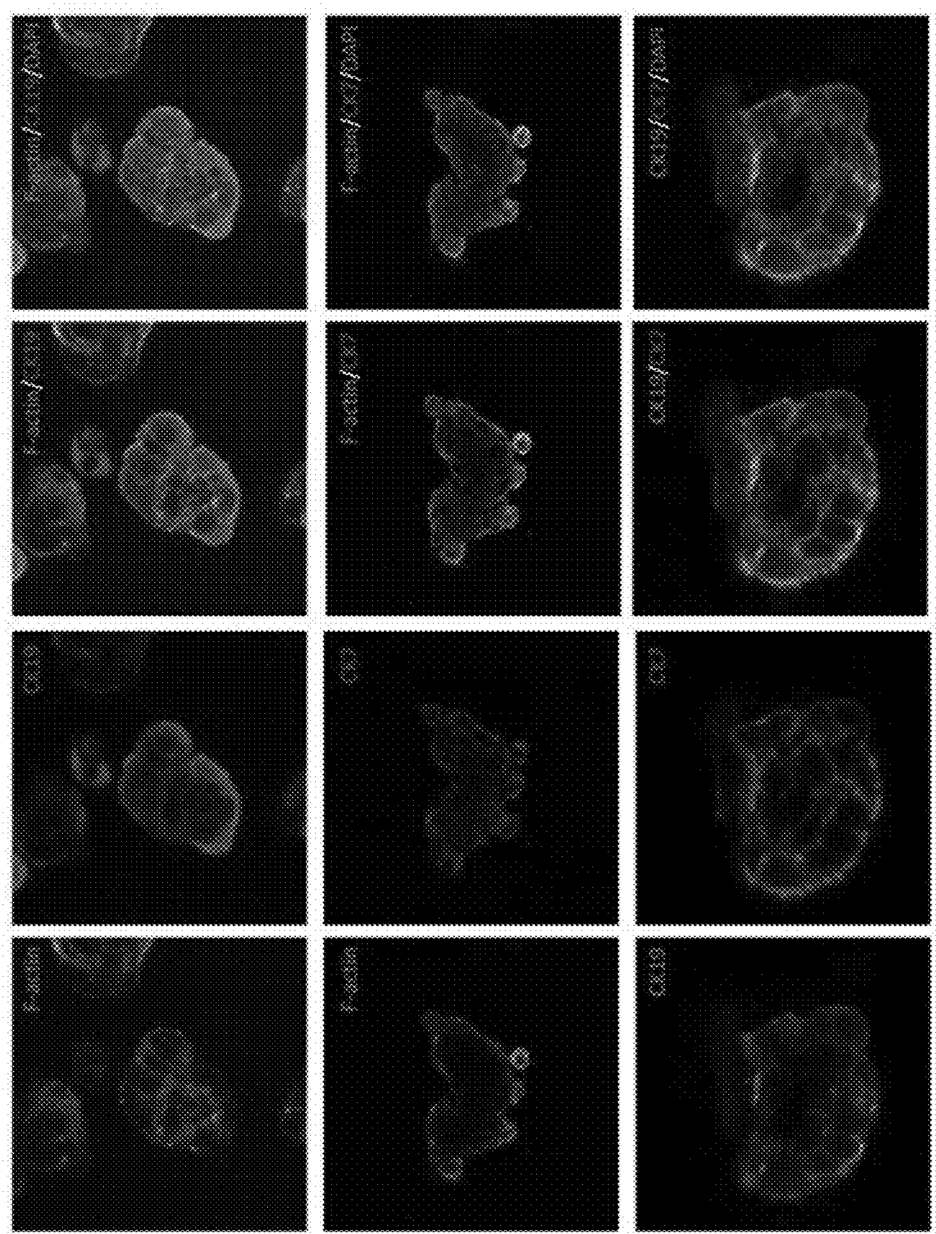
FIG. 13 is a result of immunofluorescence staining of F-actin (Phalloidin, green (GFP)) and marker proteins of cholangiocyte (CK19, CK7, red) in order to confirm apical-basal polarity in cystic structure of cholangiocyte, and analysis with a confocal microscope (Olympus, Laser scanning confocal microscopy, FY1000) in order to confirm intracellular locations (top, middle). The result of confirming the expression of cholangiocyte-specific marker proteins (CK19, CK7) by conducting immunofluorescence staining in the cholangiocyte with cystic structures is shown (bottom).

In order to evaluate functionality of cholangiocytes derived from hepatic stem cells, cystic formation to differentiated cholangiocytes was induced by culturing direct conversion-induced hepatic stem cells in Matrigel® in the same method as Referential Example 3. Then, in order to evaluate apical-basal polarity, immunofluorescence staining was conducted by performing F-actin staining in the same method as Referential Example 4. As a result, as shown in FIG. 13, localization of F-actin in the inner surface of bile duct cystic was confirmed. In addition, such cystic co-expressed CK19 and CK7, which are cholangiocyte markers (bottom).

In addition, in order to confirm whether differentiated cholangiocytes exhibited secretion function in vitro, Rhodamine 123 transport assay was conducted. Rhodamine 123 transport assay was conducted in the following method.

Cholangiocytes were cultured with 100 uM rhodamine 123(Sigma) at 37° C. for 5 min, and then washed with HEP medium three times. Then, cholangiocytes were additionally cultured in fresh HEP medium at 37° C. for 40 min. In order to confirm whether Rhodamine 123 transfer actually reflects activity of membrane channel MDR1 (Multidrug Resistance Protein 1), cells were cultured with 10 uM verapamil (Sigma-Aldrich) at 37° C. for 30 min, and the present assay was repeated. Images were obtained using a confocal microscope. Rhodamine 123 fluorescence of lumen was normalized to surrounding background.

Figure 14:
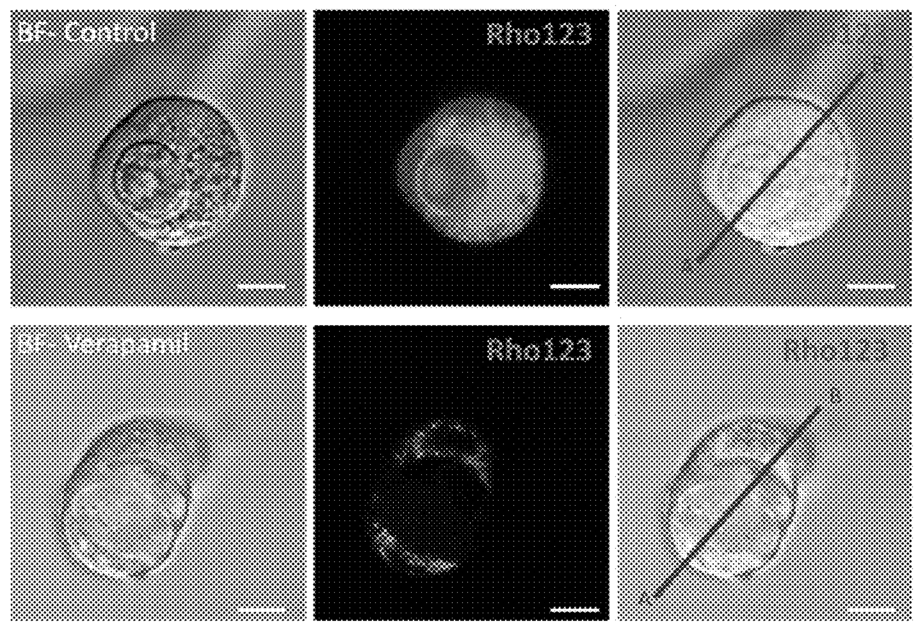
FIG. 14 shows drug secretion function of the cholangiocyte confirmed by using a confocal microscope (Olympus, Laser scanning confocal microscopy, FY1000), and shows that in case of treating MDR inhibitor (Verapamil) to the cystic type of cholangiocytes cultured three-dimensionally (lower part), fluorescent particles (Rhodamine 123) cannot pass through the lumen of the cholangiocyte structure by passing through MDR but remain only on the outer surface, compared with the group in which MDR inhibitor is not treated (upper part). The scale bar shows 2 um.
Figure 15:
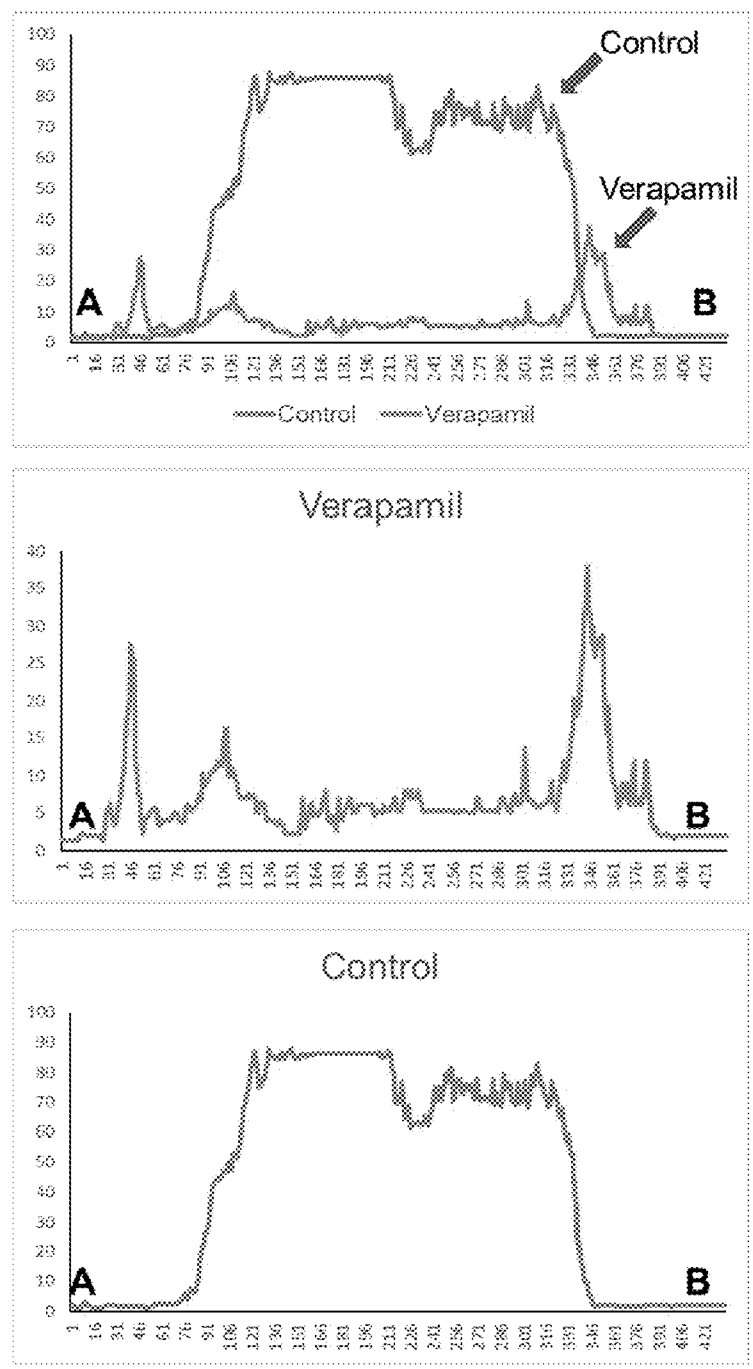
FIG. 15 shows a fluorescence intensity distribution diagram analyzing the red line as a boundary in the right image of FIG. 14. X axis is the interval of A and B of the right side of FIG. 14, and Y axis shows the intensity of fluorescence.

As shown in FIG. 14 and FIG. 15, cystic cholangiocytes transferred rhodamine 123, which is a fluorescence substrate to cholangiocyte surface glycoprotein MDR (multidrug resistance protein), into lumen. Transport potential of the cholangiocytes was inhibited by treatment of Verapamil, which is a MDR inhibitor.

Therefore, to sum up the above results, it was demonstrated that cholangiocytes differentiated from hepatic stem cells were cholangiocytes normally functioning.

Example 3. In Vitro Alcohol Liver Disease Modeling Using Hepatocytes

In order to confirm whether the hepatocytes could used as an in vitro alcohol liver disease model, 50 mM EtOH was treated to hepatocytes for 48 hrs and morphological changes of cells to which 50 mM EtOH was treated for 48 hrs were observed using a microscope.

Figure 16:
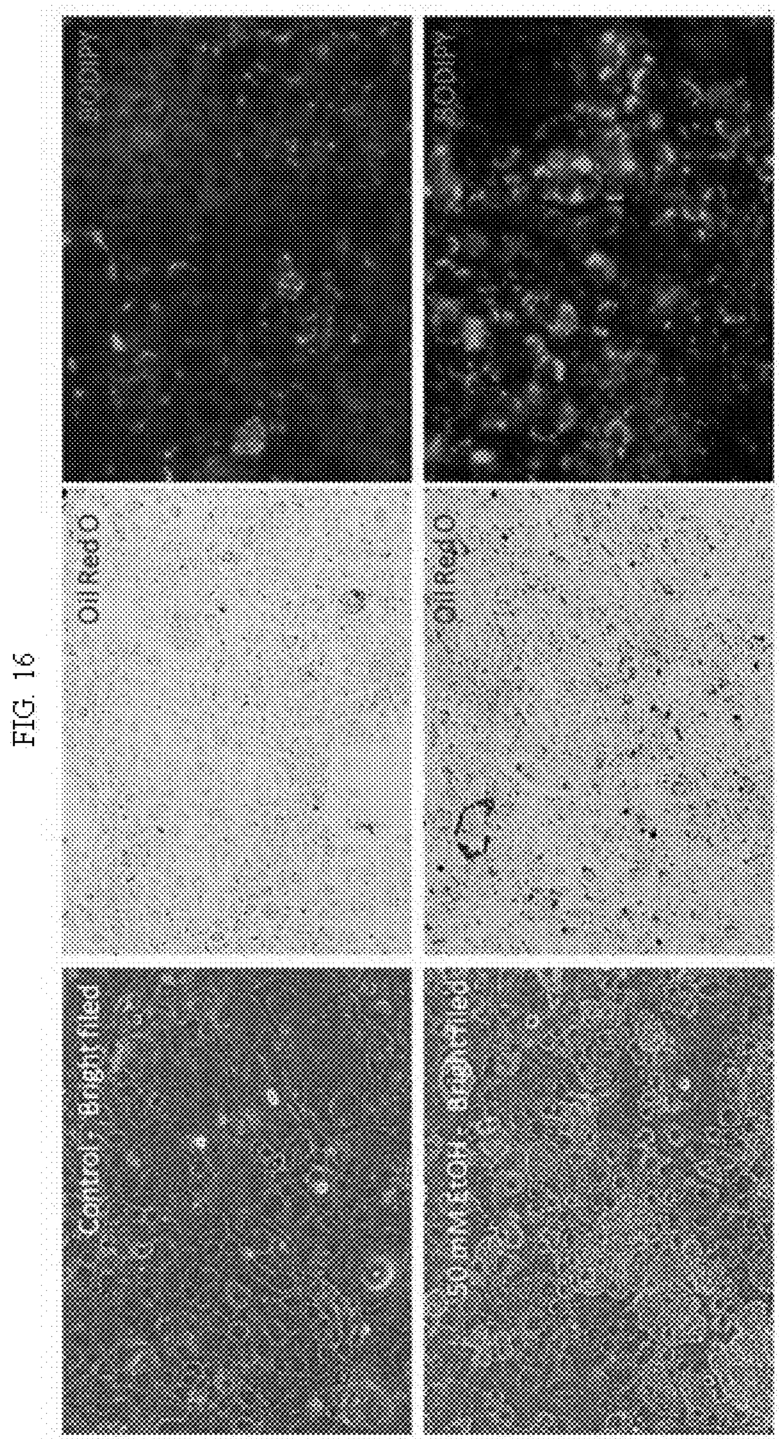
FIG. 16 shows observation of morphological changes using an optical microscope for the control group (upper part) and the group exposed to alcohol (lower part) by preparing hepatocytes of fatty liver model by exposure to alcohol in vitro for a certain time (right), and confirmation of accumulation of fats with Oil Red O stain (middle), and observation with a fluorescence microscope by staining with fat-specific fluorescence staining solution (Bodipy 430) in order to confirm lipid droplets accumulated in cells (right).

As shown in FIG. 16, accumulation of fats and formation of substrate small droplets in cytoplasm of hepatocytes treated with EtOH were observed by staining hepatocytes treated with EtOH with Oil Red 0 and Bodipy and observing with a fluorescence microscope in the same method as Referential Example 4.

By this, it was demonstrated that the hepatocytes could be used as a model showing liver damages due to alcohol in vitro.

Example 4. In Vivo Treatment Effect to Fibrosis Liver Disease Model

In order to examine in vivo treatment effect of hepatocytes, $CCl_4$ (carbon tetrachloride) induced hepatic fibrosis model was prepared and used to confirm reconstitution of liver capacity. Injected $CCl_4$ was converted to free radicals ($CCl_3$) by passing through metabolism processes by Cyp2e1, and hepatocytes could be damaged by accumulated free radicals. These damaged hepatocytes activated kupffer cell which is an immune cell existed in liver by occurring inflammatory responses, and factors which the immune cell secreted (cytokines) activated hepatic stellate cells existed in liver tissue, thereby causing hepatic fibrosis.

Figure 17:
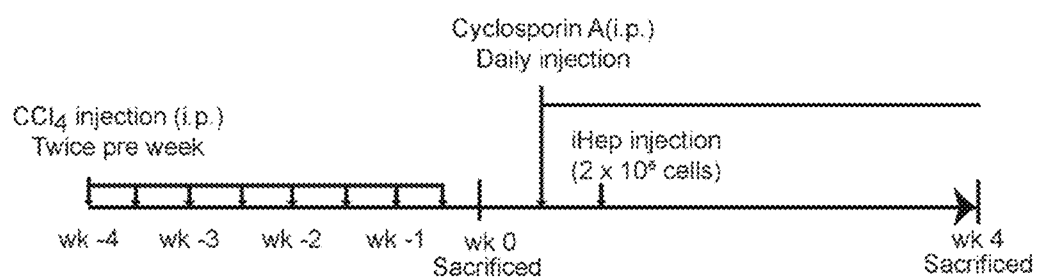
FIG. 17 shows a process of constructing a disease animal model of hepatic fibrosis model by injecting carbon tetrachloride (CCl4) into a C57BL/6J mouse (10 weeks old) for a certain period of time consistently, and injecting prepared hepatocytes.

Cell injection to $CCl_4$ induced mouse model was conducted in the following method. Primary fibrosis formation was induced by injecting $CCl_4$ twice a week for 4 weeks. To inhibit immune responses to injected cells, cyclosporine A which is an immunosuppressant was injected every day during the experiment period. Specifically, the mouse model induced by $CCl_4$ was purchased from Japan SLC, Inc. Hepatic fibrosis was induced by intraperitoneally injecting $CCl_4$ (2 mL/kg) which was melted in olive oil to 6-week male C57BL/6N mouse twice a week for 4 weeks. For injection to $CCl_4$ induced mouse model, hepatocytes labeled with CellTracker™ CM-DiI (Invitrogen, C7000) were prepared. By culturing 10 ug/mL CellTracker™ CM-DiI solution with hepatocytes that differentiation from the hepatic stem cells was induced at 37° C. for 5 min according to the manufacturer's instructions, hepatocytes were stained with the solution. $2\times10^6$ hepatocytes labeled with CellTracker™ CM-DiI were resuspended with 100 uL PBS and intrasplenically injected in hepatic fibrosis induced mouse liver by injecting $CCl_4$ under the approval of UNIST in vivo research center (IVRC) (Ulsan National Institute of Science and Technology). Frozen samples embedded in OCT compounds (CellPath, KMA-0100-00A) and tissue samples built in Paraffin (Leica, 39601006) were collected in liver tissue 4 weeks after cell injection. Such a preparation process was diagrammed in FIG. 17.

Figure 18:
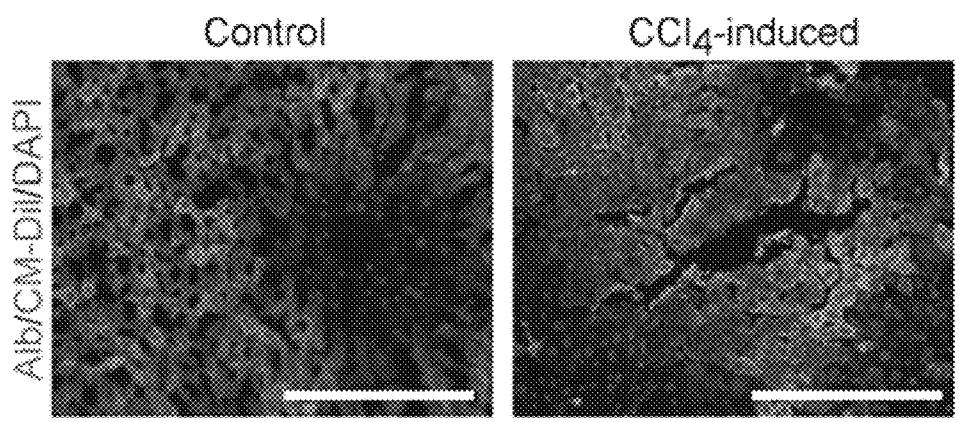
FIG. 18 shows confirmation of cells injected into a mouse (CM-Dil) which are lodged in liver tissue with a fluorescence microscope. The scale bar shows 100 um.

As a result of conducting immunofluorescence staining to liver in which hepatocytes labeled with CM-DiI were transplanted in the same method as Referential Example 4, as shown in FIG. 18, it was confirmed that transplanted hepatocytes expressed albumin in vivo. Low transplantation efficiency seems to be due to limited space accessible to transplanted cells in damaged liver.

Treatment effect of hepatocytes in $CCl_4$ induced mouse model was confirmed by conducting the following histological analysis. Liver tissue in which Paraffin was built was cut in 4 um thickness. Fragments were rehydrated with descending alcohol after separating Paraffin in xylene.

For antigen retrieval for immunohistochemistry (IHC), boiled 10 mM sodium citrate was treated for 20 min. Then, slides were cooled in distilled water before penetrating to 0.1% (v/v) Triton® X-100 (PBS-T) of PBS. To inhibit endogenous peroxidase, 3% (v/v) H2O2 (in deionized water) was treated for 30 min, and to minimize non-specific binding, CAS-Block (Invitrogen, 00-8120) was cultured for 8 min. α-SMA (1:200, Abcam, AB7817) was cultured at a room temperature for 1 hr. After washing with PBS-T, fragments were cultured with goat anti-mouse IgG-HRP (1:200, Santa Cruz, sc-2302). α-SMA was detected with AEC single solution (Invitrogen, 00-1111). Nuclei were stained with hematoxylin (Sigma, HHS32) and became blue with 0.2% (v/v) ammonium hydroxide, and then mounted with glycerol (Sigma, G5516). Using ImageJ (National Institutes of Health), the threshold value was set to 86, and the percentage of positive areas was calculated for 15 images randomly selected for each fragment for a total of 18 fragments. For Hematoxylin & eosin staining, at first nuclei were stained, and then fragments were soaked in Eosin Y solution (Sigma, HT110332) and washed several times and dehydrated. Slides were mounted with a mounting solution (Leica, 3801122).

Figure 19:
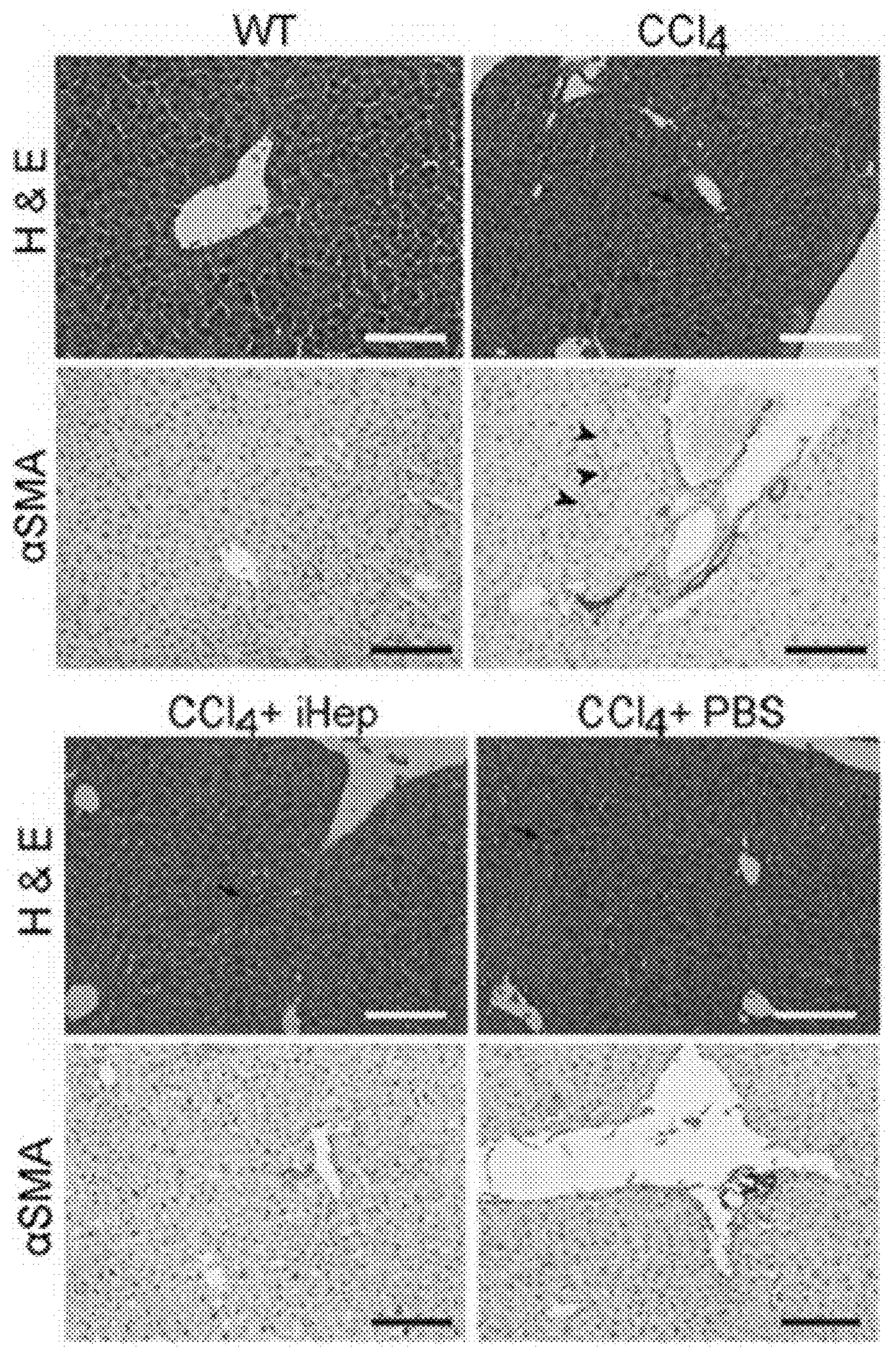
FIG. 19 shows treatment effects in a hepatic fibrosis model in which hepatocytes are injected by H & E stain (upper part), α-SMA staining (lower part), verified morphologically. The scale bar shows 100 um.
Figure 20:
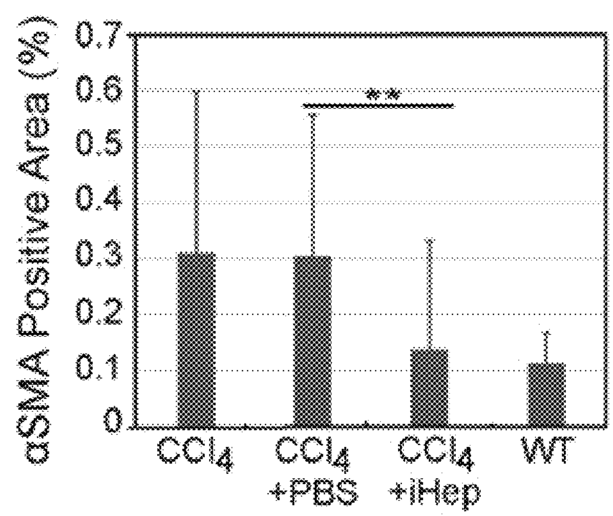
FIG. 20 shows a graphical representation of the result of FIG. 19 by quantitative analysis.

Preparation of hepatic fibrosis formation model and treatment effect of induced hepatocytes were confirmed through small inflammatory lymphocytes infiltration (arrow) and α-SMA (α-smooth muscle actin) staining (arrow head) showing hepatic stellate cells activated by inflammation and damages of hepatocytes. By conducting histological and immunohistological analyses in the above method, as shown in FIG. 19 and FIG. 20, it was confirmed that 1 month after injecting hepatocytes, hepatocyte injected CCl4 induced mouse showed less lymphocytes and less ratio of α-SMA positive regions compared with PBS injected mouse instead of hepatocytes By the above results, it was demonstrated that hepatocytes could be transplanted in liver tissue, and transplantation of hepatocytes had treatment effect for regeneration of hepatocytes damaged by $CCl_4$ and hepatic fibrosis diseases.

Example 5. Induction of Human Fibroblasts into Cholangiocytes by Direct Conversion Factors In order to confirm that direct conversion from somatic cells into cholangiocytes by direct conversion factors, human OCT4 (NM_002701.5, SEQ ID NO: 73) and HNF4α (NM_000457.4., SEQ ID NO: 75) genes were introduced into human fibroblasts (CRL-2097, ATCC) in the same method as Example 1.

Figure 22:
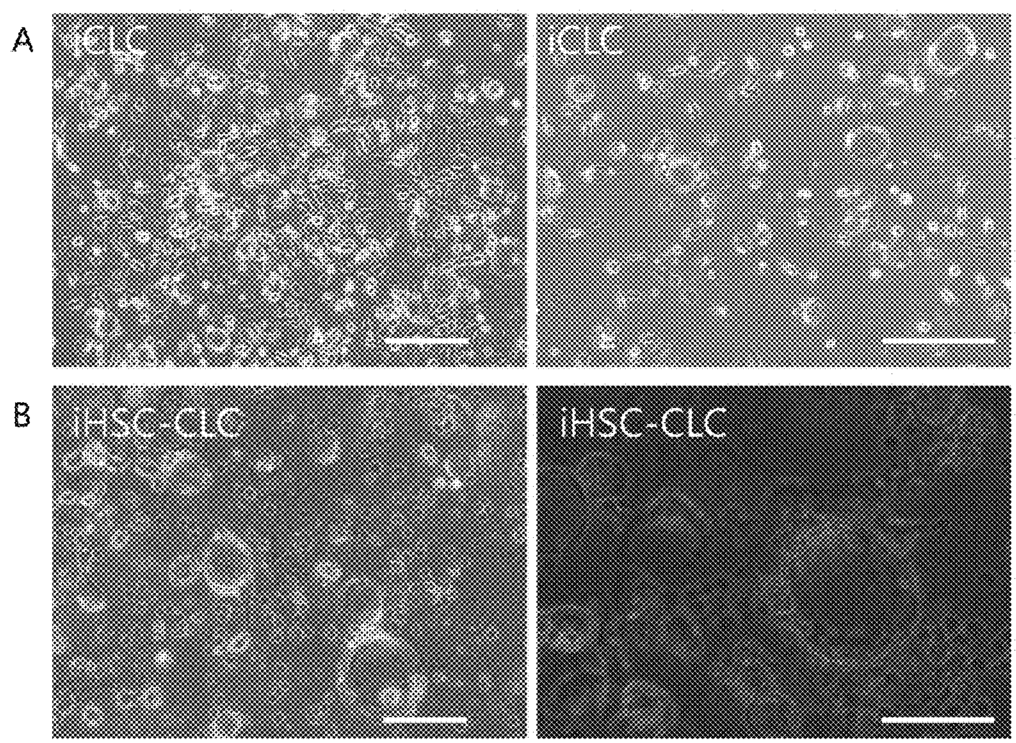
FIG. 22 shows morphological changes from somatic cells into cholangiocytes by direct conversion factors, observed with a microscope, according to one example of the present invention. The scale bar shows 100 um.

After inducing cholangiocytes from fibroblasts by conducting the above method, the result of observing morphological changes of cells in the same method as Example 1 was shown in FIG. 22. The right figure is a figure magnifying the left figure. The scale bar shows 100 um.

A of FIG. 22 shows the result of observing cholangiocytes after direct conversion from fibroblasts into cholangiocytes (iCLC) was induced in the above method with a microscope, B of FIG. 22 shows the result of observing cholangiocytes in which differentiation was induced in the same method as Referential Example 2, after introducing direct conversion factor genes into fibroblasts in the above method (iHSC-CLC) with a microscope.

As shown in FIG. 22, when direct conversion into cholangiocytes was induced by introducing direct conversion factor genes into fibroblasts, ductal structures which were observed in cholangiocytes of the case that the hepatic stem cells were differentiated into cholangiocytes were confirmed.

In addition, by immunofluorescence staining analysis of cholangiocytes in which direct conversion from fibroblasts into cholangiocytes was induced in the above method, the expression of CK19 and CK7, which are markers expressed specifically on the surface of cholangiocytes was confirmed in the same method as Referential Example 4.

Figure 23:
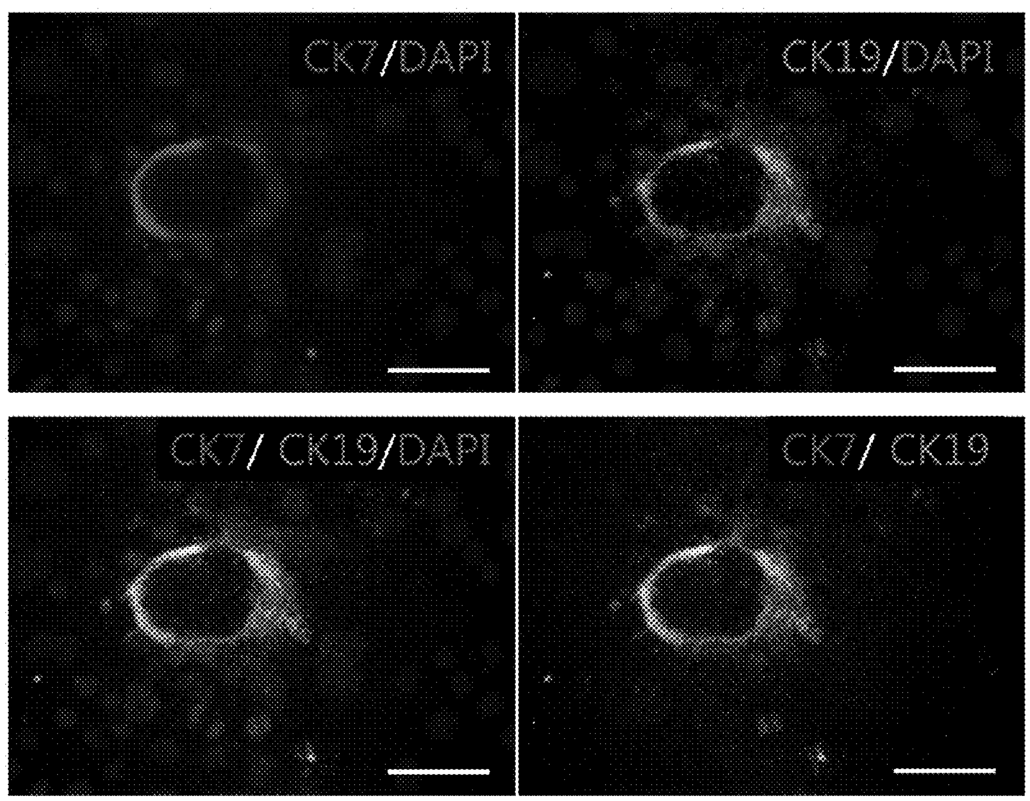
FIG. 23 show whether direct conversion from somatic cells into cholangiocytes by direct conversion factors occurs, observed by fluorescence staining, according to one example of the present invention. The scale bar shows 100 um.

The experimental result was shown in FIG. 23.

As shown in FIG. 23, it was confirmed that CK19 and CK7, which are markers expressed specifically on the surface of cholangiocytes were expressed in cholangiocytes in which direct conversion from fibroblasts into cholangiocytes was induced in the above method.

Example 6. Confirmation of Direct Conversion of Human Fibroblasts by Direct Conversion Factors 6-1. Induction of Direct Conversion of Human Fibroblasts into Hepatic Stem Cells and Hepatocytes by Direct Conversion Factors To induce direct conversion from human fibroblasts into hepatic stem cells and hepatocytes by different combination of direct conversion factors, experiments were conducted in the following method.

Specifically, direct conversion factors were introduced into fibroblasts in the same method as Example 1, but the combination of the direct conversion factors was as follows:

OU, OUT, ON7, or ON7T (O:OCT4, NM_002701.5., SEQ ID NO: 73); U:NR4A2/NURR1, NM_006186.3., SEQ ID NO: 77; N7:NR4A1/NUR77, NM_001202233.1., SEQ ID NO: 79; T:TBX3, NM_005996.3., SEQ ID NO: 81).

Figure 24:
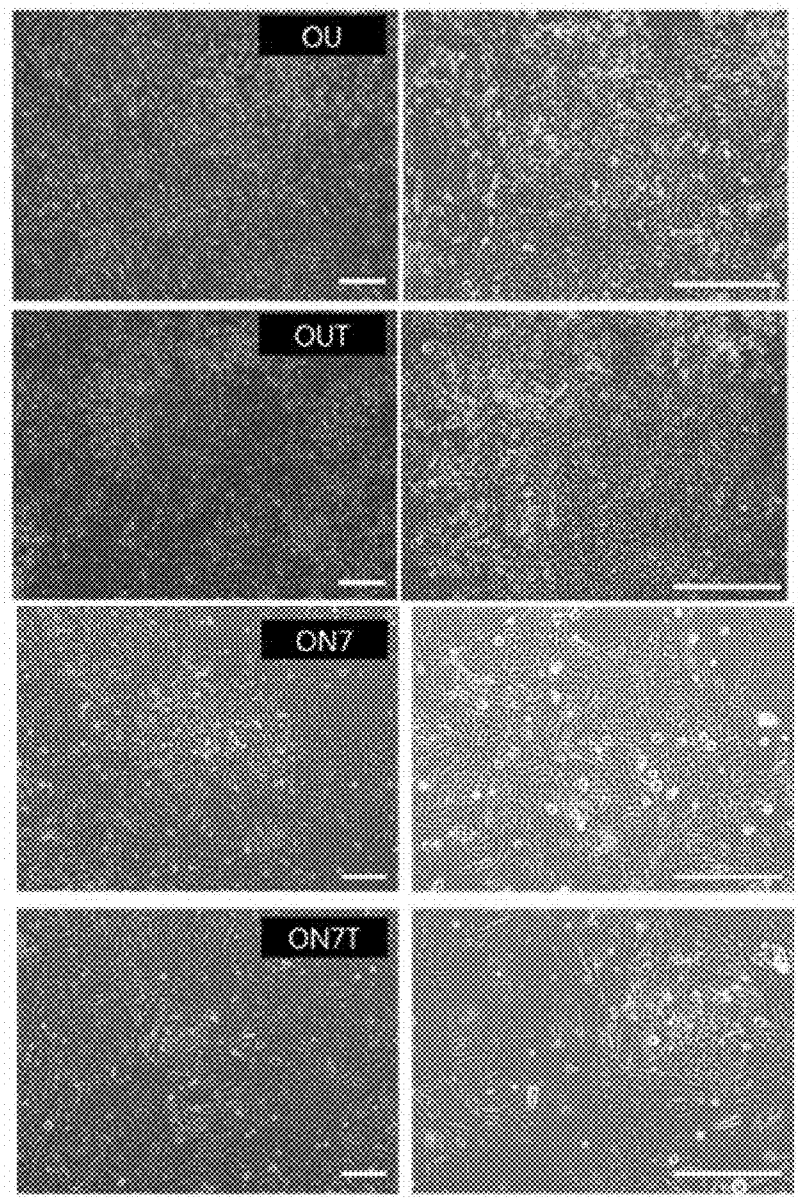
FIG. 24 shows morphological changes from fibroblasts into hepatic stem cells and hepatocytes by direct conversion factors, observed with a microscope, according to one example of the present invention. The scale bar shows 250 um.

The result of observing direct conversion induced cells from fibroblasts in the above method with a microscope was shown in FIG. 24.

FIG. 24 confirmed that there were no morphological properties of fibroblasts, by observing morphological changes of cells in the same method as Example 1, after introducing the direct conversion factors in fibroblasts.

The right figure is a figure magnifying the left figure. The scale bar shows 250 um.

6-2. Confirmation of Induction of Direct Conversion of Human Fibroblasts into Hepatic Stem Cells and Hepatocytes by Direct Conversion Factors 6-2-1 Immunofluorescence Analysis Cells which were directly converted from human fibroblasts in the method of Example 6-1 were immunofluorescence analyzed with hepatic stem cell markers and hepatocyte markers in the same method as Referential Example 4.

Figure 25:
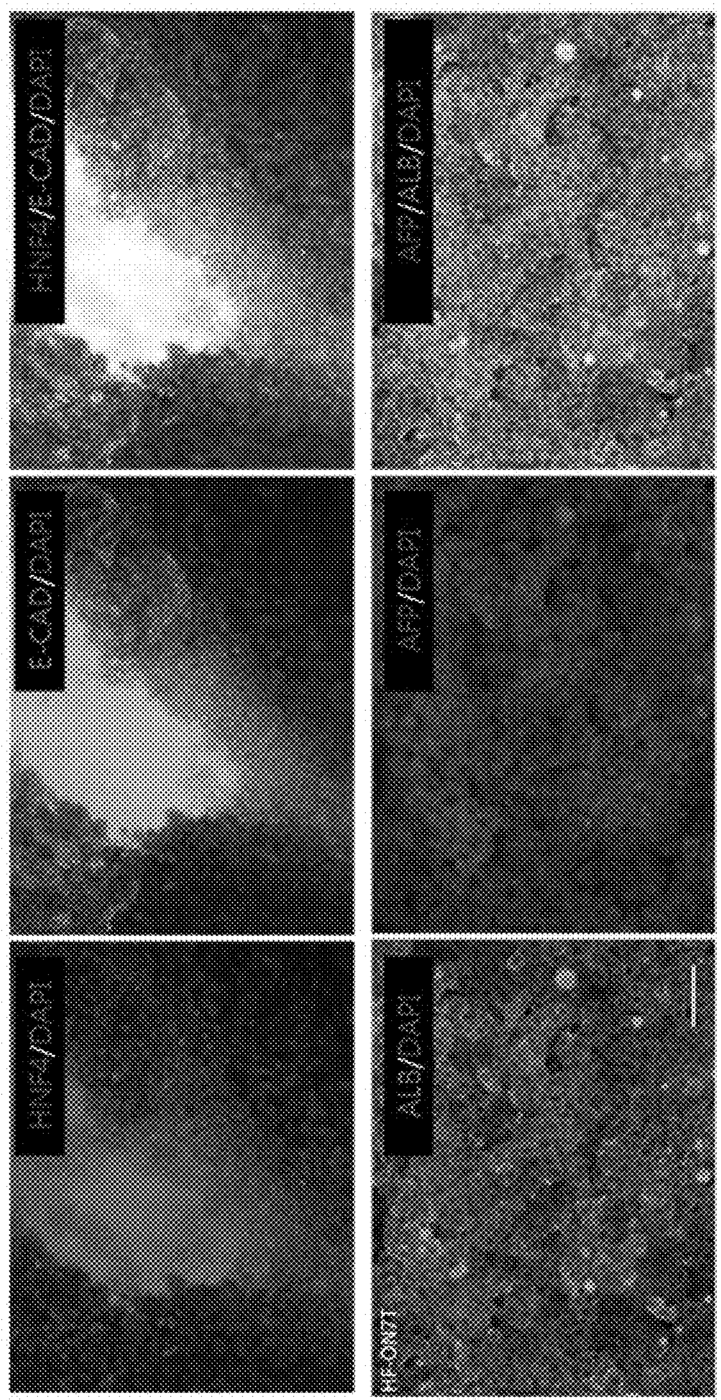
FIG. 25 shows confirmation of that cells which are directly converted in fibroblasts express hepatic stem cell marker proteins (HNF4, E-Cadherin), and express hepatocyte marker proteins (AFP, ALB). The scale bar shows 100 um.

The experimental result was shown in FIG. 25.

As shown in FIG. 25, it was confirmed that cells which were directly converted from human fibroblasts in the method of Example 601 expressed hepatic stem cell marker proteins (HNF4, E-Cadherin) and hepatocyte marker proteins (AFP, ALB).

Therefore, by the above result, it was confirmed that hepatic stem cells and hepatocytes could be directly converted from fibroblasts by introducing direct conversion factors.

6-2-2. Real-Time RT-PCR Analysis

The expression of fibroblast markers, hepatic stem cell markers and hepatocyte markers which were directly converted from human fibroblasts in the method of Example 6-1 was confirmed by real-time reverse transcription PCR.

Specifically, after introducing direct conversion factors into human fibroblasts in the method of Example 6-1, cells were sampled every 3 days, 1 week, and 3 weeks, to extract total RNA using RNeasy® mini kit (Qiagen), and cDNA was synthesized using 500 ng of total RNA extracted and SuperScript® III transcriptase (Invitrogen), and real-time PCR analysis of cDNA 20 uL volume synthesized above was performed using primers described below and LightCycler® 480 SYBR Green I Mastermix (Roche). The experiment was conducted by repeating 3 times, and normalization was done with housekeeping gene GAPDH, and the gene expression was measured by Ct value calculation method.

HF is when direct conversion factors were introduced into human fibroblasts, and D3 is 3 days after introducing the direct conversion factors, and 1 wk is 1 week after introducing the direct conversion factors, and 3 wk is 3 weeks after introducing the direct conversion factors, and liver cancer cell line HepG2 (ATCC) is a positive control group.

Primer sequences used in Real-time RT-PCR were shown below (sequences below were represented in the 5' to 3' direction).

```
hCOLIA2-qF:
                                  (SEQ ID NO: 59)
CAGAGTGGAGCAGTGGTTAC

hCOLIA2-qR:
                                  (SEQ ID NO: 60)
CAGTTCTTGGCTGGGATGTT

hTWIST2-qF:
                                  (SEQ ID NO: 61)
CCTCAGCTACGCCTTCTC
```

-continued hTWIST2-qR:
(SEQ ID NO: 62)
GAATGCATCCCAATTCCACTTG hALB-qF:
(SEQ ID NO: 63)
GCACAGAATCCTTGGTGAACAG hALB-qR:
(SEQ ID NO: 64)
ATGGAAGGTGAATGTTTCAGCA hAFP qF:
(SEQ ID NO: 65)
GCTTGGTGGTGGATGAAACA hAFP qR:
(SEQ ID NO: 66)
TCCTCTGTTATTTGTGGCTTTTG hHNF4a qF:
(SEQ ID NO: 67)
TCGCAGATGTGTGTGAGTCC hHNF4a qR:
(SEQ ID NO: 68)
CACTCAACGAGAACCAGCAG hFOXA2 qF:
(SEQ ID NO: 69)
ACCACTACGCCTTCAACCAC hFOXA2 qR:
(SEQ ID NO: 70)
GCCTTGAGGTCCATTTTGTG hGAPDH R:
(SEQ ID NO: 71)
GGAGGAGTGGGTGTCGCTGT hGAPDH F:
(SEQ ID NO: 72)
GTGGACCTGACCTGCCGTCT The experimental result obtained by conducting the above method was shown in FIG. 26.

Figure 26:
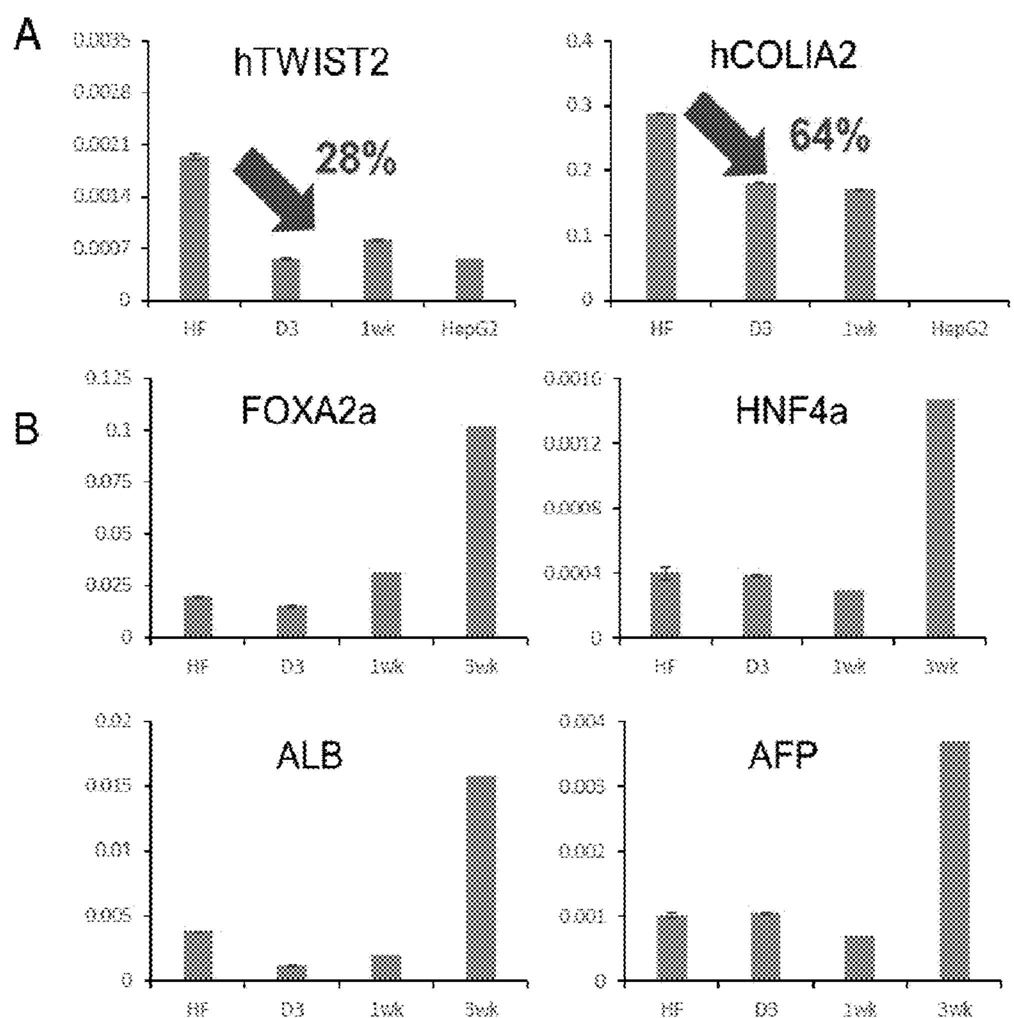
FIG. 26 shows the result of confirmation of that in cells which are directly converted in fibroblasts, the expression of fibroblast-specific marker (TWIST2, COLIA2) is reduced, but the expression of hepatic stem cell and hepatocyte-specific markers is increased, according to one example of the present invention.

As shown in FIG. 26, it was confirmed that in cells that had passed three days after introducing direct conversion factors, the expression of fibroblast-specific markers (TWIST2, COLIA2) was decreased 72% and 36%, respectively, while in cells that had passed three days after introducing direct conversion factors, the expression of HNF4α was increased 367%, and the expression of FOXA2 was increased 513%, and the expression of AFP was increased 363%, and the expression of ALB was increased 421% (hepatic stem cell (HNF4α, FOXA2), and hepatocyte (AFP, ALB) markers).

6-3. Analysis of Properties of Directly Converted Hepatocytes

The expression of hepatocyte-specific markers of cells which were directly converted from fibroblasts in the method of Example 6-1 was confirmed in the same method as Referential Example 4, and LDL uptake assay was conducted in the same method as Example 2, and glycogen storage function of hepatocytes was confirmed in the same method as Example 2 (Periodic acid-Schiff (PAS) staining), and ICG uptake analysis was conducted in the same method as Example 2.

Figure 27:
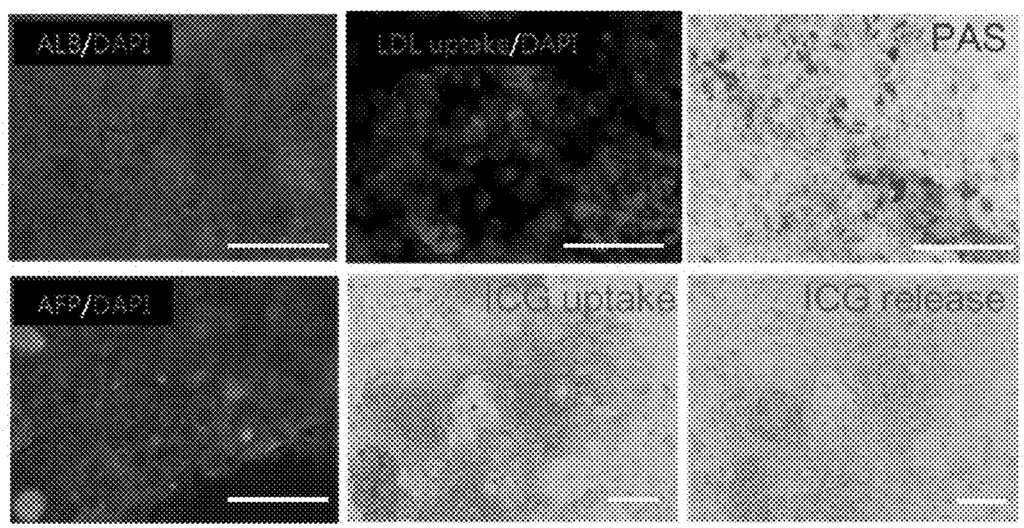
FIG. 27 shows confirmation of that cells which are directly converted in fibroblasts express hepatocyte-specific markers (AFP, ALB) and absorb LDL (low-density lipoprotein) through endocytosis mediated by LDL receptors, and confirmation of Periodic acid-Schiff (PAS) staining exhibiting glycogen storage, and confirmation of detoxification ability by ICG absorptive cells (green), according to one example of the present invention.

As a result, as shown in FIG. 27, it was confirmed that cells which were directly converted from fibroblasts in the method of Example 6-1 expressed hepatocyte-specific markers (AFP, ALB) and absorbed LDL (low-density lipoprotein) through endocytosis mediated by LDL receptors, and Periodic acid-Schiff (PAS) staining showing glycogen storage was confirmed, and detoxification ability was confirmed by that ICG uptake cells (green) disappeared rapidly after 6 hrs.

By the above results, it was demonstrated that cells which were directly converted from fibroblasts in the method of Example 6-1 had normal hepatocyte properties.

6-4. Confirmation of Direct Conversion of Human Fibroblasts into Hepatobiliary Cells by Direct Conversion Factors In order to confirm whether direct conversion from human fibroblasts into hepatobiliary cells by different combination of direct conversion factors was done, experiments were performed in the following method.

Specifically, after introducing direct conversion factors into human fibroblasts in the same method as Example 6-1 and culturing the cells in a plate coated with Matrigel® the same method as Referential Example 3, immunofluorescence staining was conducted in the same method as Referential Example 4, and the combination of direct conversion factors was as follows:

OU, OUT, ON7, or ON7T (O:OCT4, NM_002701.5., SEQ ID NO: 73); U:NR4A2/NURR1, NM_006186.3., SEQ ID NO: 77; N7:NR4A1/NUR77, NM_001202233.1., SEQ ID NO: 79; T:TBX3, NM_005996.3., SEQ ID NO: 81).

Figure 28:
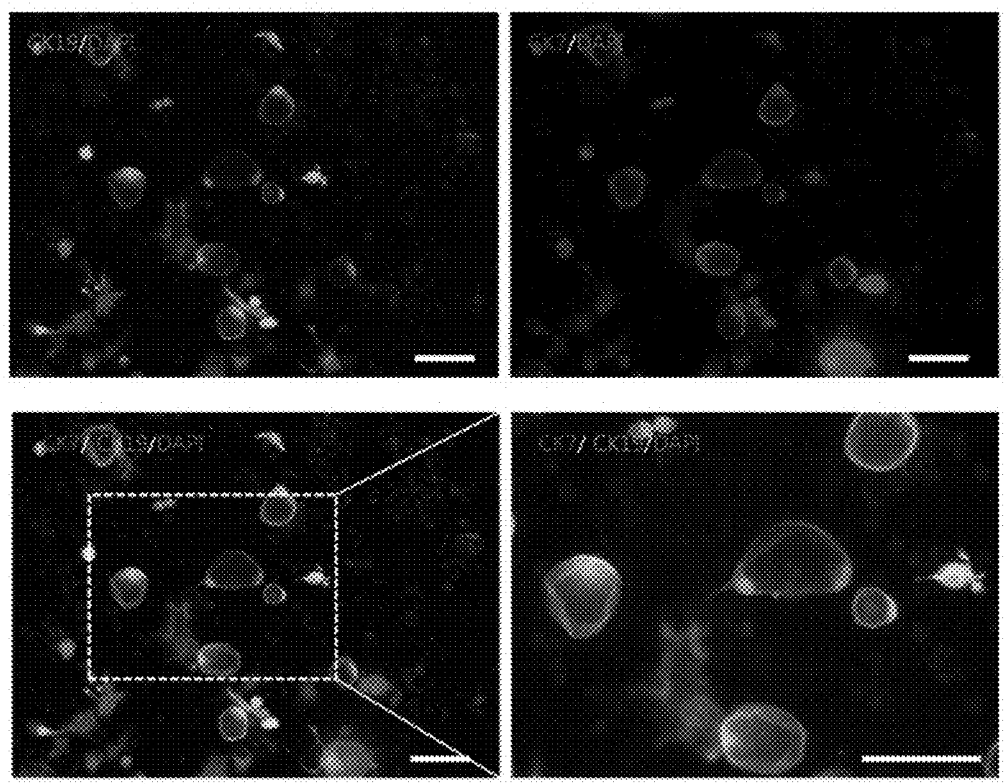
FIG. 28 shows induced direct conversion into cholangiocytes by introducing direct conversion factors into fibroblasts, confirmed by fluorescence staining with cholangiocyte marker proteins (CK19, CK7), according to one example of the present invention. The scale bar shows 100 um.

The experimental result obtained by conducting the above method was shown in FIG. 28.

As shown in FIG. 28, it was confirmed that cholangiocyte marker proteins (CK19, CK7) expressed in ductal structures were expressed, when cells which direct conversion factors were introduced into human fibroblasts were cultured in a plate coated with Matrigel®, and by this, it was confirmed that direct conversion into cholangiocytes was induced, when the direct conversion factors were introduced into fibroblasts.

What is claimed is:

1. A method of direct conversion from a somatic cell to a hepatic stem cell, the method comprising the steps of introducing a composition for inducing direct conversion into the somatic cell, and culturing the somatic cell in a medium capable of generating a hepatic stem cell wherein the composition comprises:

(1) at least one selected from the group consisting of octamer-binding transcription factor 4 (OCT4) protein, a nucleic acid molecule encoding OCT4 protein, and a vector into which the nucleic acid molecule encoding OCT4 protein is introduced, and (2) at least one selected from the group consisting of nuclear receptor subfamily 4 group A member 1 (NR4A1) protein, nuclear recept or subfamily 4 group A member 2 (NR4A2) protein, a nucleic acid molecule encoding NR4A1 protein, a nucleic acid molecule encoding NR4A2 protein, a vector into which the nucleic acid molecule encoding NR4A1 protein is introduced, and a vector into which the nucleic acid molecule encoding NR4A2 protein is introduced, wherein the somatic cell is fibroblast.

2. The method of claim 1, wherein the composition for inducing direct conversion further comprises at least one selected from the group consisting of T-box transcription factor 3 (TBX3) protein, nuclear receptor subfamily 5 group A member 1 (NR5A1) protein, nuclear receptor subfamily 5 group A member 2 (NR5A2) protein, nuclear receptor subfamily 0 group B member 2 (NR0B2) protein, a nucleic acid molecule encoding TBX3 protein, a nucleic acid molecule encoding NR5A1 protein, a nucleic acid molecule encoding NR5A2 protein, a nucleic acid molecule encoding NR0B2 protein, a vector into which the nucleic acid molecule encoding TBX3 protein is introduced, a vector into which the nucleic acid molecule encoding NR5A1 protein is introduced, a vector into which the nucleic acid molecule encoding NR5A2 protein is introduced, and a vector into which the nucleic acid molecule encoding NR0B2 protein is introduced.

3. The method of claim 1, wherein any of the vectors is at least one selected from the group consisting of plasmid vector, cosmid vector, virus vector, Lentivirus vector, Retrovirus vector, Human immunodeficiency virus (HIV) vector, Murineleukemia virus (MLV) vector, Avian sarcoma/leukosis (ASLV) vector, Spleen necrosis virus (SNV) vector, Rous sarcoma virus (RSV) vector, Mouse mammary tumor virus (MMTV) vector, Adenovirus vector, Adeno-associated virus vector and Herpes simplex virus vector.

4. The method of claim 1, further comprising a step of culturing the hepatic stem cell in a medium capable of differentiating the directly converted hepatic stem cell into a hepatocyte to generate the hepatocytes.

5. The method of claim 1, further comprising a step of culturing the hepatic stem cell in a medium capable of differentiating the directly converted hepatic stem cell into a cholangiocyte to generate the cholangiocyte.

* * * * *